US011385230B2

(12) United States Patent
Fedorak et al.

(10) Patent No.: US 11,385,230 B2
(45) Date of Patent: Jul. 12, 2022

(54) METHODS FOR THE ASSESSMENT OF COLORECTAL CANCER AND COLORECTAL POLYPS BY MEASUREMENT OF METABOLITES IN URINE

(71) Applicant: The Governors Of The University of Alberta, Edmonton (CA)

(72) Inventors: Richard Neil Fedorak, Edmonton (CA); Haili Wang, Edmonton (CA)

(73) Assignee: The Governors of the University of Alberta, Edmonton (CA)

(*) Notice: Subject to any disclaimer, the term of this patent is extended or adjusted under 35 U.S.C. 154(b) by 585 days.

(21) Appl. No.: 16/294,161

(22) Filed: Mar. 6, 2019

(65) Prior Publication Data

US 2019/0271701 A1 Sep. 5, 2019

Related U.S. Application Data

(62) Division of application No. 13/699,124, filed as application No. PCT/CA2011/050315 on May 20, 2011, now Pat. No. 10,267,800.

(60) Provisional application No. 61/347,043, filed on May 21, 2010.

(51) Int. Cl.
*G01N 33/574* (2006.01)
*G01N 33/493* (2006.01)

(52) U.S. Cl.
CPC ..... *G01N 33/57419* (2013.01); *G01N 33/493* (2013.01); *G01N 2560/00* (2013.01); *G01N 2800/06* (2013.01); *G01N 2800/60* (2013.01); *Y10T 436/24* (2015.01)

(58) Field of Classification Search
CPC .......... G01N 33/57419; G01N 33/493; G01N 2560/00; G01N 2800/06; Y10T 436/24
See application file for complete search history.

(56) References Cited

U.S. PATENT DOCUMENTS

| 6,423,491 | B1 | 7/2002 | Howe et al. |
| 7,553,616 | B2 | 6/2009 | Kaddurah-Daouk et al. |
| 9,134,313 | B2 | 9/2015 | Kawakita et al. |
| (Continued) | | | |

FOREIGN PATENT DOCUMENTS

| JP | 2009508091 A | 2/2009 |
| WO | 2007088537 A2 | 8/2007 |
| (Continued) | | |

OTHER PUBLICATIONS

"Trigonelline in Coffee", Apr. 23, 2015: https://www.coffeechemistry.com/chemistry/alkaloids/trigonelline-incoffee?print= 1 &tmpl= component.

(Continued)

*Primary Examiner* — Christopher Adam Hixson
(74) *Attorney, Agent, or Firm* — Troutman Pepper Hamilton Sanders LLP

(57) ABSTRACT

Methods for the diagnosis of CRC, colorectal polyps in general and adenomatous polyps in particular by measurement of metabolites in urine are described. In some embodiments, certain metabolites are identified as being elevated or reduced in concentration or quantity in subjects with CRC and/or colorectal polyps as compared with subjects without CRC or colorectal polyps. The measurement of these metabolites in urine can indicate the presence of CRC or colorectal polyps in general or adanomatous polyps in particular in a subject.

8 Claims, 30 Drawing Sheets

(56) References Cited

U.S. PATENT DOCUMENTS

| | | | |
|---|---|---|---|
| 2007/0178599 | A1 | 8/2007 | Kaddurah-Daouk et al. |
| 2007/0161059 | A1 | 12/2007 | Kawakita et al. |
| 2008/0255764 | A1 | 10/2008 | Ritchie et al. |
| 2009/0075284 | A1 | 3/2009 | Chinnaiyan et al. |
| 2012/0197539 | A1 | 8/2012 | Slupsky |

FOREIGN PATENT DOCUMENTS

| | | | |
|---|---|---|---|
| WO | 2008075663 | A1 | 6/2008 |
| WO | 2009037572 | A2 | 3/2009 |
| WO | 2011041892 | A1 | 4/2011 |
| WO | 2011136343 | A1 | 11/2011 |

OTHER PUBLICATIONS

Allred, et al., "Trigonelline is a Novel Phytoestrogen in Coffee Beans1 ,2" The Journal of Nutrition Biochemical, Molecular, and Genetic Mechanisms (2009) No. 139, pp. 1833-1838.
Berode, et al., "Urinary methanol and formic acid as indicators of occupation exposure to methyl formate", Int. Arch. Occuup. Environ. Health, 2000, v. 73, pp. 410-414.
Bond, "Colon Polyps and Cancer," Endoscopy; 35 (1):27-35, (2003).
Bouatra, S. et al., "The Human Urine Metabolome" PLOS One (2013) vol. 8, Issue 9, e73076, p. 1-28.
Chan et al. "Metabolic Profiling of Human Colorectal Cancer Using High-Resolution Magic Angle Spinning Nuclear Magnetic Resonance (HR-MAS NMR) Spectroscopy and Gas Chromatography Mass Spectrometry (GC/MS)", J. Proteom. Res., 2009, v.8, pp. 352-361.
Claudino, W.M. et al., "Metabolomics: Available Results, Current Research Projects in Breast Cancer, and Future Applications" Journal of Clinical Oncology (2007) vol. 25, pp. 2840-2846.
Communication issued by the Australia Patent Office in Australian Application No. 2011256064 dated Feb. 26, 2016.
Communication issued by the Australia Patent Office in Australian Application No. 2011256064 dated Jan. 29, 2015.
Communication issued by the Australia Patent Office in Australian Application No. 2011256064 dated May 20, 2016.
Communication issued by the Canada Patent Office in Canada Application No. 2799757 dated May 16, 2017.
Communication issued by the Canada Patent Office in Canada Application No. 2799757 dated May 4, 2016.
Communication issued by the Canada Patent Office in Canada Application No. 2799757 dated Nov. 30, 2017.
Communication issued by the Canada Patent Office in Canada Application No. 2799757 dated Oct. 25, 2016.
Communication issued by the European Patent Office in European Application No. 11782836.8 dated Apr. 29, 2015.
Communication issued by the European Patent Office in European Application No. 11782836.8 dated Feb. 8, 2016.
Communication issued by the European Patent Office in European Application No. 11782836.8 dated Jun. 17, 2014.
Communication issued by the European Patent Office in European Application No. 11782836.8 dated Oct. 29, 2013.
Communication issued by the European Patent Office in European Application No. 11782836.8 dated Oct. 6, 2016.
Communication issued by the Japan Patent Office in Japanese Application No. 2013-510462 dated Jan. 13, 2015.
Communication issued by the Japan Patent Office in Japanese Application No. 2013-510462 dated Sep. 15, 2015.
Denkert, C., et al., "Metabolite profiling of human colon carcinoma—deregulation of TCA cycle and amino acid turnover," Molecular Cancer, 2008, vol. 7, No. 1, pp. 1-15.
Eisner, R. "A Machine-Learned Predictor of Colonic Polyps Based on Urinary Metabolomics" BioMed Research International, Hindawi Publishing Corporation (2013) Article ID 303982, pp. 1-11, 11 pages total.

EPO Application No. EP 11782836.8 (Published as EP2572193), Supplementary European Search Report and European Search Opinion, dated Nov. 20, 2013.
Eriksson, L., et al., "Multi- and Megavariate Data Analysis: Part II, Method Extensions and Advanced Applications," Umetrics Academy, 2005, Chapter 23.
Eriksson, L., et al., "Separating Y-predictive and Y-orthogonal variation in multi-block spectral data," Journal of Chemometrics, 2006, vol. 20, pp. 352-361.
Gabrielsson, J., et al., "The OPLS methodology for analysis of multi-block batch process data," Journal of Chemometrics, 2006, vol. 20, pp. 362-369.
Griner, P.F., et al., "Selection and interpretation of diagnostic tests and procedures," Principles and applications, Ann. Intern. Med., 1981, vol. 94(4 Pt 2), pp. 557-592.
Gurudu, S.R., et al., "Sessile serrated adenomas: Demographic, endoscopic and pathological characteristics," World Journal of Gastroenterology, 2010, vol. 16(27), pp. 3402-3405.
Guy et al., "Global Metabolic Profiling Analysis on Human Urine by UPLC-TOFMS: Issue and Method Validation in Nutritional Metabolomics" Journal of Chromatography B (2008) vol. 871, pp. 253-260.
Hsu, W-Y., et al., "Analysis of urinary nucleosides as potential tumor markers in human colorectal cancer by high performance liquid chromatography/electrospray ionization tandem mass spectrometry," Clinica Chimica Acta, 2009, vol. 402, pp. 31-37.
Jass, J.R., "Hyperplastic-like Polyps as Precursors of Microsatellite-Unstable Colorectal Cancer," American Journal of Clinical Pathology, 2003, vol. 119, pp. 773-775.
Karpasea-Jones, Joanna, "Your Cup of Coffee Could Protect You from Colon Cancer": http://www.empowher.com/colorectal-cancer/content/your-cup-coffee-could-protect-you-colon-cancer; source: Texas Agrilife Communications Press Release, Kathleen Philips, Nov. 12, 2009.
Johnson, J.C. et al., "Urine PGE-M: A Metabolite of Prostaglandin E2 as a Potential Biomarker of Advanced Colorectal Neoplasia" Clinical Gastroenterology and Hepatology (2006) vol. 4, pp. 1358-1365.
Levin et al., "Screening and Surveillance for the Early Detection of Colorectal Cancer and Adenomatous Polyps, 2008: A Joint Guideline From the American Cancer Society, the US Multi-Society Task Force on Colorectal Cancer, and the American College of Radiology," Gastroenterology, 134: 1570-1595, (2008).
Ma, Y.-L., et al., "Ultra-High Performance Liquid Chromatography-Mass Spectrometry for the Metabolomic Analysis of Urine in Colorectal Cancer," Dig. Dis. Sci., 2009, vol. 54, pp. 2655-2662.
Muto et al., "The Evolution of Cancer of the Colon and Rectum," Cancer, 36:2251-2270, (1975).
Nambiar, P.R. et al., "An 'omics' based survey of human colon cancer" Mutation Research/Fundamental and Molecular Mechanisms of Mutagenesis (2010) vol. 693, pp. 3-18.
Noffsinger, A.E., "Serrated Polyps and Colorectal Cancer: New Pathway to Malignancy," Annual Review of Pathology-Mechanisms of Disease, 2009, vol. 4, pp. 343-364.
O'Brien, M.J., "Hyperplastic and Serrated Polyps of the Colorectum," Gastroenterology Clinics of North America, 2007, vol. 36, pp. 947-968.
Qiu, Y., et al., "Urinary Metabonomic Study of Colorectal Cancer," Journal of Proteome Research, 2010, vol. 9, pp. 1627-1634.
Sarosiek, I. et al., "Urinary Metabolites as Noninvasive Biomarkers of Gastrointestinal Diseases: A Clinical Review" World Journal of Gastrointestinal Oncology (2016) vol. 8, Issue 5, pp. 459-465.
Slupsky, C.M., et al., "Pneumococcal Pneumonia: Potential for Diagnosis through a Urinary Metabolic Profile," Journal of Proteome Research, 2009, vol. 8, No. 12, pp. 5550-5558.
Spigelman, A.D. et al., "Caffeine Phenotyping of Cytochrome P4501A2, N-Acetyltransferase, and Xanthine Oxidase in Patients with Familial Adenomatous Polyposis" Gut (1995) vol. 36, pp. 251-254.
Supporting Information for Qiu, Y. et al., "Urinary Metabonomic Study on Colorectal Cancer" Journal of Proteome Research (2010) vol. 9, pp. 1627-1637, 9 pages total.

(56) References Cited

OTHER PUBLICATIONS

The Human Metabolome Database (HMDB), Metabocard for Ascorbic acid (HMDB00044). [Retrieved from the Internet Dec. 15, 2016: <http://www.hmdb.ca/metabolites/hmdb00044>].

The Human Metabolome Database (HMDB), Metabocard for Trigonelline (HMDB00875). [Retrieved from the Internet Dec. 15, 2016: <http://www.hmdb.ca/metabolites/HMDB00875>].

Torlakovic, E., et al., "Morphologic Reappraisal of Serrated Colorectal Polyps," American Journal of Surgical Pathology, 2003, vol. 27(1), pp. 65-81.

Trygg, J., "O2-PLS for qualitative and quantitative analysis in multivariate calibration," Journal of Chemometrics, 2002, vol. 16, pp. 283-293.

Trygg, J., "Prediction and spectral profile estimation in multivariate calibration," Journal of Chemometrics, 2004, vol. 18, pp. 166-172.

Trygg, J., et al., "O2-PLS, a two-block (X-Y) latent variable regression (LVR) method with an integral OSC filter," Journal of Chemometrics, 2003, vol. 17, pp. 53-64.

Trygg, J., et al., "Orthogonal projections to latent structures (O-PLS)," Journal of Chemometrics, 2002, vol. 16, pp. 119-128.

Vapnik, V.N. (1995) The Nature of Statistical Learning Theory. New York, NY: Springer.

Waikar and Bonventre, "Can We Rely on Blood Urea Nitrogen as a Biomarker to Determine When to Initiate Dialysis?", Clin. J. Am. Soc. Neprol., 2006, v. 1, pp. 903-906.

Wang, et al., "Development and Validation of a Highly Sensitive Urine-Based Test to Identify Patients with Colonic Adenomatous Polyps" Clinical and Translational Gastroenterology (2014) vol. 5, e54, pp. 1-8.

Wang, H., et al., "Metabolomics and detection of colorectal cancer in humans: a systematic review," Future Oncology, 2010, vol. 6(9), pp. 1395-1406.

Wang, H., et al., "The Role of NMR Urine Metabolomics as a New Method for Screening Colorectal Cancer—A Preliminary Analysis," Canadian Journal Gastroenterology, 2009, vol. 23(Supplement A): 144, Canadian Digestive Diseases Week: Feb. 27-Mar. 2, 2009 in Banff, Alberta.

Wang, W., et al., "Urinary metabolic profiling of colorectal carcinoma based on online affinity solid phase extraction-high performance liquid chromatography and ultra performance liquid chromatography-mass spectrometry," Mal. BioSyst., 2010, vol. 6, pp. 1947-1955.

Want et al., "The Expanding Role of Mass Spectrometry in Metabolite Profiling and Characterization" ChemBioChem (2005) vol. 6, pp. 1941-195.

Wenzel, "Ascorbic acid suppresses drug-induced apoptosis in human colon cancer cells by scavenging mitochondrial superoxide anions", Carcinogenesis (2004) vol. 25, No. 5, pp. 703-712.

WIPO Application No. PCT/CA2011/050315, International Preliminary Reporton Patentability, dated Nov. 27, 2012.

WIPO Application No. PCT/CA2011/050315, International Search Report, dated Aug. 22, 2011.

WIPO Application No. PCT/CA2011/050315, Written Opinion of the International Searching Authority, dated Aug. 22, 2011.

Wishart, D.S., "Is Cancer a Genetic Disease or a Metabolic Disease?" EBioMedicine (2015) vol. 2, pp. 478-479.

Zweig, M.H., et al., "Receiver-Operating Characteristic (ROC) Plots: A Fundamental Evaluation Tool in Clinical Medicine," Clin. Chem., 1993, vol. 39(4), pp. 561-577.

Office Action dated Mar. 23, 2021 in connection with Canadian Application No. 3,065,979.

Iwasaki et al., "Current status of urinary diagnostic biomarkers for colorectal cancer", Clinica Chimica Acta., vol. 498, pp. 76-83, Aug. 14, 2019.

Hiramatsu et al., "N1, N12-Diacetylspermine as a Sensitive and Specific Novel Marker for Early-and Late-Stage Colorectal and Breast Cancers", Clin. Cancer Res., 11(8), pp. 2986-2990, Apr. 15, 2005.

Huang et al., "Serum tryptophan decrease correlates with immune activiation", British J. of Cancer, 86, pp. 1691-1692, 2002.

Kuwata et al., "Increase of N-diacetylspermine in tissues from colorectal cancer and its liver metastasis1, N 12-diacetylspermine in tissues from colorectal cancer and its liver metastasis", J. of Cancer Res. & Clin. Oncology, 139 (6), pp. 925-932, Jun. 2013.

Rattray et al., "Environmental influences in the etiology of colorectal cancer: the premise of metabolomics", Curr. Pharmacl, Rep., 3(3) pp. 114-125, Jun. 2017.

International Search Report dated Oct. 11, 2018 in connection with PCT/CA2018/050421.

Deng, L. et al., "Clinical Validation of a Novel Urine-Based Metabolomic Test for the Detection of Colonic Polyps on Chinese Population" Int. J. Colorectal Disease (2017) vol. 32, pp. 741-743.

METHODS FOR THE ASSESSMENT OF COLORECTAL CANCER AND COLORECTAL POLYPS BY MEASUREMENT OF METABOLITES IN URINE

CROSS-REFERENCE TO RELATED APPLICATIONS

This application is a Divisional of U.S. application Ser. No. 13/699,124, filed on Nov. 20, 2012, which is the U.S. National Stage of International Application PCT/CA2011/050315 filed May 20, 2011, which designates the U.S. and was published by the International Bureau in English on Nov. 24, 2011, and which claims the benefit of U.S. Provisional Application No. 61/347,043, filed May 21, 2010, all of which are hereby incorporated by reference in their entirety.

FIELD OF THE INVENTION

This invention relates to the assessment of colorectal cancer and colorectal polyps by measurement of metabolites in urine.

BACKGROUND

Colorectal Cancer (CRC) is among the leading causes of morbidity. The chance of surviving CRC is closely related to the stage of the disease at diagnosis; the earlier the diagnosis, the greater the likelihood of survival. In many instances CRC is preceded by colorectal polyps, particularly adenomatous colorectal polyps. If identified early at the colorectal polyp or precancerous lesion stage, CRC is more likely to be curable. Therefore, subjects with CRC and/or colorectal polyps would greatly benefit from early diagnosis.

Current CRC screening methods consist of one or a combination of the followings: fecal occult blood testing (FOBT), flexible sigmoidoscopy, air-contrast barium enema, computerized tomography colonography (CTC) and/or colonoscopy. These current screening methods all have limitations or potential risks that limit their application.

Colonoscopy is currently the standard test for the presence or absence of CRC or colorectal polyps. However, colonoscopy is invasive and can impose unnecessary hazards and risks caused by sedation or the procedure itself. A known non-invasive CRC diagnostic method is FOBT. FOBT, however, has very low sensitivity in detection of CRC and is unattractive as the handling of fecal matter is required. CTC is a recent non-invasive technique for imaging the colon. However, its performance varies due primarily to technological differences in the subject preparation and the hardware and software used for the analysis. Several new screening methods based on DNA analysis are now available. These are typically PCR-based assays used to identify mutations known to occur in the adenoma-to-carcinoma sequence, or in familial CRC. However, whether genomics-based tests will result in high diagnostic accuracy for sporadic CRC remains to be seen.

Accordingly, there is a need to develop improved methods of assessing CRC and colorectal polyps in a subject.

SUMMARY

Methods for the diagnosis of CRC, colorectal polyps in general and adenomatous polyps in particular by measurement of metabolites in urine are described. In some embodiments, certain metabolites are identified as being elevated or reduced in concentration or quantity in subjects with CRC and/or colorectal polyps as compared with subjects without CRC or colorectal polyps. The measurement of these metabolites in urine can indicate the presence of CRC or colorectal polyps in general or adanomatous polyps in particular in a subject.

In one aspect, the invention provides a method for assessing whether a subject has or is predisposed to developing CRC and/or colorectal polyps, said method comprising:
 (a) providing a urine sample from said subject;
 (b) obtaining a metabolite profile from said urine sample;
 (c) comparing said metabolite profile with a reference metabolite profile; and
 (d) assessing, based on said comparison in step (c), whether said subject has or is predisposed to developing CRC and/or colorectal polyps.

A further aspect of the invention relates to a method for identifying urine metabolites indicative of the presence or absence of CRC and/or colorectal polyps, said method comprising:
 (a) providing a urine sample from a subject;
 (b) obtaining a metabolite profile from said urine sample;
 (c) comparing said metabolite profile with a reference metabolite profile; and
 (d) identifying, based on said comparison in step (c), one or more metabolites in said metabolite profile that are indicative of the presence of or predisposition to in said subject of CRC and/or colorectal polyps.

A further aspect of the invention relates to a use of a urine metabolite profile comprising one or more of metabolites selected from the group consisting of:
 1,6-Anhydro-β-D-glucose, 1-Methylnicotinamide, 2-Hydroxyisobutyrate, 2-Oxoglutarate, 3-Aminoisobutyrate, 3-Hydroxybutyrate, 3-Hydroxyisovalerate, 3-Hydroxymandelate, 3-Hydroxyphenylacetate, 3-Indoxyl sulfate, 4-Hydroxyphenylacetate, Acetate, Acetone, Adipate, Alanine, Ascorbate, Asparagine, Benzoate, Betaine, Butyrate, Carnitine, Citrate, Creatine, Creatinine, Dimethylamine, Ethanol, Formate, Galactose, Glucose, Glutamine, Glycerol, Glycine, Glycolate, Guanidoacetate, Hippurate, Histidine, Hypoxanthine, Isoleucine, Lactate, Leucine, Lysine, Mannitol, Methanol, Methylguanidine, N,N-Dimethylglycine, O-Acetylcarnitine, Pantothenate, Propylene glycol, Pyroglutamate, Pyruvate, Serine, Succinate, Sucrose, Tartrate, Taurine, Threonine, Trigonelline, Trimethylamine, Trimethylamine N-oxide, Tyrosine, Uracil, Urea, Valine, Xylose, cis-Aconitate, β-Alanine, H-Methylhistidine, T-Methylhistidine and trans-Aconitate,
for assessing whether a subject has or is predisposed to developing CRC and/or colorectal polyps.

A further aspect of the invention relates to a kit for assessing whether a subject has or is predisposed to developing CRC and/or colorectal polyps, said kit comprising one or more reagents for detecting the presence and/or concentration and/or amount of one or more metabolites in a urine sample of a subject, and instructions for use of said kit for assessing whether a subject has or is predisposed to developing CRC and/or colorectal polyps.

A further aspect of the invention relates to a system comprising:
 (a) a CRC- and/or colorectal polyps-assessing apparatus including a control unit and a memory unit to assess a CRC state in a subject; and
 (b) an information communication terminal apparatus that provides data on the presence and/or concentration and/or amount of metabolites in a urine sample from the subject connected to each other communicatively, wherein the information communication terminal apparatus includes:

(a) a data sending unit that transmits the data on the presence and/or concentration and/or amount of metabolites in the sample to the CRC- and/or colorectal polyps-assessing apparatus; and (b) an assessment result-receiving unit that receives the assessment result of the CRC and/or colorectal polyps state of the subject transmitted from the CRC- and/or colorectal polyps-assessing apparatus, wherein the control unit of the CRC- and/or colorectal polyps-assessing apparatus includes:

(a) a data-receiving unit that receives the data on the metabolite concentration and/or amount of the sample transmitted from the information communication terminal apparatus;

(b) a discriminant value-calculating unit that calculates a discriminant value that is a value of multivariate discriminant, based on both the concentration and/or amount value of the metabolite in the sample received by the data-receiving unit and a multivariate discriminant with the concentration and/or amount of the metabolite as explanatory variable stored in the memory unit;

(c) a discriminant value criterion-assessing unit that assesses the CRC or colorectal polyps state in the subject, based on the discriminant value calculated by the discriminant value-calculating unit; and (d) an assessment result-sending unit that transmits the assessment result of the subject obtained by the discriminant value criterion-assessing unit to the information communication terminal apparatus.

A further aspect of the invention relates to a method for identifying and evaluating effectiveness of pharmaceutical agents and/or surgical treatments and/or physical treatments against CRC and/or colorectal polyps, said method comprising:

(a) providing a first urine sample from a subject having CRC or colorectal polyps;

(b) obtaining a metabolite profile from said first urine sample;

(c) administering one or more pharmaceutical candidates and/or performing one or more physical or surgical treatments to or on said subject;

(d) providing a second urine sample from said subject in step (c);

(e) obtaining a metabolite profile from said second urine sample;

comparing said metabolite profile obtained in steps (b) and (e) with a reference metabolite profile; and (g) assessing, based on said comparison in step (f), whether the one or more pharmaceutical candidates and/or treatments is effective against CRC and/or colorectal polyps.

BRIEF DESCRIPTION OF THE DRAWINGS

In the drawings, which illustrate embodiments of the invention by way of example only.

DETAILED DESCRIPTION

CRC and Colorectal Polyps

Figure 1:
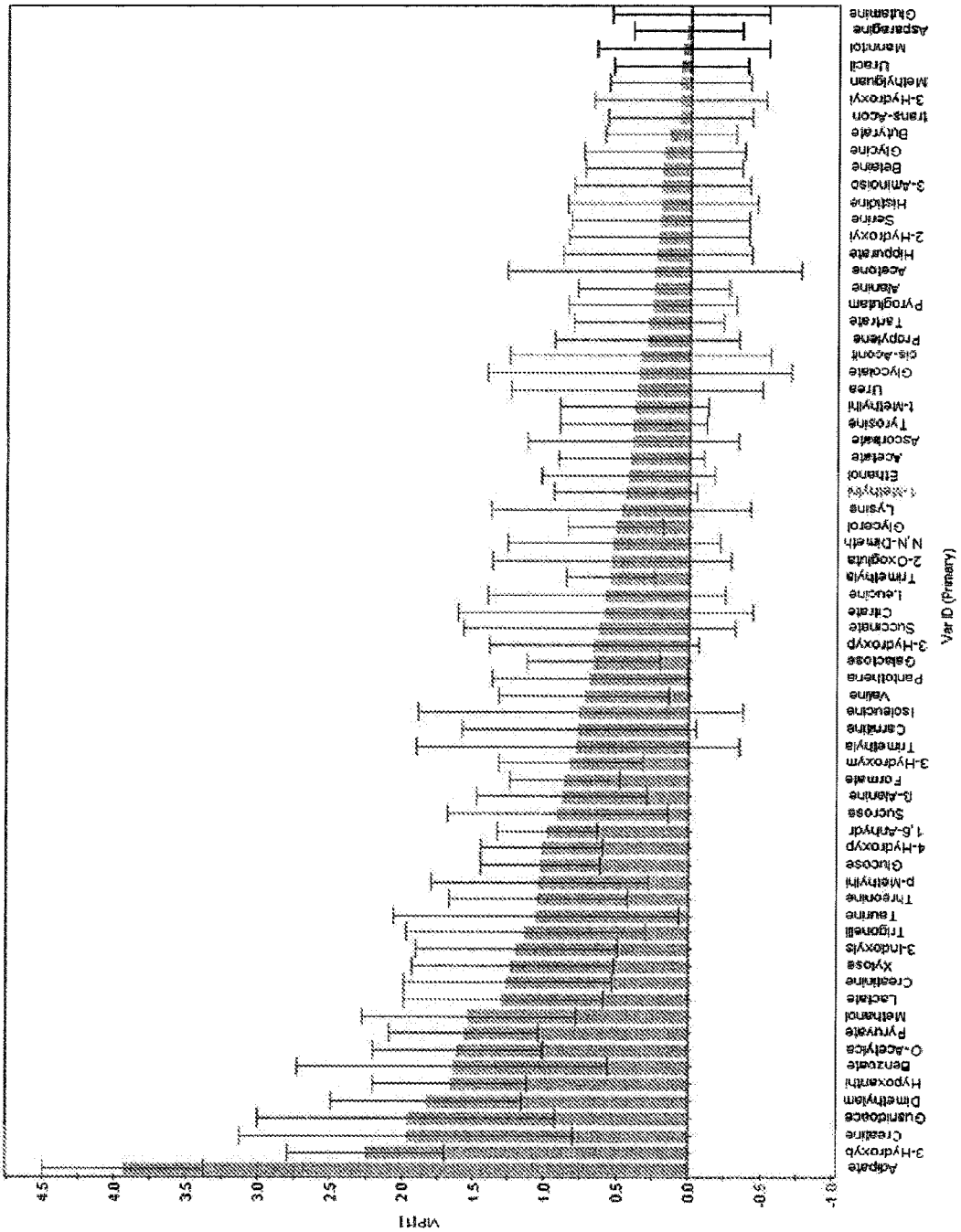
FIG. 1 is a variable importance in the projection (VIP) plot of analyzed metabolites in order of their contribution to the separation between data from urine samples obtained from subjects having CRC and that from subjects without CRC and/or colorectal polyps for 69 metabolites.

CRC is among the leading causes of morbidity. CRC is the third most common malignancy in the world, and represents approximately ten percent of the world's total cancer incidence. CRC appears not only in humans but also in animal species, and in both sexes. Among human beings, more than 9 out of 10 people diagnosed with CRC are over the age of 50. However, younger individuals can develop CRC.

The chance of surviving CRC is closely related to the stage of the disease at diagnosis. The likelihood of survival is greater if the diagnosis is made earlier, permitting earlier treatment. Adenomatous and some other types of colorectal polyps may progress to malignant carcinomas and may thus be indicative that a subject is at risk of developing CRC. Thus, not only is it beneficial to be able to detect CRC itself, it is useful to be able to detect also the presence of precancerous lesions such as colorectal polyps.

There are a number of types of colorectal polyps. Adenomatous polyps are known to be a precursor to full-blown CRC. Other types of polyps may not themselves have malignant potential. Nevertheless, they may be useful indicators that a subject is at risk of developing CRC. For instance, unlike adenomatous polyps, hyperplastic polyps have been historically recognized as benign growths of the colon that have no malignant potential—i.e. they were thought to be innocent bystanders. However, hyperplastic polyps have been noted to be more prevalent in populations with a higher incidence of cancer. Moreover, hyperplastic polyps may represent a heterogenous group of polyps, some of which have significant risk for malignant potential. These potentially malignant lesions are known as sessile serrated adenoma and have been linked to the microsatellite instability cancer pathway and thus are potential precursors of sporadic microsatellite unstable CRC.

Currently, the risk factors for CRC are not well understood and few specific risk factors other than diet have been established for the disease. As such, CRC is typically diagnosed from a complete subject history and physical examination, followed by endoscopic and/or radiological imaging. The diagnosis is confirmed with histopathological examination of biopsies or surgically removed specimens.

Current CRC screening methods consist of one or a combination of the followings: FOBT, flexible sigmoidoscopy, air-contrast barium enema, CTC and colonoscopy. These current screening methods all have limitations or potential risks that limit their application.

Colonoscopy is currently the standard test for assessing the presence or absence of CRC and/or colorectal polyps. However, colonoscopy is invasive and can impose unnecessary hazards and risks to an individual caused by sedation or the procedure itself, and complications with colonoscopy can include perforation, hemorrhage, respiratory depression, arrhythmias, and infection. In addition, it requires considerable physical resources and skilled personnel.

A known non-invasive CRC diagnostic method is FOBT. FOBT, however, has very low sensitivity in detection of CRC. FOBT is based on the assumption that cancers will bleed, therefore, can be detected in the stool using chemical or immunological assays, and involves a crude test for the peroxidase-like activity of heme in hemoglobin. However, the sensitivity of the test is only approximately 50%, with a 20% sensitivity for adenomas, due to the fact that not all adenomas and CRCs bleed. In addition, it is an unattractive test for subjects as the handling of fecal matter is required.

CTC, or virtual colonoscopy, is a recent non-invasive technique for imaging the colon. However, its performance varies due primarily to technological differences in the subject preparation and the hardware and software used for the analysis. Other limitations of CTC include high false positives (FP) readings, inability to detect flat adenomas, no capacity to remove polyps, repetitive and cumulative radiation doses, and cost.

With advances in the CRC related molecular pathology, several new screening methods based on DNA analysis from stool samples became available. These are typically PCR-based assays used to identify mutations known to occur in the adenoma-to-carcinoma sequence, or in familial CRC. Commonly screened gene mutations include KRAS, TP53, APC, as well as assays for micro satellite instability and hypermethylated DNA. However, whether genomics-based tests will result in high diagnostic accuracy for sporadic CRC remains to be seen.

Metabolomics and Diagnosis of CRC or Colorectal Polyps

Metabolomics is an emerging field of research downstream from genomics, proteomics and transcriptomics. A metabolome is a quantitative collection of low molecular weight compounds, such as metabolic substrates and products, lipids, small peptides, vitamins, and other protein cofactors, generated by metabolism. A metabolome is downstream from a transcriptome and a proteome and thus any changes from a normal state are amplified and are numerically more tractable. Metabolomics can be a precise, consistent, and quantitative tool to examine and describe cellular growth, maintenance, and function.

Metabolomics can be performed on urine, serum, tissue, and even on saliva and amniotic fluid. Generally, urine metabolomics represents a much less invasive method of testing compared to tissue or serum metabolomics.

The present invention uses urine metabolomics to identify subjects having or at risk of developing CRC and/or colorectal polyps. This is beneficial in the management of the risk of CRC and/or colorectal polyps, both in prevention and treatment. The use of urine metabolomics in the present invention has a number of potential benefits. Obtaining a urine sample and its analysis are relatively simple, non-invasive, and cost efficient compared to the existing methods for assessing presence or absence of CRC or colorectal polyps. The invention also permits monitoring of individual susceptibility to CRC prior to resorting to, or in combination with, conventional screening methods, and provides for population-based monitoring of CRC and/or colorectal polyps.

A wide range of analytical techniques to assay and quantitate components of a metabolome and to extract useful metabolite profiles from the data are available, including e.g. liquid and gas chromatography coupled with mass spectrometry (LCMS or GCMS), nuclear magnetic resonance (NMR) spectroscopy, high performance liquid chromatography (HPLC), thin layer chromatography (TLC), electrochemical analysis, refractive index spectroscopy, ultra-violet spectroscopy, fluorescent analysis, radiochemical analysis, near-infrared spectroscopy and light scattering analysis. The outputs from such analytical techniques can be further analyzed using multivariate analysis such as principal component analysis (PCA), partial least squares discriminant analysis (PLS-DA) and orthogonal partial least squares (OPLS).

One or more metabolite profiles obtained from the previously described analysis based on a reference population of known CRC and/or colorectal polyp status can be used as a reference to assess the presence or absence of CRC or colorectal polyps in a subject. For example, a reference population may be composed of healthy subjects (i.e. subjects known or assessed by other means to be free of CRC and/or colorectal polyps), or alternatively may be composed of subjects already identified to have or to be predisposed to developing CRC or colorectal polyps. This assessment can be performed by: (a) providing a urine sample from a subject that is suspected to have or be predisposed to developing CRC and/or colorectal polyps; (b) obtaining a metabolite profile from said urine sample; (c) comparing said metabolite profile with a reference metabolite profile; and (d) assessing, based on said comparison in step (c), whether said subject has or is predisposed to developing CRC and/or colorectal polyps.

Providing and Processing Urine Samples

Urine samples can be collected from subjects that are known or suspected to have CRC or colorectal polyps, and from subjects without CRC or colorectal polyps, by known protocols. The subjects of this invention include both sexes of animal species that are susceptible to CRC and/or colorectal polyps, including humans.

In addition to providing a urine sample, subjects can take a FOBT, fecal immune testing (FIT), and/or a colonoscopy, the results of which can be used to determine classification of subjects into one of the groups of: subjects without CRC and/or colorectal polyps (normal group); subjects having colorectal polyps in general (polyp group); or subjects having adenomatous polyps specifically (adenomatous group). Pathology of resected surgical specimens can be used as the standard to classify subjects into a group where subjects have CRC (CRC group). Relevant clinical information such as age, gender, family history, comorbidities, medications etc. can be obtained from study questionnaires and subjects' medical charts, which could also be used to determine classification of subjects. Such testing can be used in the development of reference urine metabolite profiles and can also be used as an adjunct to screening test subjects by the methods of the invention to confirm or further refine a diagnosis of CRC and/or colorectal polyps.

Urine samples can be collected from subjects any time, e.g. during routine screening or in connection with a regular check-up or visit to a physician, or prior to or together with administration of treatment, such as the administration of a medicine or performance of surgery. Urine samples can be collected one or more times for a separate or combined analysis, e.g. 15-700 ml each time. Urine sample collection containers can vary in size and shape, but ideally can accommodate e.g. 20-1,000 ml of urine sample. Typically, the container is sterile. If desired, sample containers can be pre-filled or treated with agents for preventing contamination of the sample by microorganisms such as bacteria and fungi while a sample is waiting to be stored, or such agents can be added after sample collection. Metabolomic analysis of the collected urine samples may occur immediately or the samples may be processed for storage and later analysis. For example, the whole or part of the sample could be stored in a freezer at −5~10° C. within 0~48 hours of collection, or could be frozen at −120~−10° C. within 0-48 hours of collection, or could be processed with chemicals for future analysis or use before being stored. If samples have been stored frozen, they may be thawed (e.g. at room temperature for 12-48 hours), prior to analysis.

Obtaining a Metabolite Profile from the Sample

The analytical techniques that make it possible to obtain metabolite profiles from the urine samples can include one or a combination of, but not limited to, mass spectrometry (MS) coupled with gas chromatography (GCMS) or liquid chromatography (LCMS), HPLC, NMR spectroscopy, TLC, electrochemical analysis, refractive index spectroscopy, ultra-violet spectroscopy, fluorescent analysis, radiochemical analysis, near-infrared spectroscopy and light scattering analysis. The outputs obtained from such analyses can be further analyzed using multivariate statistical analysis to aid in the characterization of differences of metabolite profile between samples related to CRC or colorectal polyps. Such analytical tools include, but are not limited to, principal component analysis (PCA), partial least squares discriminant analysis (PLS-DA) and orthogonal partial least squares (OPLS). Though HPLC or technologies involving MS can be used for measuring metabolite concentrations in the sub-molar range, they are often laborious and time consuming as they require that chromatography (liquid or gas) to separate the metabolites be done first, and also require multiple internal standards.

NMR spectroscopy is an ideal tool for metabolonomics study because it can quantify a large number of metabolites simultaneously, requires only one standard, and is generally faster to yield statistical analysis results such as PCA and/or OPLS plots.

In some embodiments, urine samples may be processed prior to analysis. For example, for non-automated (manual) NMR acquisition, about 100-1,000 µL urine sample can be taken from the collected and/or stored sample, then diluted with an internal standard at a ratio of e.g. 1:1-1:20 (v/v). The internal standard can include e.g. 1-20 mM of sodium 2,2-dimethyl-2-silapentane-5-sulfonate (DSS) or its salt form, 4,4-Dimethyl-4-silapentane-1-ammonium trifluoroacetate (DSA), or Trimethylsilyl propionate (TSP). Agents for preventing microbial contamination can also be added. Such additions can include e.g. 10-200 mM imidazole, or 0.1-0.5% or 0.5-5 µM of sodium azide. The total volume can be e.g. 100-1,300 µL. The sample for NMR analysis can be stored in a freezer at e.g. 1-6° C. The same process applies to the automated (robotic) NMR acquisition. On the day of NMR acquisition, the pH of each sample is measured. Various concentrations of acids and bases, for example, but not limited to, HCl and NaOH, can be added to the samples to achieve a pH between e.g. 6.7 and 6.8 to minimize chemical exchange as the chemical shift can change with pH. An aliquot of e.g. 100-1,000 µL of the samples can be placed in NMR tubes and capped for the samples for both non-automated and the automated NMR.

One-dimensional NMR spectra can be acquired. After the spectra are obtained, the pH of each sample can be rechecked to ensure that the pH has not shifted a significant amount. This data can be recorded to be referenced if a particular sample would produce an unexpected spectrum. Samples can be frozen and stored again at a sub-zero temperature.

Identification of Metabolites for a Reference Metabolite Profile

The present invention involves the discovery that metabolite profiles in the urine of subjects having or predisposed to developing CRC and/or colorectal polyps can be reliably distinguished from metabolite profiles in the urine of healthy subjects (i.e. those without CRC and/or colorectal polyps) such that this distinction can be used to assess whether a particular subject has or is predisposed to developing CRC and/or colorectal polyps. One or more reference profiles concerning metabolites present in the urine of a reference population known either to be free of CRC and/or colorectal polyps or to have or be predisposed to developing CRC or colorectal polyps is developed, which can then be used for comparison against a corresponding metabolite profile generated from the urine of a test subject. By analyzing the metabolite content of urine of subjects of known CRC or colorectal polyp status, it is then possible to compare this to the content of the same metabolites in subjects of a different CRC or colorectal polyp status, thus identifying metabolites which correlate significantly with the CRC or colorectal polyp status of an individual. In the illustrative examples herein, 240 metabolites were considered and 69 found to be of particular significance. However, urine contains thousands of metabolites, and the techniques described can be employed to assess whether other urine metabolites are similarly diagnostic of CRC and/or colorectal polyps.

Thus, in one aspect, the invention provides a method for identifying urine metabolites indicative of the presence or absence of CRC and/or colorectal polyps, the method comprising: (a) providing a urine sample from a subject; (b) obtaining a metabolite profile from the urine sample; (c) comparing the metabolite profile with a reference metabolite profile; and (d) identifying, based on the comparison in step (c), one or more metabolites in the metabolite profile that are indicative of the presence of or predisposition to in said subject of colorectal cancer and/or colorectal polyps.

Quantification of metabolites, e.g. by concentration or in absolute amount, can be done once the analysis data is available from, for example, but not limited to, GCMS, LCMS, HPLC, NMR spectroscopy, TLC, electrochemical analysis, refractive index spectroscopy, ultra-violet spectroscopy, fluorescent analysis, radiochemical analysis, near-infrared spectroscopy and light scattering analysis. The quantification data can be used to identify and to set a standard to determine a reference metabolite profile based on urine samples obtained from subjects known to be free of CRC and/or colorectal polyps.

For example, once the spectra are acquired from NMR spectroscopy, quantification of metabolites can be done using tools that compare the integral of a known reference signal, such as DSS, DSA or TSP, with signals derived from a library of compounds to determine concentration relative to the reference signal. The tools can include softwares such as Chenomx NMRSuite v4.6 software. The quantification process can be done by more than one individual for reading and verification to optimize accuracy.

Levels of the specific metabolites over or below a determined critical value, either in concentration or in amount, can indicate the presence of CRC or colorectal polyps in general or adenomatous polyps in particular. The concentrations or the amount of the metabolites can be interpreted independently using an individual cut-off for each metabolite or they can be interpreted collectively. Metabolite concentrations or amounts obtained can be used as they are (i.e. as the raw data) or be normalized. For example, the concentration or amount of a metabolite can be log-transformed to normalize the concentrations or amounts to the concentration or the amount of other metabolites. The metabolites can also be normalized to the concentration of all metabolites minus the concentration of selected compounds such as e.g. urea to obtain similar results.

Those metabolites which are not products of normal metabolism of a subject (e.g. xenobiotics such as ibuprofen and salicylurate) or internal standards (e.g. DSS) can be excluded in the analysis.

Multivariate statistical analysis can be applied to the collected data or complex spectral data to identify differences arising between the groups of data sets obtained from the urine sample. The metabolite measurements in samples from subject having CRC or colorectal polyps in general or adenomatous polyps specifically can be compared to metabolite measurements in samples from subjects without CRC or colorectal polyps to identify metabolites that significantly contribute to the separation of different groups. Data comparison can be performed using any appropriate tools that fulfill the purpose. The tools include PCA, PLS-DA, OPLS and support vector machines (SVM), and softwares that can perform one or more of such analyses, e.g., Simca-P+, can be used. These are statistical methods of compressing multidimensional data down to two or three main components. PLS-DA and OPLS are supervised, that is, they take into account the class assignments, while PCA is unsupervised and can be influenced by many factors such as gender, comorbidities etc.

An optimized multivariate cut-off for the underlying combination of metabolites can be used to discriminate a cancerous or pre-cancerous state from a healthy state. Upon determination of which specific metabolites are the significant contributors to the data separation between the CRC group and the normal group samples or the polyp group and the normal group samples or the adenoma group and the normal group samples, one or more profiles of these specific metabolites can be established. One or more metabolite profiles or its combination can be used as a reference metabolite profile to assess CRC or colorectal polyps in general or adenomatous polyps in particular in a subject.

In some embodiments, metabolites that were significant in separating normal group from CRC group, normal group from polyp group, and normal group from adenoma group were identified as: 1,6-Anhydro-β-D-glucose; 1-Methylnicotinamide; 2-Hydroxyisobutyrate; 2-Oxoglutarate; 3-Aminoisobutyrate; 3-Hydroxybutyrate; 3-Hydroxyisovalerate; 3-Hydroxymandelate; 3-Hydroxyphenylacetate; 3-Indoxyl sulfate; 4-Hydroxyphenylacetate; Acetate; Acetone; Adipate; Alanine; Ascorbate; Asparagine; Benzoate; Betaine; Butyrate; Carnitine; Citrate; Creatine; Creatinine; Dimethylamine; Ethanol; Formate; Galactose; Glucose; Glutamine; Glycerol; Glycine; Glycolate; Guanidoacetate; Hippurate; Histidine; Hypoxanthine; Isoleucine; Lactate; Leucine; Lysine; Mannitol; Methanol; Methylguanidine; N,N-Dimethylglycine; O-Acetylcarnitine; Pantothenate; Propylene glycol; Pyroglutamate; Pyruvate; Serine; Succinate; Sucrose; Tartrate; Taurine; Threonine; Trigonelline; Trimethylamine; Trimethylamine N-oxide; Tyrosine; Uracil; Urea; Valine; Xylose; cis-Aconitate; β-Alanine; Π-Methylhistidine; T-Methylhistidine; and trans-Aconitate.

However, not all features of the metabolite analysis results are always required for a proper diagnosis of CRC, colorectal polyps in general or adenomatous polyps specifically. Since there would be an incremental cost to obtaining more information about a subject's urine metabolite profile, it may be beneficial to use the minimal number of metabolites possible. In order to determine which specific metabolites are the strongest contributors to the data separation between the CRC group and the normal group samples or the polyp group and the normal group samples or the adenoma group and the normal group samples, further data analysis can be performed. This further data analysis could be made by an appropriate analytical method such as, but not limited to, a VIP plot.

The VIP plot allows identification of metabolites that have a greater impact on driving the separation between groups in models. Each metabolite used to construct models can be assigned a VIP score. This score is assigned through a statistical formula that is used to calculate the influence of each metabolite. The higher the VIP score, the greater the influence of the metabolite with the score on separating different groups. The VIP plot also allows for the comparison of the influence of one metabolite to another's. In VIP plot analysis, factors with a large VIP, usually greater than 1, are said to be the most relevant. Metabolites with a VIP value higher than 1 can be the strongest contributors, and all or part of them can constitute a reference metabolite profile once its capability of assessing CRC or colorectal polyps is successfully demonstrated thorough a comparison with the reference metabolite profile consisting of all the metabolites found significant in the separation of different groups.

There are many ways to evaluate a selected metabolite profile to assess whether a subject has or is predisposed to developing CRC and/or colorectal polyps. The values measured for metabolites can be mathematically combined and the combined value can be correlated to the underlying diagnostic question. Metabolite values may be combined by any appropriate mathematical method. Mathematical methods for correlating a metabolite combination to a disease can employ methods such as, but not limited to, discriminant analysis (DA) (i.e. linear-, quadratic-, regularized-DA), Kernel Methods (i.e. SVM), Nonparametric Methods (i.e. k-Nearest-Neighbor Classifiers), PLS (Partial Least Squares), Tree-Based Methods (i.e. Logic Regression, CART, Random Forest Methods, Boosting/Bagging Methods), Generalized Linear Models (i.e. Logistic Regression), Principal Components based Methods (i.e. SIMCA), Generalized Additive Models, Fuzzy Logic based Methods, Neural Networks and Genetic Algorithms based Methods. For the SVM model, the linear coefficients of each feature in an SVM classifier can be used to select the most important features. Those features that had the largest absolute value can be selected, and the SVM model can be re-calculated using only the selected features and the training set if necessary.

When comparing test results from two different populations, for example, one with a disease and the other without the disease, a perfect separation between the two groups is rarely observed. Indeed, the distribution of the test results will overlap. Therefore, when a cut-off point or criterion value to discriminate between the two populations is selected and applied, there will be some cases with the disease correctly classified as positive (True Positive fraction), but some cases with the disease will be classified negative (False Negative fraction). On the other hand, some cases without the disease will be correctly classified as negative (True Negative fraction), but some cases without the disease will be classified as positive (False Positive fraction).

The diagnostic performance of such a test, or the accuracy of a test to discriminate diseased groups from healthy groups, can be evaluated using tools such as ROC curve analysis. The ROC curve is a graphical representation of the spectrum of sensitivities and specificities generated using the various cut-offs, using the sensitivity as the y-axis and 1-specificity as the x-axis. In an ROC curve the true positive rate (Sensitivity) is plotted in function of the FP rate (100-Specificity) for different cut-off points. Each point on the ROC curve represents a sensitivity/specificity pair corresponding to a particular decision threshold. A test with perfect discrimination (no overlap in the two distributions) has a ROC curve that passes through the upper left corner (100% sensitivity, 100% specificity). Therefore, qualitatively, the closer the plot is to the upper left corner, the higher the overall accuracy of the test. Area under the ROC curve (AUC) reflects the accuracy of the test and is displayed on the left lower corner of the plot. An AUC of 0.9 to 1 represents an excellent diagnostic test whereas an AUC of 0.8-0.9 represents a good test and an AUC of 0.7 to 0.8 represents a fair test.

Development of Reference Metabolite Profiles

Generally, the more metabolites that are assessed, the more accurate will be the assessment of CRC and/or colorectal polyps. In exemplary embodiments, more than 240 metabolites were considered, and 69 metabolites were used to assess whether a subject has or is predisposed to developing CRC or colorectal polyps. Indeed, other, or additional urine metabolites beyond these metabolites identified can be included in the metabolite profile. However, as noted above, this involves greater effort and cost. In many instances, a less accurate, specific, or detailed assessment may be sufficient, particularly if the assessment is only preliminary in nature, or is to be conducted together with or followed by another diagnostic test, such as colonoscopy. Further, a test involving the assessment of fewer metabolites may be more readily reduced to a simplified kit or test that can be used by a subject at home, or by a medical practitioner at the point of care, without need for sending a urine sample to a laboratory for analysis.

As explained above, VIP values greater than 1 are considered to reflect metabolites with the greatest potential for discriminating between healthy and diseased subjects. For the assessment of CRC per se, as distinct from colorectal polyps of any kind, as detailed in Table 1, the following metabolites, have been shown to exhibit VIP values greater than 1.0, presented from highest to lowest VIP value: adipate; 3-hydroxybutyrate; creatine; guanidoacetate; dimethylamine; hypoxanthine; benzoate; O-acetylcarnitine; pyruvate; methanol; lactate; creatinine; xylose; 3-indoxylsulfate; trigonelline; taurine; threonine; p-methylhistidine; glucose; and 4-hydroxyphenylacetate.

In an embodiment, the reference metabolic profile is directed to assessing whether a subject has or is predisposed to developing CRC, and includes measurements of concentrations in a urine sample of at least any 1, 2, 3, 4, 5, 6, 7, 8, 9, 10, 11, 12, 13, 14, 15, 16, 17, 18, 19 or 20 metabolites selected from the group consisting of: adipate; 3-hydroxybutyrate; creatine; guanidoacetate; dimethylamine; hypoxanthine; benzoate; O-acetylcarnitine; pyruvate; methanol; lactate; creatinine; xylose; 3-indoxylsulfate; trigonelline; taurine; threonine; p-methylhistidine; glucose; and 4-hydroxyphenylacetate.

Generally, if fewer than all 20 of these metabolites are to be used in the reference metabolite profile, preference will be given to those with the highest VIP values. As described in Table 2, a profile containing only the top five metabolites was demonstrated to have acceptable sensitivity and specificity, and fewer may be used to develop an acceptable profile. Thus, in various embodiments, the reference profile for detecting CRC includes one or more metabolites in a set of metabolites selected from the group consisting of:

(i) adipate; 3-hydroxybutyrate; creatine; guanidoacetate; dimethylamine; hypoxanthine; benzoate; O-acetylcarnitine; pyruvate; methanol; lactate; creatinine; xylose; 3-indoxylsulfate; trigonelline; taurine; threonine; p-methylhistidine; glucose; and 4-hydroxyphenylacetate;

(ii) adipate; 3-hydroxybutyrate; creatine; guanidoacetate; dimethylamine; hypoxanthine; benzoate; O-acetylcarnitine; pyruvate; methanol; lactate; creatinine; xylose; 3-indoxylsulfate; trigonelline; taurine; threonine; p-methylhistidine; and glucose;

(iii) adipate; 3-hydroxybutyrate; creatine; guanidoacetate; dimethylamine; hypoxanthine; benzoate; O-acetylcarnitine; pyruvate; methanol; lactate; creatinine; xylose; 3-indoxylsulfate; trigonelline; taurine; threonine; and p-methylhistidine;

(iv) adipate; 3-hydroxybutyrate; creatine; guanidoacetate; dimethylamine; hypoxanthine; benzoate; O-acetylcarnitine; pyruvate; methanol; lactate; creatinine; xylose; 3-indoxylsulfate; trigonelline; taurine; and threonine (v) adipate; 3-hydroxybutyrate; creatine; guanidoacetate; dimethylamine; hypoxanthine; benzoate; O-acetylcarnitine; pyruvate; methanol; lactate; creatinine; xylose; 3-indoxylsulfate; trigonelline; and taurine;

(vi) adipate; 3-hydroxybutyrate; creatine; guanidoacetate; dimethylamine; hypoxanthine; benzoate; O-acetylcarnitine; pyruvate; methanol; lactate; creatinine; xylose; 3-indoxylsulfate; and trigonelline;

(vii) adipate; 3-hydroxybutyrate; creatine; guanidoacetate; dimethylamine; hypoxanthine; benzoate; O-acetylcarnitine; pyruvate; methanol; lactate; creatinine; xylose; and 3-indoxylsulfate;

(viii) adipate; 3-hydroxybutyrate; creatine; guanidoacetate; dimethylamine; hypoxanthine; benzoate; O-acetylcarnitine; pyruvate; methanol; lactate; creatinine; and xylose;

(vix) adipate; 3-hydroxybutyrate; creatine; guanidoacetate; dimethylamine; hypoxanthine; benzoate; O-acetylcarnitine; pyruvate; methanol; lactate; and creatinine;

(x) adipate; 3-hydroxybutyrate; creatine; guanidoacetate; dimethylamine; hypoxanthine; benzoate; O-acetylcarnitine; pyruvate; methanol; and lactate;

(xi) adipate; 3-hydroxybutyrate; creatine; guanidoacetate; dimethylamine; hypoxanthine; benzoate; O-acetylcarnitine; pyruvate; and methanol;

(xii) adipate; 3-hydroxybutyrate; creatine; guanidoacetate; dimethylamine; hypoxanthine; benzoate; O-acetylcarnitine; and pyruvate;

(xiii) adipate; 3-hydroxybutyrate; creatine; guanidoacetate; dimethylamine; hypoxanthine; benzoate; and O-acetylcarnitine;

(xiv) adipate; 3-hydroxybutyrate; creatine; guanidoacetate; dimethylamine; hypoxanthine; and benzoate;

(xv) adipate; 3-hydroxybutyrate; creatine; guanidoacetate; dimethylamine; and hypoxanthine;

(xvi) adipate; 3-hydroxybutyrate; creatine; guanidoacetate; and dimethylamine;

(xvii) adipate; 3-hydroxybutyrate; creatine; and guanidoacetate;

(xviii) adipate; 3-hydroxybutyrate; and creatine;

(xix) adipate and 3-hydroxybutyrate; and (xx) adipate.

In some embodiments of the invention, it is the concentration (e.g. measured in $\mu M$) of the urine metabolites that is measured, and a higher or lower concentration of the metabolite in the urine of a test subject relative to that in reference metabolite profile (based either on raw or normalized concentrations) is indicative of CRC.

In some embodiments, an elevated concentration of any one or more metabolites selected from the group consisting of adipate; 3-hydroxybutyrate; creatine; guanidoacetate; dimethylamine; benzoate; O-acetylcarnitine; lactate; xylose; 3-indoxylsulfate; trigonelline; taurine; threonine; p-methylhistidine and 4-hydroxyphenylacetate is indicative that the subject has or is predisposed to developing CRC.

It will be understood that by "elevated" it is meant that the concentration of a metabolite in the urine of a subject that has or is predisposed to developing CRC is higher than in the urine of subjects that do not have or are not predisposed to CRC. For instance, referring to Table 1, it will be seen that the mean concentration of adipate in the urine of individuals with CRC was 218.1 $\mu M$, much higher than the mean concentration of adipate in the urine of "normal" subjects without CRC, which was found to be 1.3 $\mu M$. Thus, on a comparative basis relative to healthy subjects, subjects with CRC had elevated adipate concentrations in their urine.

In some embodiments, a reduced concentration of any one or more metabolites selected from the group consisting of hypoxanthine; pyruvate; methanol; creatinine and glucose is indicative that the subject has or is predisposed to developing CRC.

It will be understood that by "reduced" it is meant that the concentration of a metabolite in the urine of a subject that has or is predisposed to developing CRC is lower than in the urine of subjects that do not have or are not predisposed to CRC. For instance, referring to Table 1, it will be seen that the mean concentration of hypoxanthine in the urine of subjects with CRC was 188.4 µM, lower than the mean concentration of hypoxanthine in the urine of "normal" subjects without CRC, which was found to be 208.4 µM. Thus, on a comparative basis relative to healthy subjects, subjects with CRC had reduced hypoxanthine concentrations in their urine.

A reference metabolite profile that is diagnostic of colorectal polyps may be different than a reference metabolite profile for CRC per se. That is, the reference diagnostic profile may be made up of a different set of relevant metabolites, and different relative concentrations of these metabolites may be relevant.

In certain embodiments, the reference metabolite profile is for adenomatous polyps and includes concentrations of at least any 1, 2, 3, 4, 5, 6, 7, 8, 9, 10, 11, 12, 13, 14, 15, 16 or 17 metabolites selected from the group consisting of: butyrate; serine; methanol; β-alanine; p-methylhistidine; 3-hydroxybutyrate; asparagine; trigonelline; 3-hydroxyphenylacetate; histidine; acetone; 2-oxoglutarate; ethanol; adipate; 3-hydroxymandelate; tyrosine and benzoate.

As above, these are metabolites found to have VIP scores of 1.0 or above and are listed in descending order in Table 5. As above, acceptable specificity and sensitivity was demonstrated with a profile based on only the top five metabolites (Table 6) and fewer may be used. Thus, if fewer than all of the metabolites are included in the reference metabolite profile, the profile may include one or more metabolites in a set of metabolites selected from the group consisting of:

(i) butyrate; serine; methanol; β-alanine; p-methylhistidine; 3-hydroxybutyrate; asparagine; trigonelline; 3-hydroxyphenylacetate; histidine; acetone; 2-oxoglutarate; ethanol; adipate; 3-hydroxymandelate; tyrosine and benzoate;

(ii) butyrate; serine; methanol; β-alanine; p-methylhistidine; 3-hydroxybutyrate; asparagine; trigonelline; 3-hydroxyphenylacetate; histidine; acetone; 2-oxoglutarate; ethanol; adipate; 3-hydroxymandelate and tyrosine;

(iii) butyrate; serine; methanol; β-alanine; p-methylhistidine; 3-hydroxybutyrate; asparagine; trigonelline; 3-hydroxyphenylacetate; histidine; acetone; 2-oxoglutarate; ethanol; adipate and 3-hydroxymandelate;

(iv) butyrate; serine; methanol; β-alanine; p-methylhistidine; 3-hydroxybutyrate; asparagine; trigonelline; 3-hydroxyphenylacetate; histidine; acetone; 2-oxoglutarate; ethanol and adipate;

(v) butyrate; serine; methanol; β-alanine; p-methylhistidine; 3-hydroxybutyrate; asparagine; trigonelline; 3-hydroxyphenylacetate; histidine; acetone; 2-oxoglutarate and ethanol;

(vi) butyrate; serine; methanol; β-alanine; p-methylhistidine; 3-hydroxybutyrate; asparagine; trigonelline; 3-hydroxyphenylacetate; histidine; acetone and 2-oxoglutarate;

(vii) butyrate; serine; methanol; β-alanine; p-methylhistidine; 3-hydroxybutyrate; asparagine; trigonelline; 3-hydroxyphenylacetate; histidine; and acetone;

(viii) butyrate; serine; methanol; β-alanine; p-methylhistidine; 3-hydroxybutyrate; asparagine; trigonelline; 3-hydroxyphenylacetate and histidine;

(ix) butyrate; serine; methanol; β-alanine; p-methylhistidine; 3-hydroxybutyrate; asparagine; trigonelline and 3-hydroxyphenylacetate;

(x) butyrate; serine; methanol; β-alanine; p-methylhistidine; 3-hydroxybutyrate; asparagine and trigonelline;

(xi) butyrate; serine; methanol; β-alanine; p-methylhistidine; 3-hydroxybutyrate and asparagine;

(xii) butyrate; serine; methanol; β-alanine; p-methylhistidine; and 3-hydroxybutyrate;

(xiii) butyrate; serine; methanol; β-alanine and p-methylhistidine;

(xiv) butyrate; serine; methanol and β-alanine;

(xv) butyrate; serine and methanol;

(xvi) butyrate and serine; and (xvii) butyrate.

In some embodiments, an elevated concentration of any one or more metabolites selected from the group consisting of p-methylhistidine; 3-hydroxybutyrate; asparagine; trigonelline; 3-hydroxyphenylacetate; histidine; acetone; adipate; 3-hydroxymandelate; tyrosine and benzoate is indicative that the subject has or is predisposed to developing adenomatous polyps. As above, "elevated" is relative to a corresponding urine metabolite concentration of healthy subjects.

In some embodiments, a reduced concentration of any one or more metabolites selected from the group consisting of butyrate; serine; methanol; β-alanine; 2-oxoglutarate and ethanol is indicative that the subject has or is predisposed to developing adenomatous polyps. As above, "reduced" is relative to a corresponding urine metabolite concentration of healthy subjects.

Elevated and reduced urine metabolite concentrations for subjects having adenomatous polyps are shown in Table 5.

In some embodiments, the reference metabolite profile is designed to identify subjects having or predisposed to colorectal polyps, but not necessarily to distinguish one type of polyp from another. For instance, the polyp may be adenomatous or hyperplastic, but the reference diagnostic profile does not necessarily distinguish between the two.

In certain embodiments, the reference metabolite profile is for colorectal polyps that are either adenomatous polyps or hyperplastic polyps and includes urine concentrations of at least any 1, 2, 3, 4, 5, 6, 7, 8, 9, 10, 11, 12, 13, 14, 15, 16, 17, 18, 19, 20, 21, 22, 23, 24, 25 or 26 metabolites selected from the group consisting of: butyrate; serine; asparagine; p-methylhistidine; 3-hydroxybutyrate; methanol; 3-hydroxymandelate; tyrosine; trigonelline; β-alanine; histidine; dimethylamine; urea; 1,6-anhydro-β-D-glucose; glucose; ethanol; benzoate; acetone; threonine; 2-hydroxyisobutyrate; creatinine; 3-hydroxyphenylacetate; 3-indoxylsulfate; hippurate; ascorbate; and 4-hydroxyphenylacetate.

As above, these are metabolites found to have VIP scores of 1.0 or above and are listed in descending order (Table 3). As above, acceptable specificity and sensitivity was demonstrated with a profile based on only the top five metabolites (Table 4) and fewer may be used. Thus, if fewer than all of the metabolites are included in the reference metabolite profile, the profile may include one or more metabolites in a set of metabolites selected from the group consisting of:

(i) butyrate; serine; asparagine; p-methylhistidine; 3-hydroxybutyrate; methanol; 3-hydroxymandelate; tyrosine; trigonelline; β-alanine; histidine; dimethylamine; urea; 1,6-anhydro-β-D-glucose; glucose; ethanol; benzoate; acetone;

threonine; 2-hydroxyisobutyrate; creatinine; 3-hydroxyphenylacetate; 3-indoxylsulfate; hippurate; ascorbate; and 4-hydroxyphenylacetate;

(ii) butyrate; serine; asparagine; p-methylhistidine; 3-hydroxybutyrate; methanol; 3-hydroxymandelate; tyrosine; trigonelline; β-alanine; histidine; dimethylamine; urea; 1,6-anhydro-β-D-glucose; glucose; ethanol; benzoate; acetone; threonine; 2-hydroxyisobutyrate; creatinine; 3-hydroxyphenylacetate; 3-indoxylsulfate; hippurate and ascorbate;

(iii) butyrate; serine; asparagine; p-methylhistidine; 3-hydroxybutyrate; methanol; 3-hydroxymandelate; tyrosine; trigonelline; β-alanine; histidine; dimethylamine; urea; 1,6-anhydro-β-D-glucose; glucose; ethanol; benzoate; acetone; threonine; 2-hydroxyisobutyrate; creatinine; 3-hydroxyphenylacetate; 3-indoxylsulfate and hippurate;

(iv) butyrate; serine; asparagine; p-methylhistidine; 3-hydroxybutyrate; methanol; 3-hydroxymandelate; tyrosine; trigonelline; β-alanine; histidine; dimethylamine; urea; 1,6-anhydro-β-D-glucose; glucose; ethanol; benzoate; acetone; threonine; 2-hydroxyisobutyrate; creatinine; 3-hydroxyphenylacetate and 3-indoxylsulfate;

(v) butyrate; serine; asparagine; p-methylhistidine; 3-hydroxybutyrate; methanol; 3-hydroxymandelate; tyrosine; trigonelline; β-alanine; histidine; dimethylamine; urea; 1,6-anhydro-β-D-glucose; glucose; ethanol; benzoate; acetone; threonine; 2-hydroxyisobutyrate; creatinine and 3-hydroxyphenylacetate;

(vi) butyrate; serine; asparagine; p-methylhistidine; 3-hydroxybutyrate; methanol; 3-hydroxymandelate; tyrosine; trigonelline; β-alanine; histidine; dimethylamine; urea; 1,6-anhydro-β-D-glucose; glucose; ethanol; benzoate; acetone; threonine; 2-hydroxyisobutyrate and creatinine;

(vii) butyrate; serine; asparagine; p-methylhistidine; 3-hydroxybutyrate; methanol; 3-hydroxymandelate; tyrosine; trigonelline; β-alanine; histidine; dimethylamine; urea; 1,6-anhydro-β-D-glucose; glucose; ethanol; benzoate; acetone; threonine and 2-hydroxyisobutyrate;

(viii) butyrate; serine; asparagine; p-methylhistidine; 3-hydroxybutyrate; methanol; 3-hydroxymandelate; tyrosine; trigonelline; β-alanine; histidine; dimethylamine; urea; 1,6-anhydro-β-D-glucose; glucose; ethanol; benzoate; acetone and threonine;

(vix) butyrate; serine; asparagine; p-methylhistidine; 3-hydroxybutyrate; methanol; 3-hydroxymandelate; tyrosine; trigonelline; β-alanine; histidine; dimethylamine; urea; 1,6-anhydro-β-D-glucose; glucose; ethanol; benzoate and acetone;

(x) butyrate; serine; asparagine; p-methylhistidine; 3-hydroxybutyrate; methanol; 3-hydroxymandelate; tyrosine; trigonelline; β-alanine; histidine; dimethylamine; urea; 1,6-anhydro-β-D-glucose; glucose; ethanol and benzoate;

(xi) butyrate; serine; asparagine; p-methylhistidine; 3-hydroxybutyrate; methanol; 3-hydroxymandelate; tyrosine; trigonelline; β-alanine; histidine; dimethylamine; urea; 1,6-anhydro-β-D-glucose; glucose and ethanol;

(xii) butyrate; serine; asparagine; p-methylhistidine; 3-hydroxybutyrate; methanol; 3-hydroxymandelate; tyrosine; trigonelline; β-alanine; histidine; dimethylamine; urea; 1,6-anhydro-β-D-glucose and glucose;

(xiii) butyrate; serine; asparagine; p-methylhistidine; 3-hydroxybutyrate; methanol; 3-hydroxymandelate; tyrosine; trigonelline; β-alanine; histidine; dimethylamine; urea and 1,6-anhydro-β-D-glucose;

(xiv) butyrate; serine; asparagine; p-methylhistidine; 3-hydroxybutyrate; methanol; 3-hydroxymandelate; tyrosine; trigonelline; β-alanine; histidine; dimethylamine and urea;

(xv) butyrate; serine; asparagine; p-methylhistidine; 3-hydroxybutyrate; methanol; 3-hydroxymandelate; tyrosine; trigonelline; β-alanine; histidine and dimethylamine;

(xvi) butyrate; serine; asparagine; p-methylhistidine; 3-hydroxybutyrate; methanol; 3-hydroxymandelate; tyrosine; trigonelline; β-alanine and histidine;

(xvii) butyrate; serine; asparagine; p-methylhistidine; 3-hydroxybutyrate; methanol; 3-hydroxymandelate; tyrosine; trigonelline and β-alanine;

(xviii) butyrate; serine; asparagine; p-methylhistidine; 3-hydroxybutyrate; methanol; 3-hydroxymandelate; tyrosine and trigonelline;

(xix) butyrate; serine; asparagine; p-methylhistidine; 3-hydroxybutyrate; methanol; 3-hydroxymandelate and tyrosine;

(xx) butyrate; serine; asparagine; p-methylhistidine; 3-hydroxybutyrate; methanol and 3-hydroxymandelate;

(xxi) butyrate; serine; asparagine; p-methylhistidine; 3-hydroxybutyrate and methanol;

(xxii) butyrate; serine; asparagine; p-methylhistidine and 3-hydroxybutyrate;

(xxiii) butyrate; serine; asparagine and p-methylhistidine;

(xxiv) butyrate; serine and asparagine;

(xxv) butyrate and serine; and (xxvi) butyrate.

In some embodiments, an elevated concentration of any one or more metabolites selected from the group consisting of asparagine; p-methylhistidine; 3-hydroxybutyrate; 3-hydroxymandelate; tyrosine; trigonelline; histidine; dimethylamine; urea; 1,6-anhydro-β-D glucose; glucose; benzoate; acetone; threonine; 2-hydroxyisobutyrate; creatinine; 3-hydroxyphenylacetate; 3-indoxylsulfate; hippurate; and 4-hydroxyphenylacetate is indicative that the subject has or is predisposed to developing colorectal polyps which are either adenomatous polyps or hyperplastic polyps. As above, "elevated" is relative to a corresponding urine metabolite concentration of healthy individuals.

In some embodiments, a reduced concentration of any one or more metabolites selected from the group consisting of butyrate; serine; methanol; β-alanine; ethanol and ascorbate is indicative that the subject has or is predisposed to developing colorectal polyps which are either adenomatous polyps or hyperplastic polyps. As above, "reduced" is relative to a corresponding urine metabolite concentration of healthy subjects.

Elevated and reduced urine metabolite concentrations for subjects having polyps that are either adenomatous or hyperplastic are shown in Table 3.

Assessing Whether a Subject has or is Predisposed to Developing CRC and/or Colorectal Polyps The invention provides methods for assessing whether a subject has or is predisposed to developing CRC and/or colorectal polyps, the method comprising: (a) providing a urine sample from said subject; (b) obtaining a metabolite profile from said urine sample; (c) comparing said metabolite profile with a reference metabolite profile; and (d) assessing, based on said comparison in step (c), whether said subject has or is predisposed to developing CRC and/or colorectal polyps.

Urine samples can be obtained as described above. The metabolite profile from the subject contains the corresponding information concerning the subject's urine sample as contained in the selected reference metabolite profile, as described above. Comparison of the metabolite profile from the subject to the reference metabolite profile allows for assessment of whether the subject has or is predisposed to developing CRC and/or colorectal polyps.

Merely by way of an illustrative example, the method might be a method for assessing whether a subject has or is predisposed to developing CRC. A urine sample could be taken and concentrations of the following metabolites measured: adipate; 3-hydroxybutyrate; creatine; guanidoacetate; dimethylamine; hypoxanthine; benzoate; O-acetylcarnitine; pyruvate; methanol; lactate; creatinine; xylose; 3-indoxylsulfate; trigonelline; taurine; threonine; p-methylhistidine; glucose; and 4-hydroxyphenylacetate. The concentration of each of these metabolites in the subject's urine is then compared to the concentrations of the corresponding metabolites in the reference metabolite profile. Detection of a higher concentration of any one or more of adipate, 3-hydroxybutyrate, creatine, guanidoacetate, dimethylamine, benzoate, O-acetylcarnitine, lactate, xylose, 3-indoxylsulfate, trigonelline, taurine, threonine, p-methylhistidine and 4-hydroxyphenylacetate in the subject's metabolite profile than in the reference metabolite profile may indicate that the subject has or is predisposed to developing CRC. Similarly, a lower concentration of any one or more of hypoxanthine, pyruvate, methanol, creatinine, and glucose in the subject's metabolite profile than in the reference metabolite profile may indicate that the subject has or is predisposed to developing CRC.

Diagnostic Kits

The invention also provides kits for assessing whether a subject has or is predisposed to developing CRC and/or colorectal polyps. Such kits may comprise one or more reagents for detecting the presence and/or concentration of one or more metabolites in a urine sample of a subject, and may include instructions for use of the kit for assessing whether a subject has or is predisposed to developing CRC and/or colorectal polyps.

The most reliable results are likely obtained when urine samples are processed, e.g. by NMR spectroscopy, in a laboratory setting. For instance, a urine sample might be obtained from a subject in the office of a medical practitioner and then sent to a hospital or commercial medical laboratory for further testing. However, in many instances, it may be desirable to provide immediate results in a clinician's office or to permit a subject to conduct testing at home. The need for a test that is portable, pre-packaged, disposable, usable by a subject without assistance or direction, etc. may in some instances be of more importance than a high degree of accuracy. In many instances, particularly where there will be follow-up with a medical practitioner, a preliminary test, even one with reduced sensitivity and/or specificity may be sufficient. Thus, an assay presented in kit form may involve detection and measurement of a relatively small number of metabolites, to reduce the complexity and cost of the assay.

Any form of urine assay capable of detecting urine metabolites as described herein may be used. Typically, the assay will quantitate the urine metabolites to some extent e.g. whether they are higher or lower in concentration or in amount than a predetermined threshold value. Such kits may take the form of a test strip, dip stick, cassette, cartridge, chip-based or bead-based array, multi-well plate, or series of containers, or the like. One or more reagents are provided to detect the presence and/or concentration and/or amount of selected urine metabolites. The subject's urine may be dispensed directly onto the assay or indirectly from a stored sample. The presence or absence of a metabolite above or below a pre-determined threshold may be displayed e.g. by a chromogenic, fluorogenic, electrochemiluminescent or other output, e.g. as in an enzyme immunoassay (EIA) such as an enzyme-linked immunoassay (ELISA).

In an embodiment, a kit may comprise a solid substrate, such as e.g. a chip, slide, array, etc., with reagents capable of detecting and/or quantitating one or more urine metabolites immobilized at predetermined locations on the substrate. By way of an illustrative example, a chip can be provided with reagents immobilized at discrete, predetermined locations for detecting and quantitating in a urine sample the concentration of adipate; 3-hydroxybutyrate; creatine; guanidoacetate and dimethylamine. As discussed above, elevated levels of these metabolites were found in the urine of subjects with CRC. The chip may be configured such that a detectable output (e.g. colour change) is provided only if the concentration of one or more of these metabolites is over a threshold value, the threshold value being selected to distinguish between a metabolite concentration indicative of healthy subjects and those having or predisposed to developing CRC. Thus, the presence of a detectable output such as a colour change provides an immediate indication that the urine sample contains significantly elevated levels of one or more relevant urine metabolites, indicating that the subject has or is predisposed to developing CRC.

Systems for Performing the Assessment of CRC or Colorectal Polyps

Figure 29:
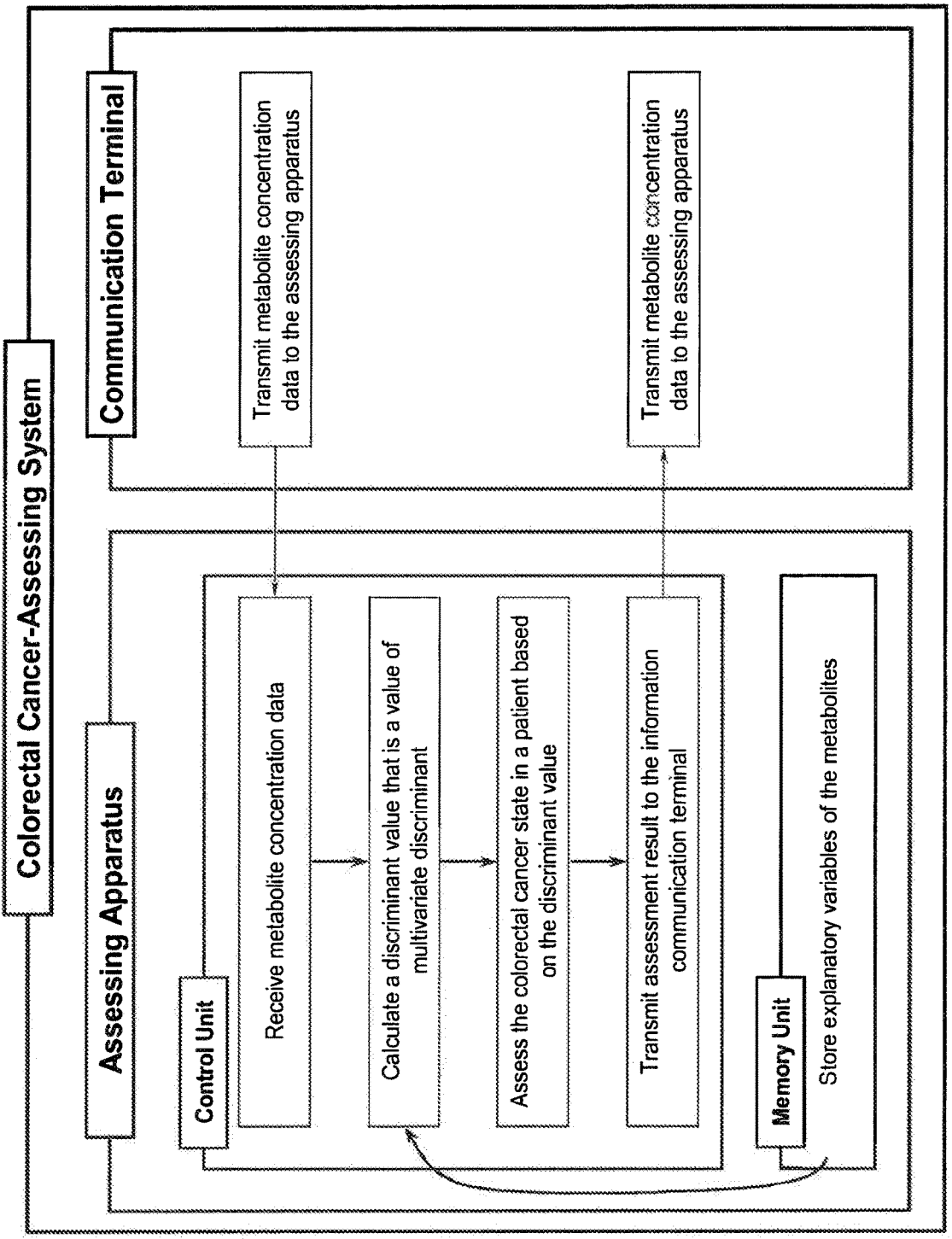
FIG. 29 is a diagram of the invention that provides a system for assessing whether a subject has or is predisposed to developing CRC and/or colorectal polyps.

In an embodiment, the invention provides a system for assessing whether a subject has or is predisposed to developing CRC and/or colorectal polyps. As shown in FIG. 29, such a system may comprise:

(a) a CRC- and/or colorectal polyps-assessing apparatus including a control unit and a memory unit to assess a CRC state in a subject; and (b) an information communication terminal apparatus that provides data on the presence and/or concentration and/or amount of metabolites in a urine sample from the subject connected to each other communicatively, wherein the information communication terminal apparatus includes:

(a) a data sending unit that transmits the data on the presence and/or concentration and/or amount of metabolites in the sample to the CRC- and/or colorectal polyps-assessing apparatus; and (b) an assessment result-receiving unit that receives the assessment result of the CRC and/or colorectal polyps state of the subject transmitted from the CRC- and/or colorectal polyps-assessing apparatus, wherein the control unit of the CRC- and/or colorectal polyps-assessing apparatus includes:

(a) a data-receiving unit that receives the data on the metabolite concentration and/or amount of the sample transmitted from the information communication terminal apparatus;

(b) a discriminant value-calculating unit that calculates a discriminant value that is a value of multivariate discriminant, based on both the concentration and/or amount value of the metabolite in the sample received by the data-receiving unit and a multivariate discriminant with the concentration and/or amount of the metabolite as explanatory variable stored in the memory unit;

(c) a discriminant value criterion-assessing unit that assesses the CRC or colorectal polyps state in the subject, based on the discriminant value calculated by the discriminant value-calculating unit; and (d) an assessment result-sending unit that transmits the assessment result of the subject obtained by the discriminant value criterion-assessing unit to the information communication terminal apparatus.

Evaluation of Efficacy of Pharmaceutical Agents and/or Physical Treatments and/or Surgical Treatment Metabolomic analysis is ideal for identification of and evaluation of the effects of potential pharmaceutical agents and/or new physical and/or surgical treatments against CRC, colorectal polyps and/or adenomatous polyps. Urine samples can be taken one or more times, by methods described previously herein, from a subject before and after treatment. The treatment can include administration of one or more pharmaceutical agents at one or more doses, and/or carrying out one or more physical and/or surgical treatments, to or on a subject. The administration of pharmaceutical agents can be made in many different ways including, but not limited to, injection, oral administration, patch or ointment application.

The metabolite profiles obtained from the samples can be compared with each other and/or with the metabolite profile from subjects without CRC and/or colorectal polyps. The comparison can indicate the efficacy of the pharmaceutical agents and/or the physical treatment and/or surgical treatment through changes of the metabolite profile in urine samples of the subject. Also, comorbidities and medications of a subject can be studied in subsequent analyses to determine their effects on the metabolomic test results and specifically whether they contribute to discordant results. In addition, the metabolite profiles of the CRC samples can be correlated with operative and histological findings to determine whether CRC location or stage can change a metabolite profile.

This invention is further illustrated by the following non-limiting examples.

Example 1. Assessment of CRC Group Versus Normal Group

Subjects for the normal group were recruited from a population based study of 1,200 asymptomatic subjects who were supposed to be exposed to an average or high risk of CRC, based on family history of colorectal cancer or personal history of colorectal polyps. Subjects for the CRC group were all newly diagnosed with CRC.

Four hundred forty four subjects without CRC and/or colorectal polyps were selected and classified as the normal group. Seventy seven CRC subjects were classified as the CRC group. Clinical information was obtained from study questionnaires, and subjects completed a medical questionnaire, had a FOBT, FIT, and a colonoscopy for determination of classification.

Urine samples were collected from subjects of the two groups. The urine samples were frozen at −80° C. within 24 hours of collection. Urine sample collection containers were pre-filled with sodium azide powder to stop any bacterial growth in the urine while it is waiting to be frozen at −80° C.

Urine samples were thawed at room temperature in the biohood 24 hours prior to NMR acquisition. For the non-automated (manual) NMR acquisition, 585 µL of each sample was diluted with 65 µL of internal standard consisting of 5 mM sodium 2,2-dimethyl-2-silapentane-5-sulfonate (DSS), 100 mM imidazole and 0.2% sodium azide in 99% D2O (Chenomx Inc., Edmonton, AB) to achieve a total volume of 650 µL and stored at 4° C. For the automated (robotic) NMR acquisition, 675 µL of each sample was diluted with 754, of the same Chenomx internal standard to achieve a total volume of 750 µL and stored at 4° C. On the day of NMR acquisition, the pH of each sample was measured. Various concentrations of HCl and NaOH were added to the samples to achieve a pH between 6.7 and 6.8 to minimize chemical exchange as the chemical shift would change with pH. For the samples for the non-automated NMR, an aliquot of 600 µL of the samples was placed in 5 mm NMR tubes and capped; for the samples for the automated NMR, 700 µL was used.

Manual/Non-Automated Mode:

One-dimensional NMR spectra were acquired using an Oxford 600 Hz NMR spectrometer with a Varian VNMRS two channel console and running VNMRJ software version 2.2C on a RHEL 4 host computer in the Canadian National High Field NMR Centre (NANUC). Samples (600 µL) were set to a depth of 66 mm in the depth gage and then inserted into the spectrometer. All samples were run at a sweep width (sw) of 7225.43 Hz. The saturation frequency (sfrq), transmitter offset (tof) and pulse width (pw) were all individually calibrated at the start of each set of sample runs. The tof ranged from (−213 to −215 Hz) and the pw ranged from 6 to 8 microseconds. Shims were optimized until an acceptable line width value was obtained at relative peaks heights of: 50% (<1.0 Hz), 0.55% (<12.0 Hz), and 0.11% (<20.0 Hz). During post-processing of the sample, zero filling was used to increase the actual acquired data points to the next largest factor of 2. No weighting functions were applied. The first increment of a 2D-1H,1H-NOESY pulse sequence was utilized for the acquisition of 1H-NMR (Hydrogen-1 nuclear magnetic resonance) data and for suppressing the solvent signal. Experiments contained a 100 ms mixing time along with a 990 ms pre-saturation time (~80 Hz gammaB1). Spectra were collected at 25° C. through a total of 32 scans over a period of 3.5 minutes; a total recycle delay of 5 seconds was also used.

Automated Mode:

Automated runs followed exactly the same experimental parameters used in the manual mode with the exception of i) use of 700 µL sample and ii) an additional 30 s of equilibration time in the NMR to allow the sample to equilibrate to 25° C. All sample handling was done with a Varian 768 AS sample handling robot. The first sample of the batch was manually shimmed to satisfactory line width values and subsequent samples were automatically shimmed. Any spectra that did not meet acceptable line height values were discarded and the sample was re-run.

After the spectra were obtained, samples from both manual and automated mode were removed from NMR tubes with glass Pasteur pipettes and transferred into eppendorf tubes. The pH of each sample was then rechecked to ensure that the pH had not shifted a significant amount. Samples were re-stored in the −80° C. freezer.

Once the spectra were acquired, quantification of metabolites was done using Chenomx NMRSuite v4.6 software (Chenomx, Inc. Edmonton, Canada), which compared the integral of a known reference signal (in this case DSS) with signals derived from a library of compounds to determine concentration relative to the reference signal. The quantification was done by one individual and verified by a second individual to optimize accuracy.

Over 240 metabolites were considered, and 72 were found to be significant, that is, the spectral peaks of 72 metabolites in the compound library were identified in the spectra of the samples: 1,6-Anhydro-β-D-glucose, 1-Methylnicotinamide, 2-Hydroxyisobutyrate, 2-Oxoglutarate, 3-Aminoisobutyrate, 3-Hydroxybutyrate, 3-Hydroxyisovalerate, 3-Hydroxymandelate, 3-Hydroxyphenylacetate, 3-Indoxyl sulfate, 4-Hydroxyphenylacetate, Acetate, Acetone, Adipate, Alanine, Ascorbate, Asparagine, Benzoate, Betaine, Butyrate, Carnitine, Citrate, Creatine, Creatinin, DSS (Chemical Shape Indicator), Dimethylamine, Ethanol, Formate, Galactose, Glucose, Glutamine, Glycerol, Glycine, Glycolate, Guanidoacetate, Hippurate, Histidine, Hypoxanthine, Ibuprofen, Isoleucine, Lactate, Leucine, Lysine, Mannitol, Methanol, Methylguanidine, N,N-Dimethylglycine, O-Acetylcarnitine, Pantothenate, Propylene glycol, Pyroglutamate, Pyruvate Salicylurate, Serine, Succinate, Sucrose, Tartrate, Taurine, Threonine, Trigonelline, Trimethylamine, Trimethylamine N-oxide, Tyrosine, Uracil, Urea, Valine, Xylose, cis-Aconitate, trans-Aconitate, β-Alanine, Π-Methylhistidine, T-Methylhistidine.

Metabolite concentrations were log transformed to normalize the concentrations. Those metabolites that were not products of normal human metabolism, i.e. xenobiotics, such as ibuprofen and salicylurate, were excluded. The internal standard DSS was also excluded in the analysis, and 69 metabolites were obtained as a reference metabolite profile.

The metabolite measurements in samples from the CRC group were compared to metabolite measurements in samples from the normal group. Simca-P+ v12.0.1 software (Umetrics, Umea, Sweden) was used to perform the multivariate statistical analyses to identify differences arising between the groups of data sets. These analyses included PLS-DA, and OPLS.

Further data analysis was preformed in order to determine which specific metabolites were the strongest contributors to the data separation between the CRC group and the normal group samples by a VIP plot. The metabolites identified with a VIP score of greater than 1 were Adipate, 3-Hydroxybutyrate, Creatine, Guanidoacetate, Dimethylamine, Hypoxanthine, Benzoate, O-Acetylcarnitine, Pyruvate, Methanol, Lactate, Creatinine, Xylose, 3-Indoxyl sulfate, Trigonelline, Taurine, Threonine, Π-Methylhistidine, Glucose, 4-Hydroxyphenylacetate. The result is summarized in Table 1 together with the list of 69 metabolites.

The following assessments were performed with two different metabolite profiles, one with all the 69 metabolites found to be significant for the separation of the CRC group and the normal group, and the other with 20 metabolites with a VIP value higher than 1.

Figure 2:
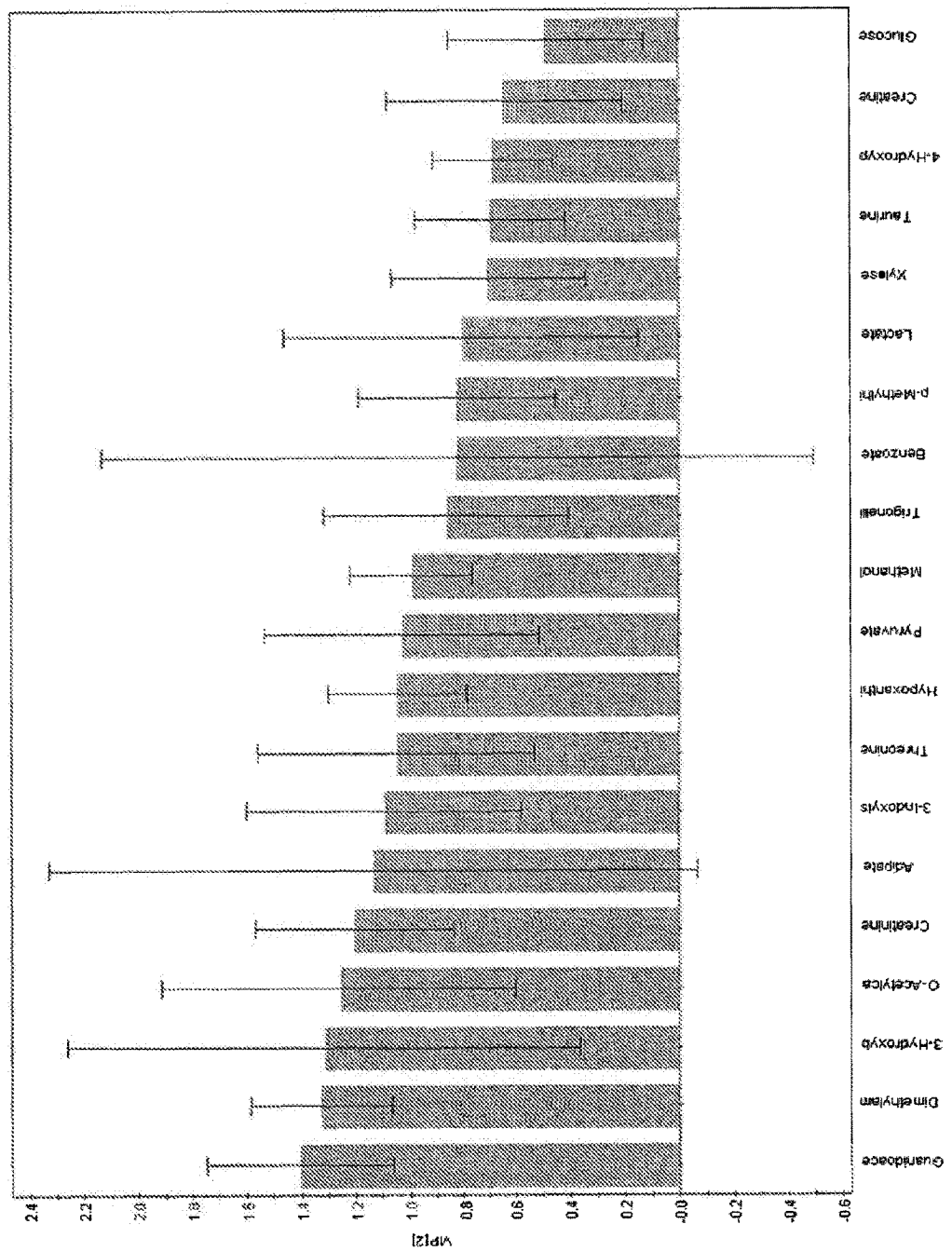
FIG. 2 is a VIP plot of analyzed metabolites in order of their contribution to the separation between data from urine samples obtained from subjects having CRC and that from subjects without CRC and/or colorectal polyps for 20 metabolites with a VIP value higher than 1.

The VIP plots were generated using SIMCA-P+ to illustrate which metabolites contribute the most to the separation between the normal and CRC groups (FIGS. 1 and 2).

Figure 3:
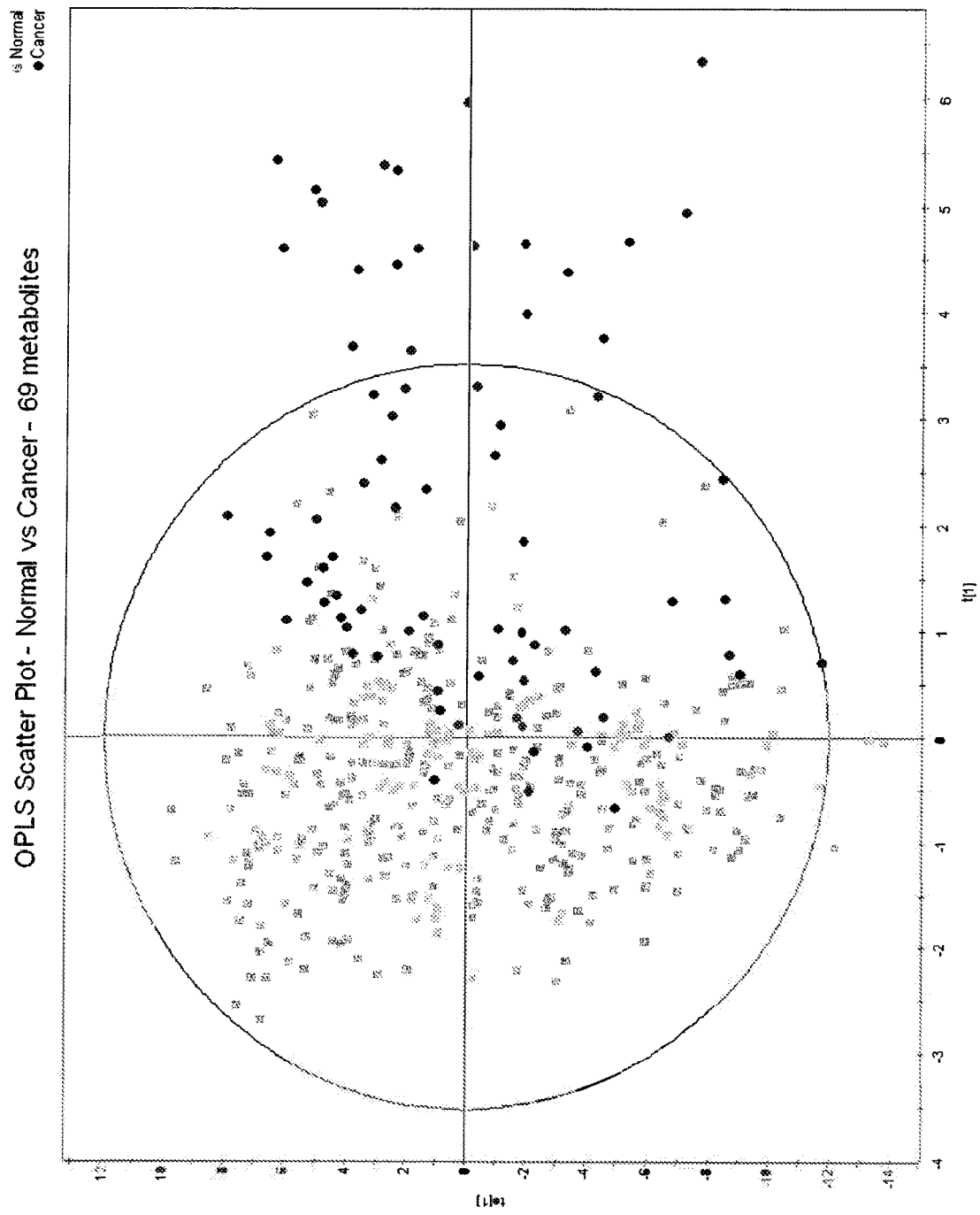
FIG. 3 is a 2-dimensional orthogonal partial least square (OPLS) scatter plot of the data from urine samples obtained from subjects without CRC and/or colorectal polyps (grey squares) compared to that from subjects having CRC (black dots) constructed from 69 metabolites.
Figure 4:
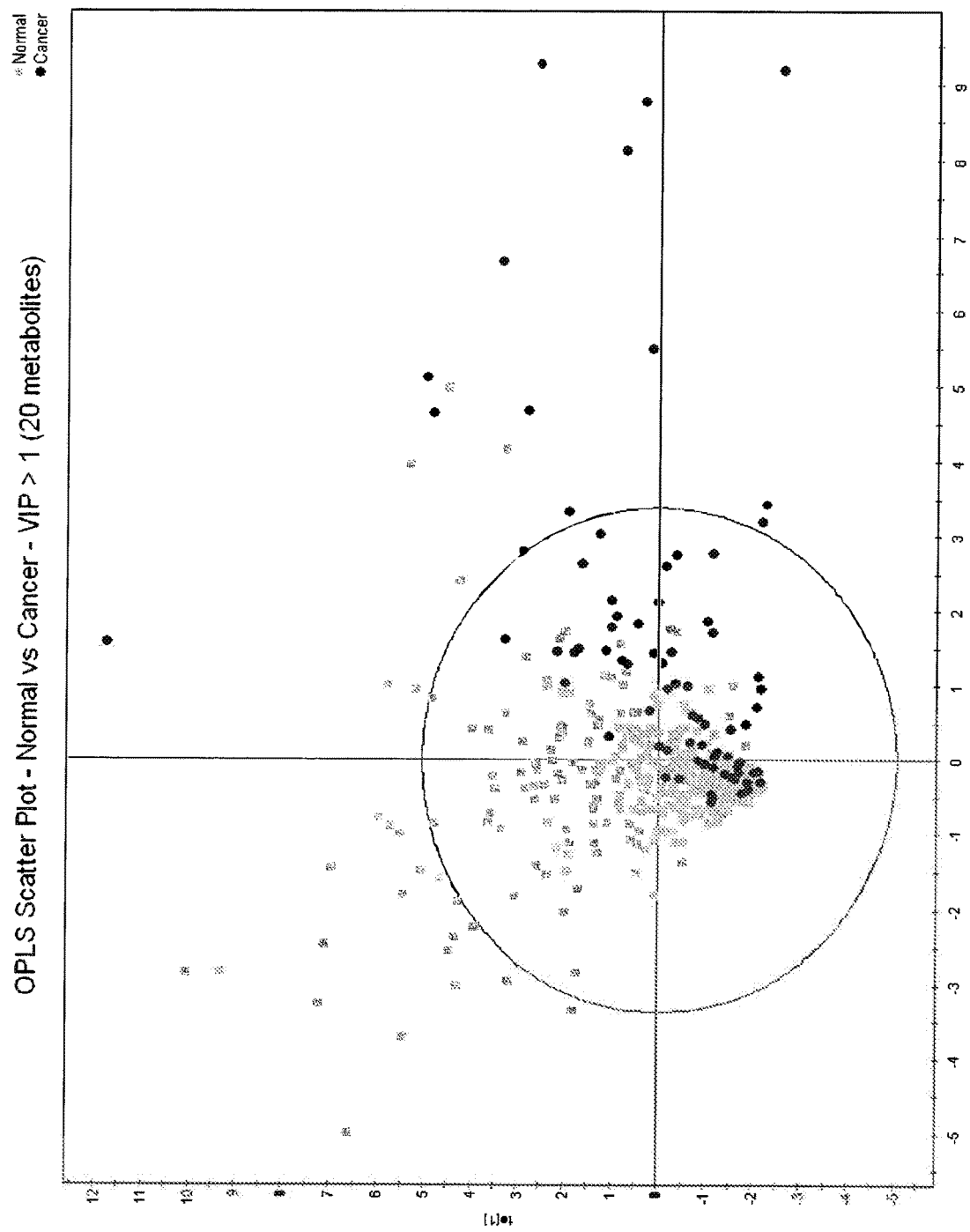
FIG. 4 is a 2-dimensional OPLS scatter plot of the data from urine samples obtained from subjects without CRC and/or colorectal polyps (grey squares) compared to that from subjects having CRC (black dots) constructed from 20 metabolites with a VIP value higher than 1.

Using two-component separation, the OPLS scatter plots shown in FIGS. 3 and 4, implemented in SIMCA-P+12, illustrated the normal group as grey squares and the CRC group as black dots. Notwithstanding a degree of overlap, the two groups generally appeared on the different (right and left) sides of the plot.

Figure 5:
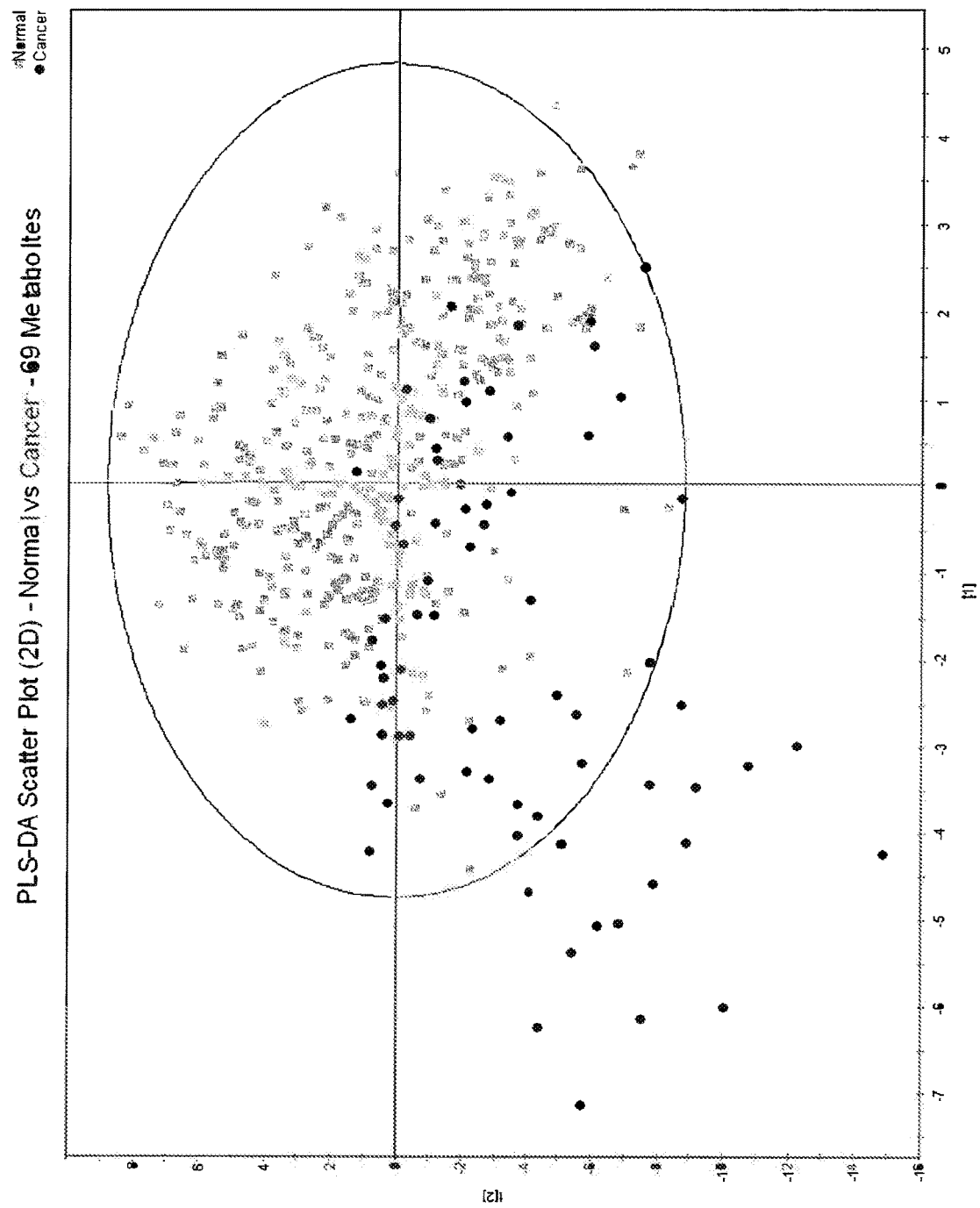
FIG. 5 is a 2-dimensional partial least square discriminant analysis (PLS-DA) scatter plot of the data from urine samples obtained from subjects without CRC and/or colorectal polyps (grey squares) compared to that from subjects having CRC (black dots) constructed from 69 metabolites.
Figure 6:
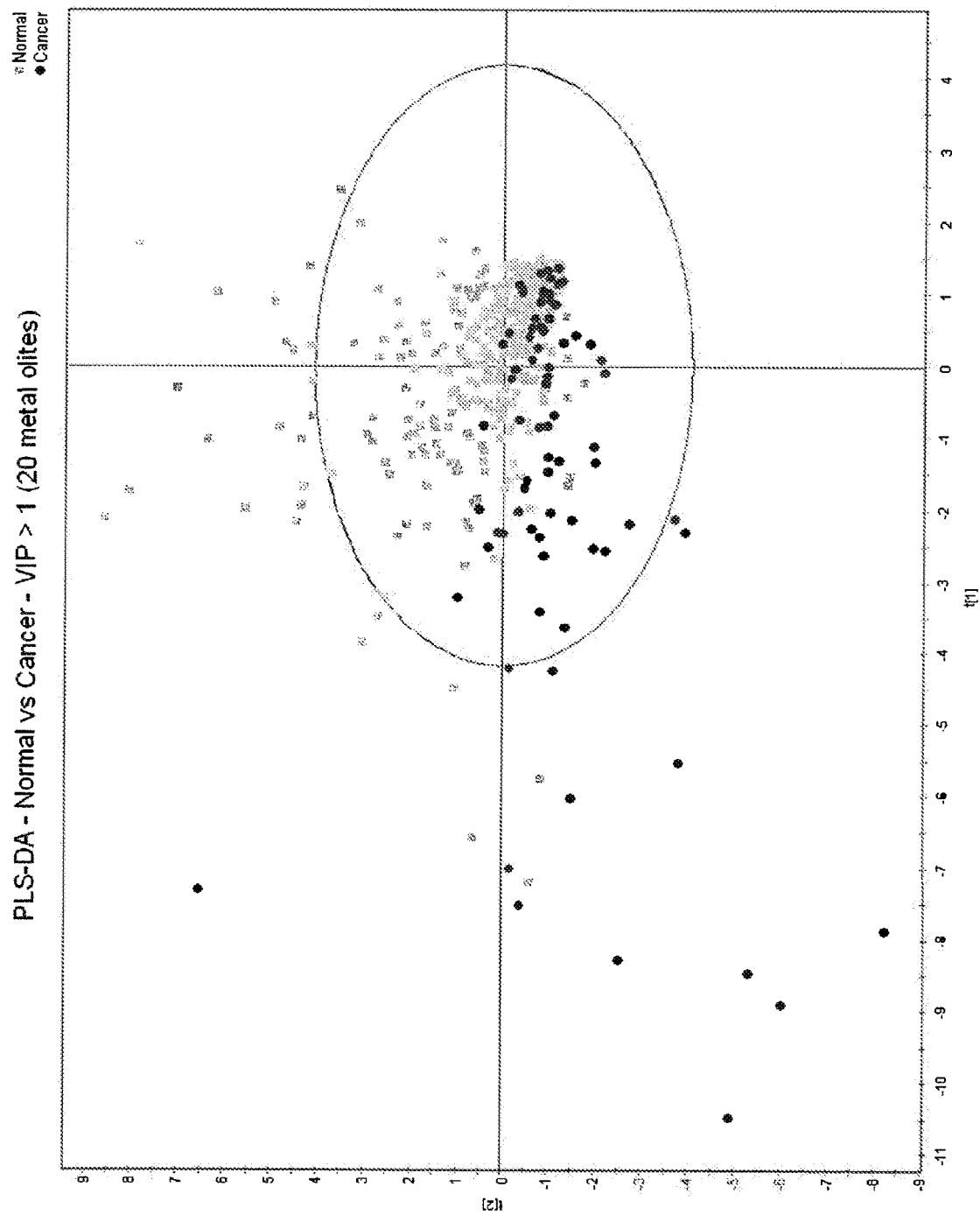
FIG. 6 is a 2-dimensional PLS-DA scatter plot of the data from urine samples obtained from subjects without CRC and/or colorectal polyps (grey squares) compared to that from subjects having CRC (black dots) constructed from 20 metabolites with a VIP value higher than 1.

The 2-dimensional scatter plots of the PLS model were shown in FIGS. 5 and 6. In each plot, the normal group were in grey squares and the CRC group were in black dots. A similar separation to the OPLS scatter plots of the normal group and the CRC group could be seen. Even though there was an overlap between the CRC group and the normal group, the two groups appear on the different (top and bottom) sides of each plot.

Figure 7:
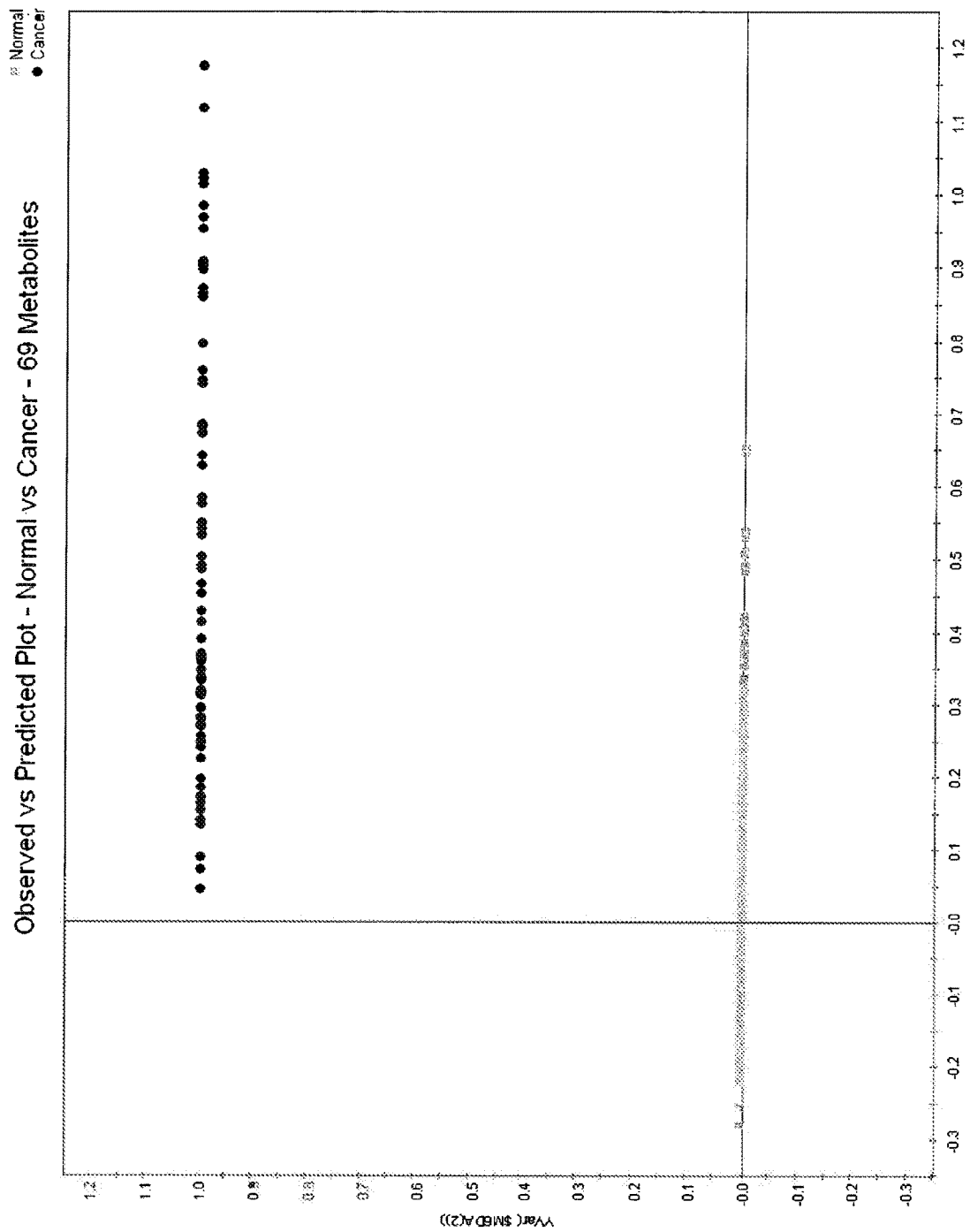
FIG. 7 is an observed versus predicted plot of the OPLS model of FIG. 3. Data from urine sample obtained from subjects without CRC and/or colorectal polyps is displayed as grey squares and that from subjects having CRC is displayed as black dots.
Figure 8:
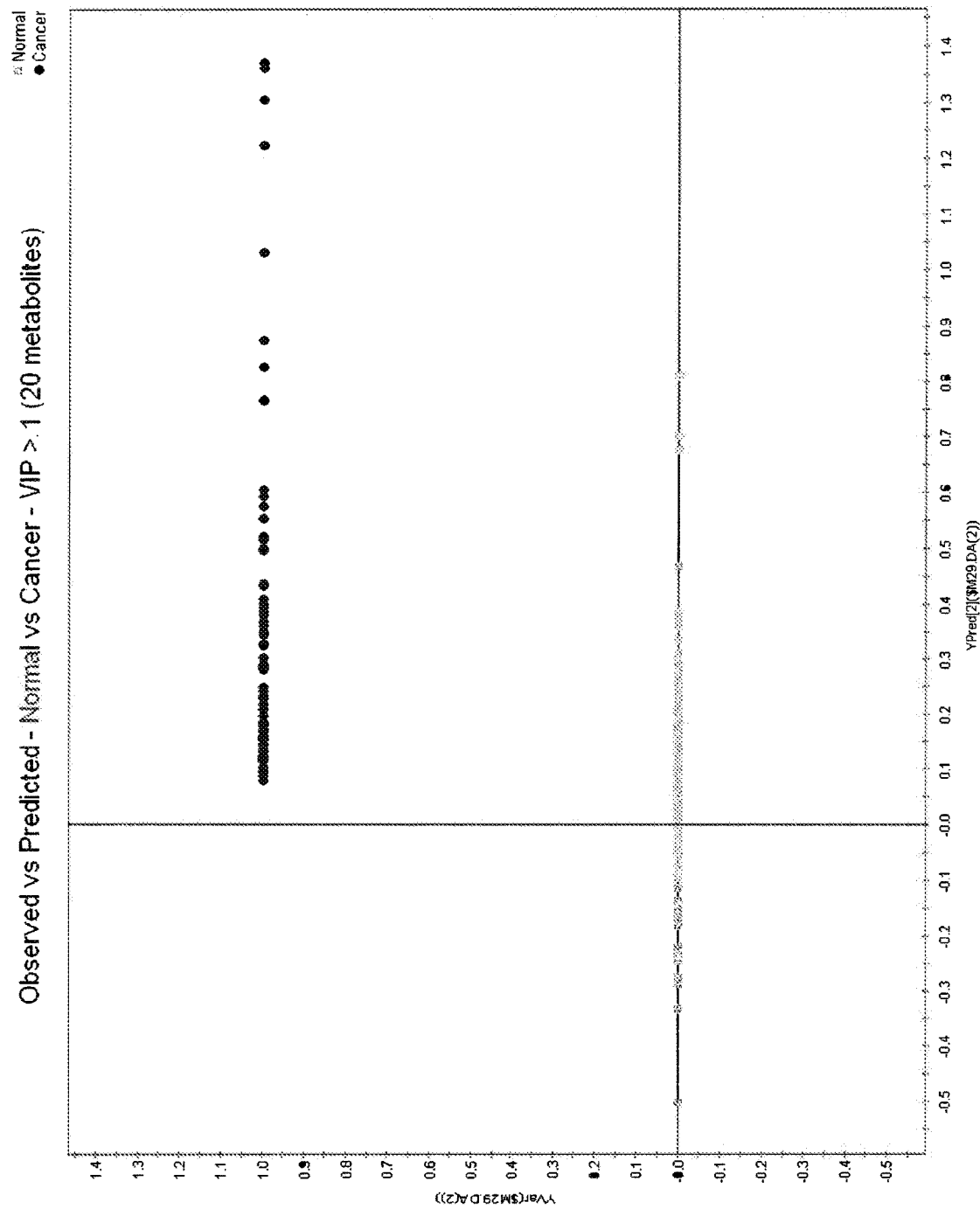
FIG. 8 is an observed versus predicted plot of the OPLS model of FIG. 4. Data from urine sample obtained from subjects without CRC and/or colorectal polyps is displayed as grey squares and that from subjects having CRC is displayed as black dots.

To generate sensitivity and specificity data, the observed versus predicted data plots were generated for the OPLS models (FIGS. 7 and 8) and arbitrary cut-off points for the predicted value (YPred) were chosen where the two groups overlapped (FIGS. 7 and 8). The grey squares, indicating the normal group, to the left of the cut-off were TN and those that are to the right of the cut-off were the FP. The black dots, indicating CRC group, to the left of the cut-off were false negatives (FN), while those to the right were the true positives (TP). Sensitivity and specificity data were summarized in Table 2.

In Table 2, the model column indicated which metabolites were used to construct the model. The term "main model" referred to the model containing all 69 metabolites. The cut-off column corresponded to certain cut-off points on the ROC curve. Sensitivity and Specificity are measures of how accurate and precise the test is. The ROC Curve is a measure of how robust the models are. $R^2Y$ and $Q^2$ are measures of the quality of the models constructed; which means, the higher the numbers the better the model. A negative number means that the model is unusable.

From Table 2, it could be seen that with a cut-off point ranging from 0.114184-0.302331, results in a sensitivity range of 87.18-25.64% and specificity range of 54.03-98.10% would be achieved when using the metabolites with a VIP score greater than 1. Similarly, different cut-off points can be used for numerous subsets of the metabolites, which can also be observed in Table 2 with the different subsets of metabolites. For example, when using the top 15 metabolites and a cut-off range from 0.120717-0.326168 a sensitivity range of 79.49-20.51% and a specificity range of 34.12-99.53% can be achieved.

Figure 9:
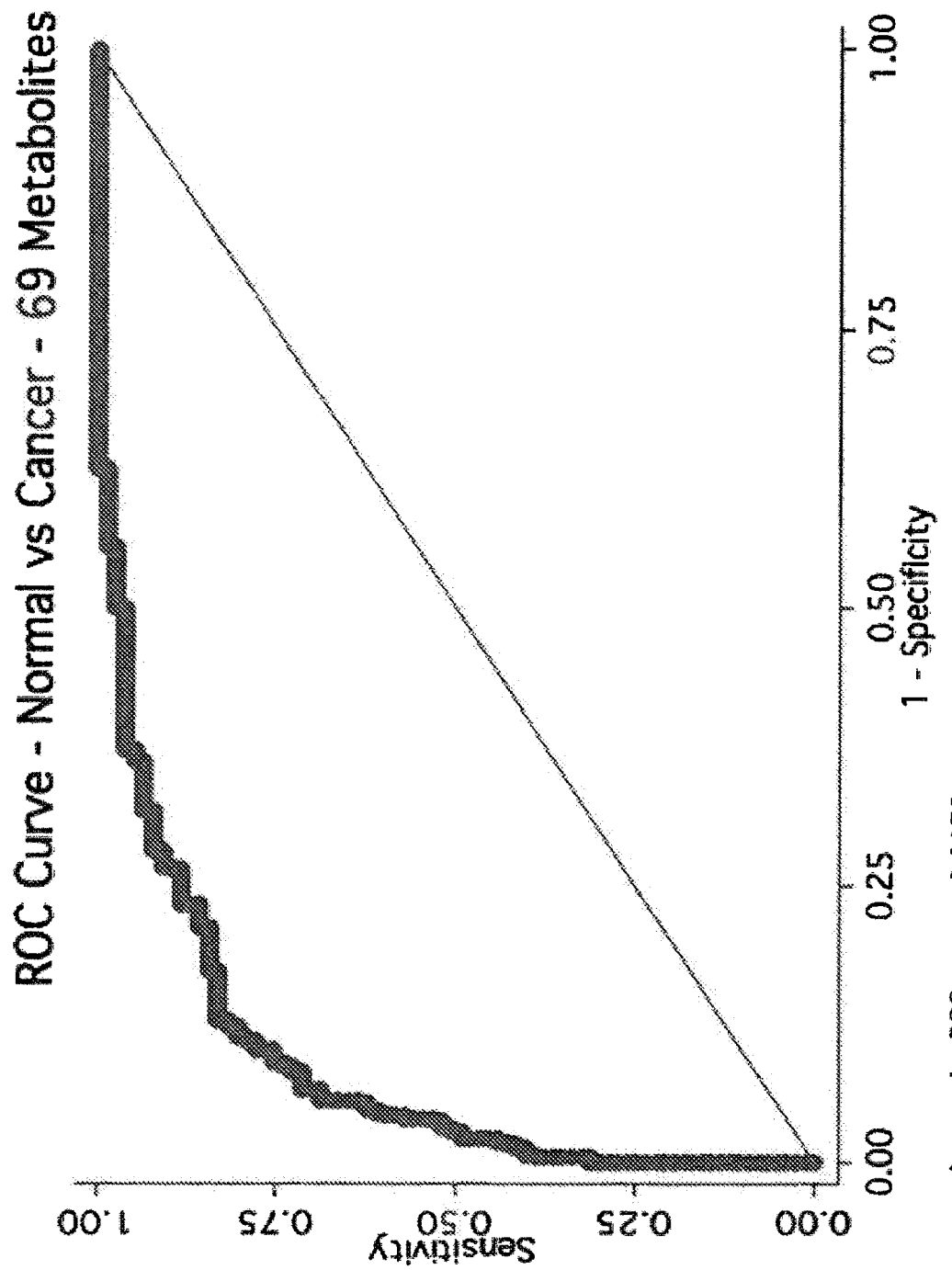
FIG. 9 is a receiver operating characteristics (ROC) curve of the OPLS model of FIG. 3.
Figure 10:
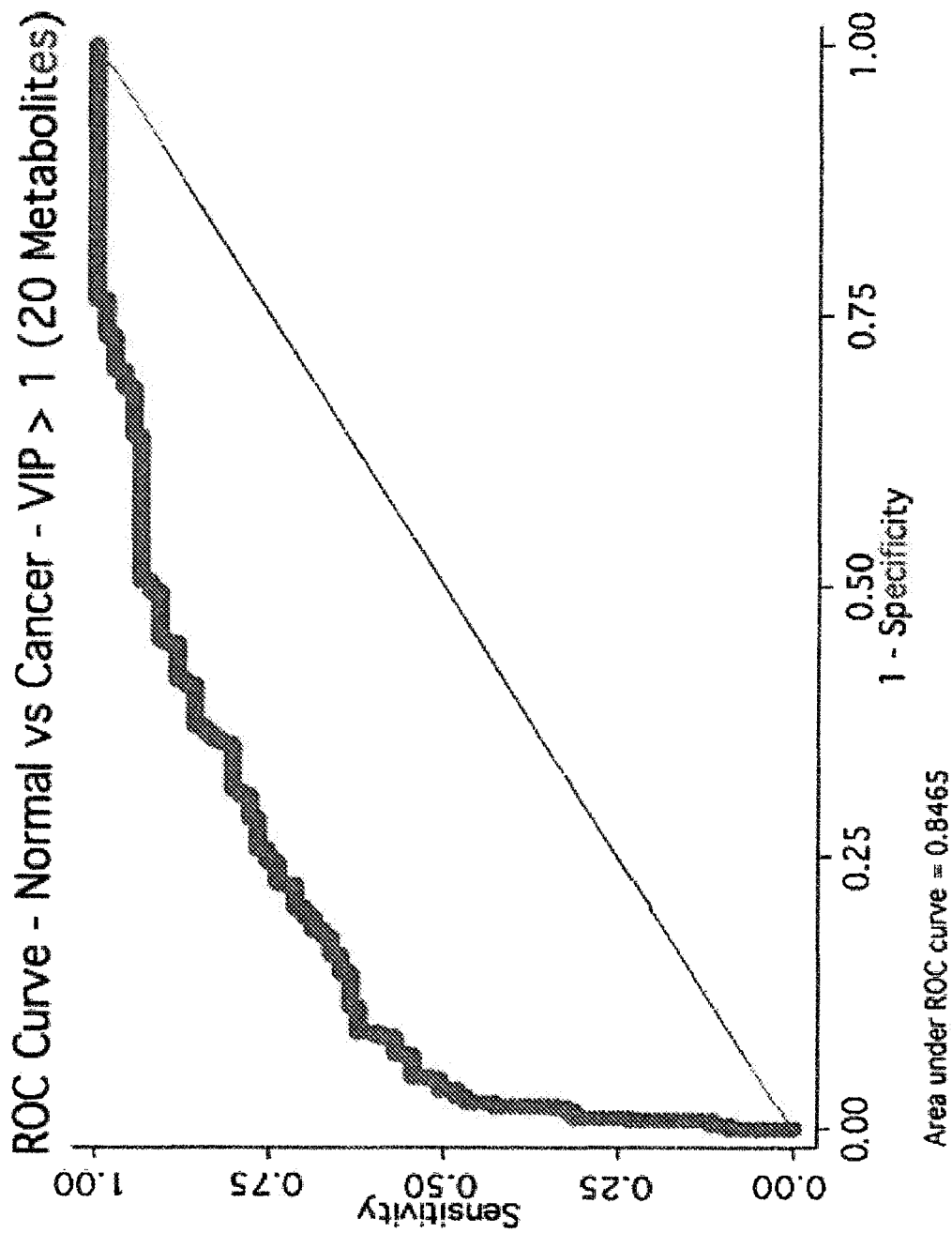
FIG. 10 is a ROC curve of the OPLS model of FIG. 4.

With the data from Table 2, the ROC curves of sensitivity versus 1-specificity were plotted (FIGS. 9 and 10) using STATA10.0 (College Station, Tex.). The ROC curves in the Figures had AUC scores of 0.9178 and 0.8465, respectively. This result showed that the metabolite profile consisting of 20 metabolites out of 69, with higher VIP value than 1, can also be used to assess whether a subject has or is predisposed to developing CRC, though the metabolite profile consisting of 69 metabolites might provide more accurate assessment. Table 2 also demonstrates that even five metabolites with highest VIP values could be used to assess whether a subject has or is predisposed to developing CRC.

Example 2. Assessment of Polyp Group Versus Normal Group

Subjects for the normal group and the polyp group were recruited from a population based study of 1,200 asymptomatic subjects who were supposed to be exposed to an average or high risk of CRC, based on family history of CRC or personal history of colorectal polyps. All subjects completed a medical questionnaire, had a FOBT, FIT, and a colonoscopy to determine classification of the subjects. One subject in the polyp group was found to be with CRC, and excluded from the test.

Four hundred forty four subjects without CRC and/or colorectal polyps were selected and classified as the normal group. The polyp group consisted of two hundred thirty six with tubular, tubulovillous, villous adenomas and hyperplastic polyps.

The process as described previously in "Assessment of Cancer Group versus Normal Group" was followed for urine sample collection, treatment of the sample, NMR acquisition, and analysis of the data obtained.

Over 240 metabolites were considered, and 72 were found to be significant, that is, the spectral peaks of 72 metabolites in the compound library were identified in the spectra of the study samples: 1,6-Anhydro-β-D-glucose, 1-Methylnicotinamide, 2-Hydroxyisobutyrate, 2-Oxoglutarate, 3-Aminoisobutyrate, 3-Hydroxybutyrate, 3-Hydroxyisovalerate, 3-Hydroxymandelate, 3-Hydroxyphenylacetate, 3-Indoxyl sulfate, 4-Hydroxyphenylacetate, Acetate, Acetone, Adipate, Alanine, Ascorbate, Asparagine, Benzoate, Betaine, Butyrate, Carnitine, Citrate, Creatine, Creatinin, DSS (Chemical Shape Indicator), Dimethylamine, Ethanol, Formate, Galactose, Glucose, Glutamine, Glycerol, Glycine, Glycolate, Guanidoacetate, Hippurate, Histidine, Hypoxanthine, Ibuprofen, Isoleucine, Lactate, Leucine, Lysine, Mannitol, Methanol, Methylguanidine, N,N-Dimethylglycine, O-Acetylcarnitine, Pantothenate, Propylene glycol, Pyroglutamate, Pyruvate Salicylurate, Serine, Succinate, Sucrose, Tartrate, Taurine, Threonine, Trigonelline, Trimethylamine, Trimethylamine N-oxide, Tyrosine, Uracil, Urea, Valine, Xylose, cis-Aconitate, trans-Aconitate, β-Alanine, Π-Methylhistidine, T-Methylhistidine.

Metabolite concentrations were log transformed to normalize the concentrations. Those metabolites that were not products of normal human metabolism, i.e. xenobiotics, such as ibuprofen and salicylurate, were excluded. The internal standard DSS was also excluded in the analysis, and 69 metabolites were obtained as a reference metabolite profile.

The metabolites identified with a VIP score of greater than 1 are Butyrate; Serine; Asparagine; p-Methylhistidine; 3-Hydroxybutyrate; Methanol; 3-Hydroxymandelate; Tyrosine; Trigonelline; β-Alanine; Histidine; Dimethylamine; Urea; 1,6-Anhydro-β-D-glucose; Glucose; Ethanol; Benzoate; Acetone; Threonine; 2-Hydroxyisobutyrate; Creatinine; 3-Hydroxyphenylacetate; 3-Indoxyl sulfate; Hippurate; Ascorbate; and 4-Hydroxyphenylacetate. The result was summarized in Table 3 together with the list of 69 metabolites.

The following analysis was performed with two different metabolite profiles, one with all the 69 metabolites found to be significant for the separation of the polyp group and the normal group, and the other with 26 metabolites with a VIP value higher than 1.

Figure 11:
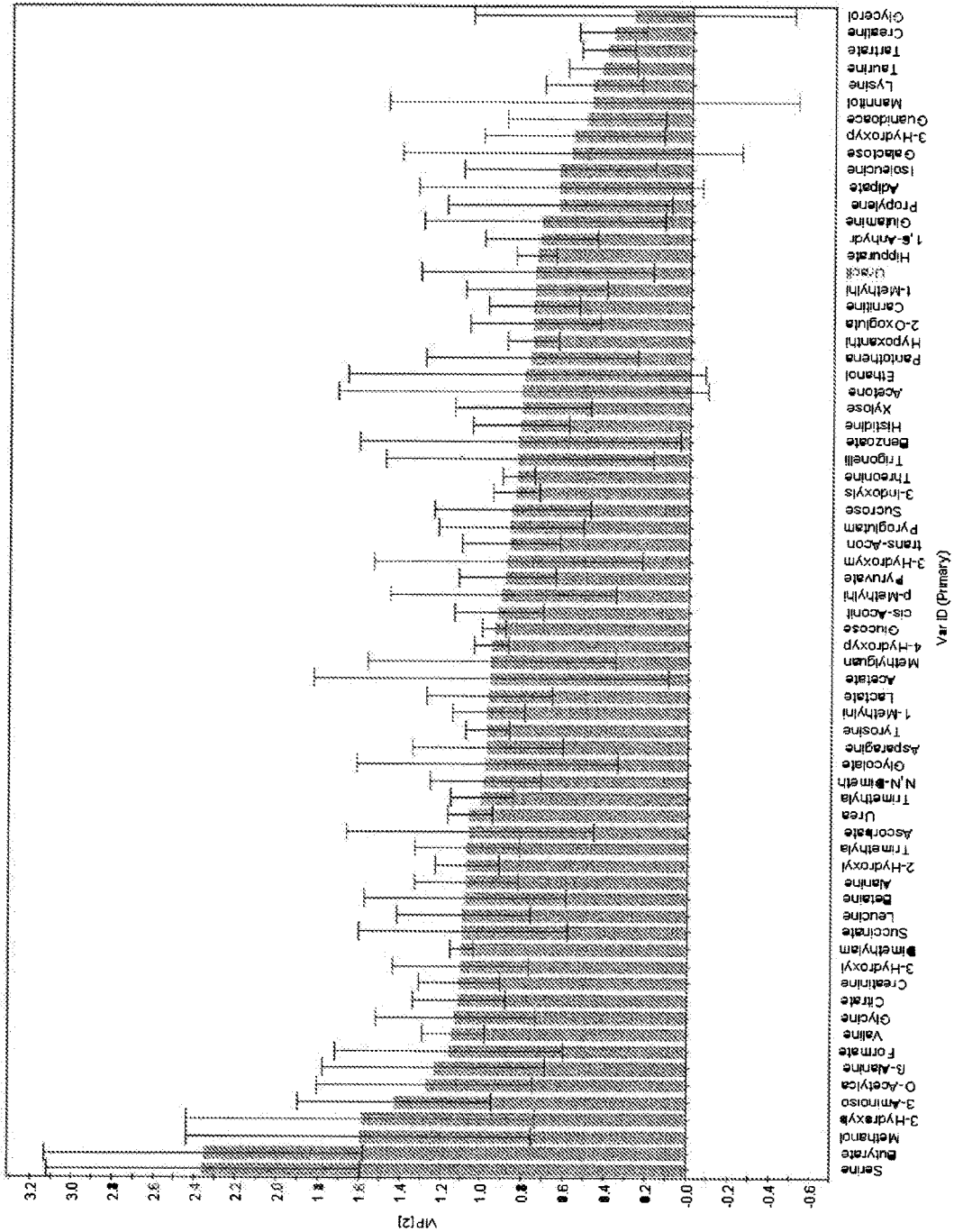
FIG. 11 is a VIP plot of analyzed metabolites in order of their contribution to the separation between the data from urine samples obtained from subjects without CRC and/or colorectal polyps and that from subjects having colorectal polyps for 69 metabolites.
Figure 12:
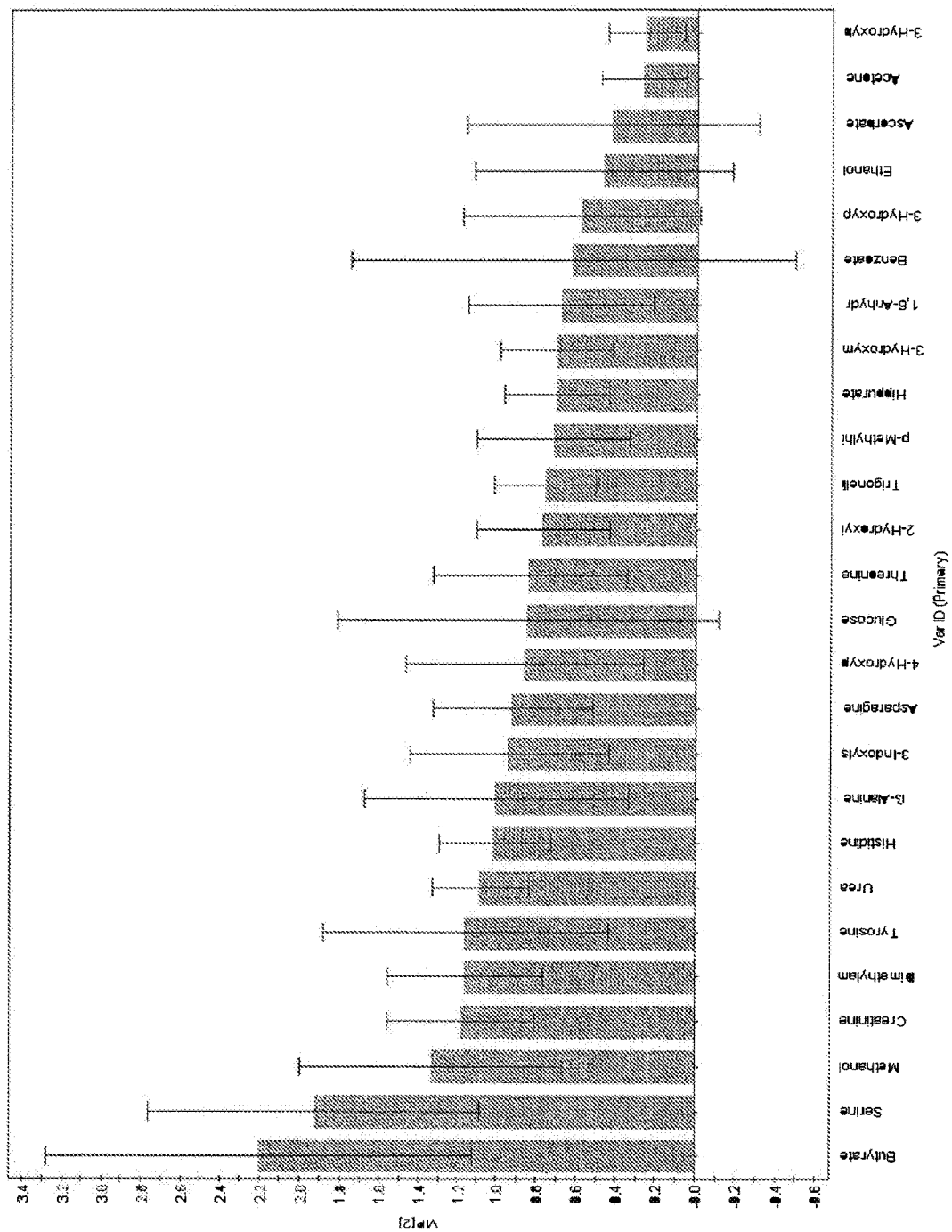
FIG. 12 is a VIP plot of analyzed metabolites in order of their contribution to the separation between the data from urine samples obtained from subjects without CRC and/or colorectal polyps and that from subjects having colorectal polyps for 26 metabolites with a VIP value higher than 1.
Figure 17:
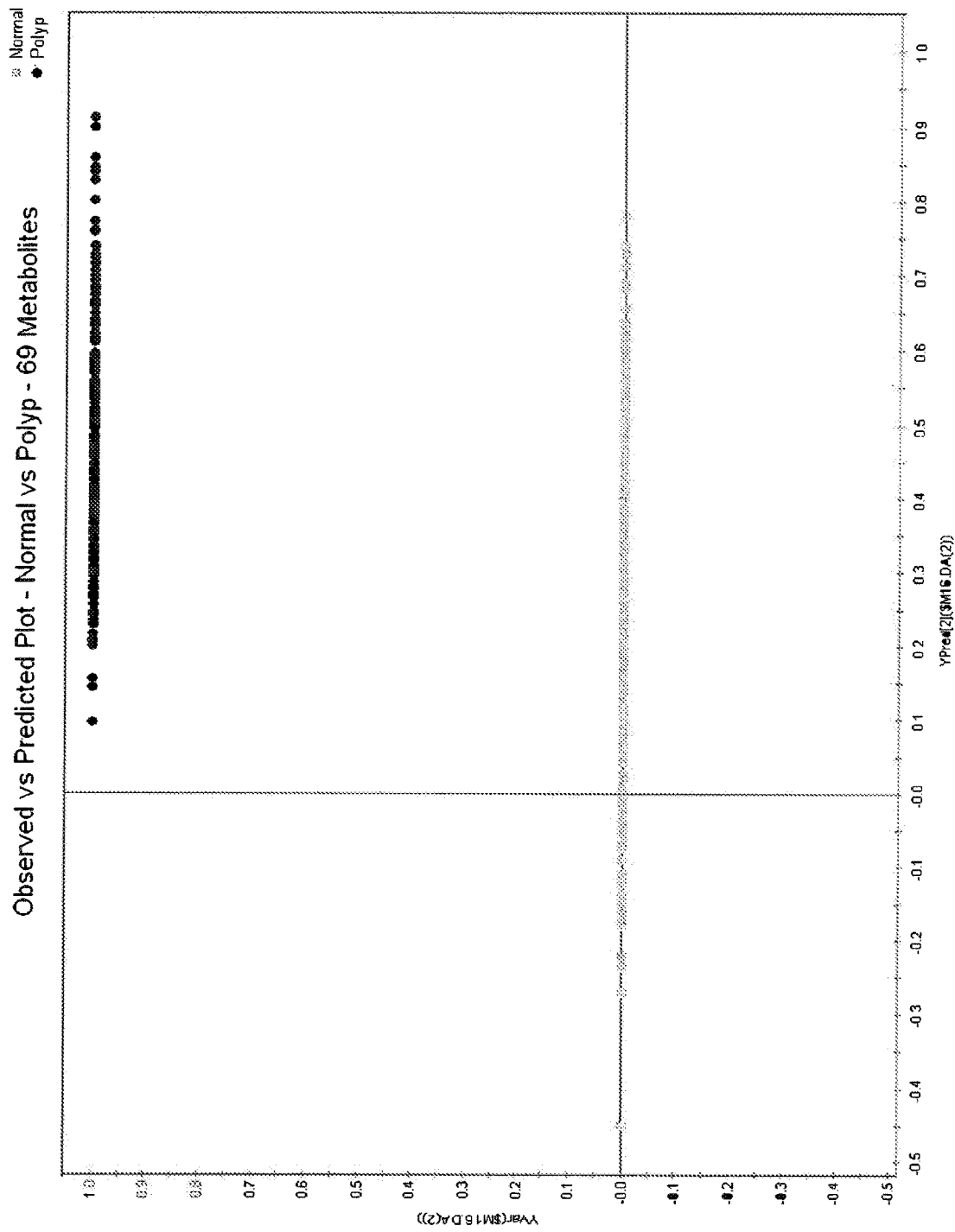
FIG. 17 is an observed versus predicted plot of the OPLS model of FIG. 13. Data from urine samples obtained from subjects without CRC and/or colorectal polyps are displayed as grey squares and that from subjects having colorectal polyps are displayed as black diamonds.
Figure 18:
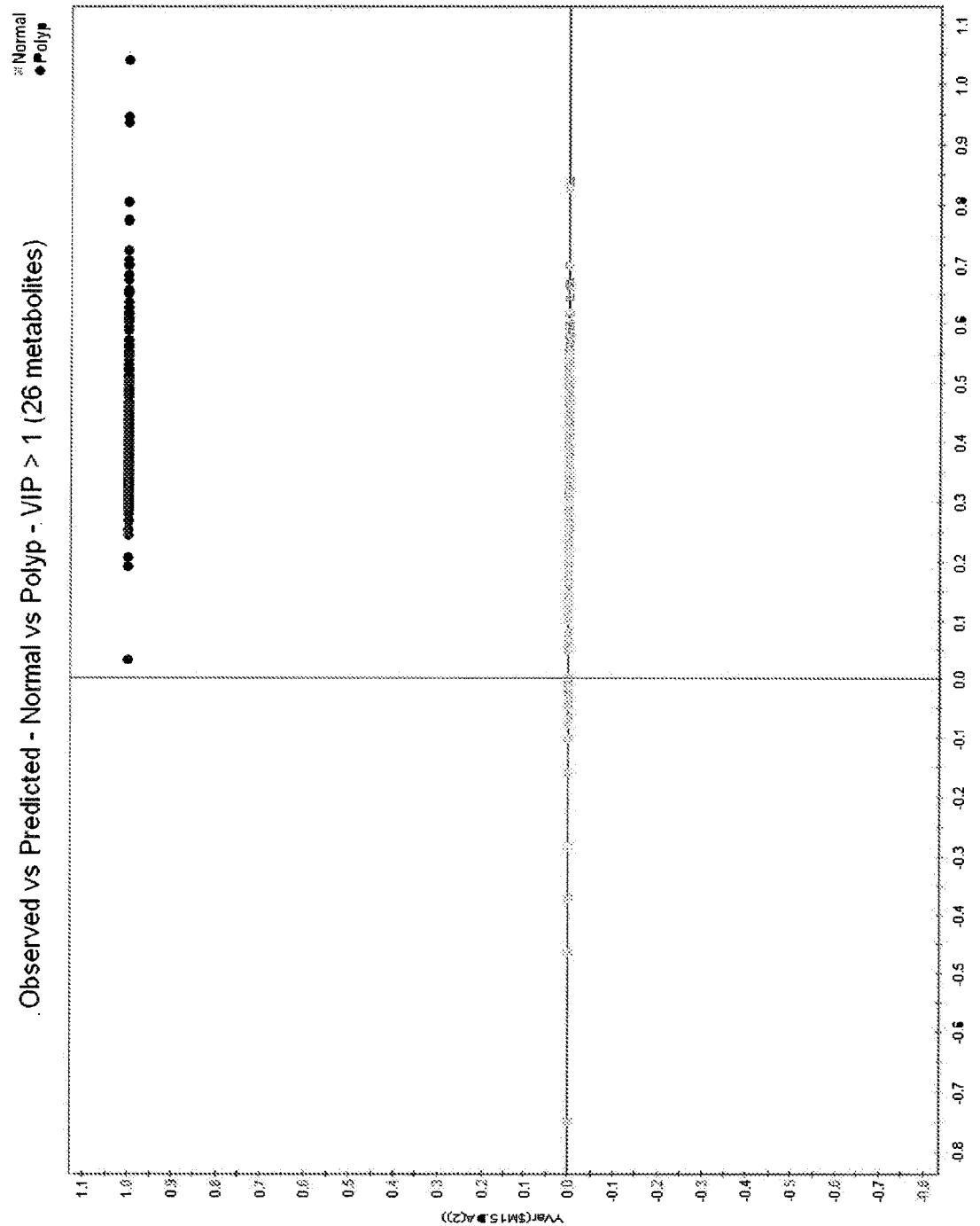
FIG. 18 is an observed versus predicted plot of the OPLS model of FIG. 14. Data from urine samples obtained from subjects without CRC and/or colorectal polyps are displayed as grey squares and that from subjects having colorectal polyps are displayed as black diamonds.

The VIP plots were generated to illustrate which metabolites contribute the most to the separation between the normal and polyp groups (FIGS. 11 and 12). The resulting OPLS (FIGS. 13 and 14), PLS-DA 2-dimensional scatter plots (FIGS. 15 and 16), observed verses predicted plots (FIGS. 17 and 18), ROC curves (FIGS. 19 and 20) and sensitivity & specificity data (Table 4) were produced.

Figure 13:
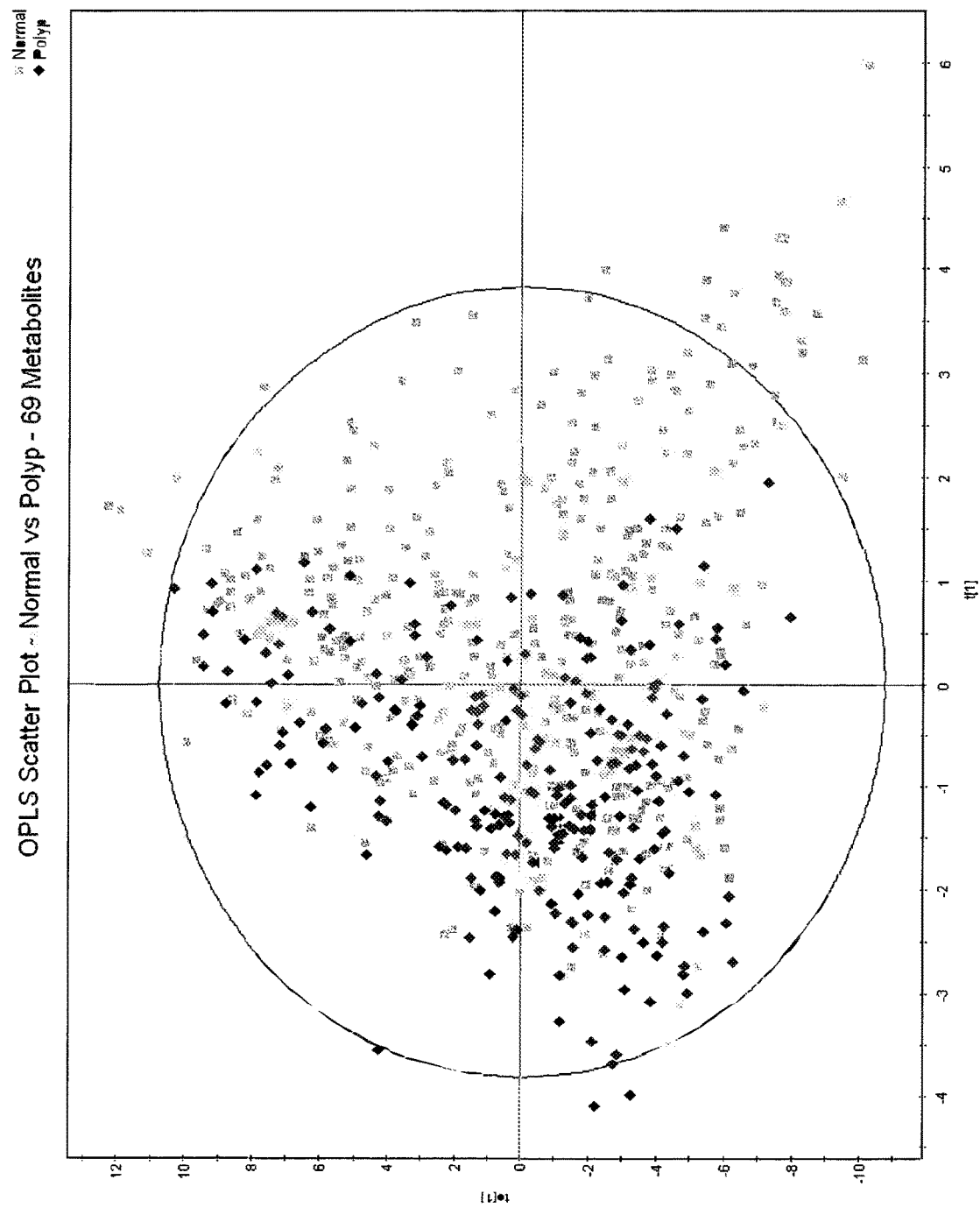
FIG. 13 is a 2-dimensional OPLS plot of the data from urine samples obtained from subject without CRC and/or colorectal polyps (grey squares) compared to that from subjects having colorectal polyps (black diamonds) constructed from 69 metabolites.
Figure 14:
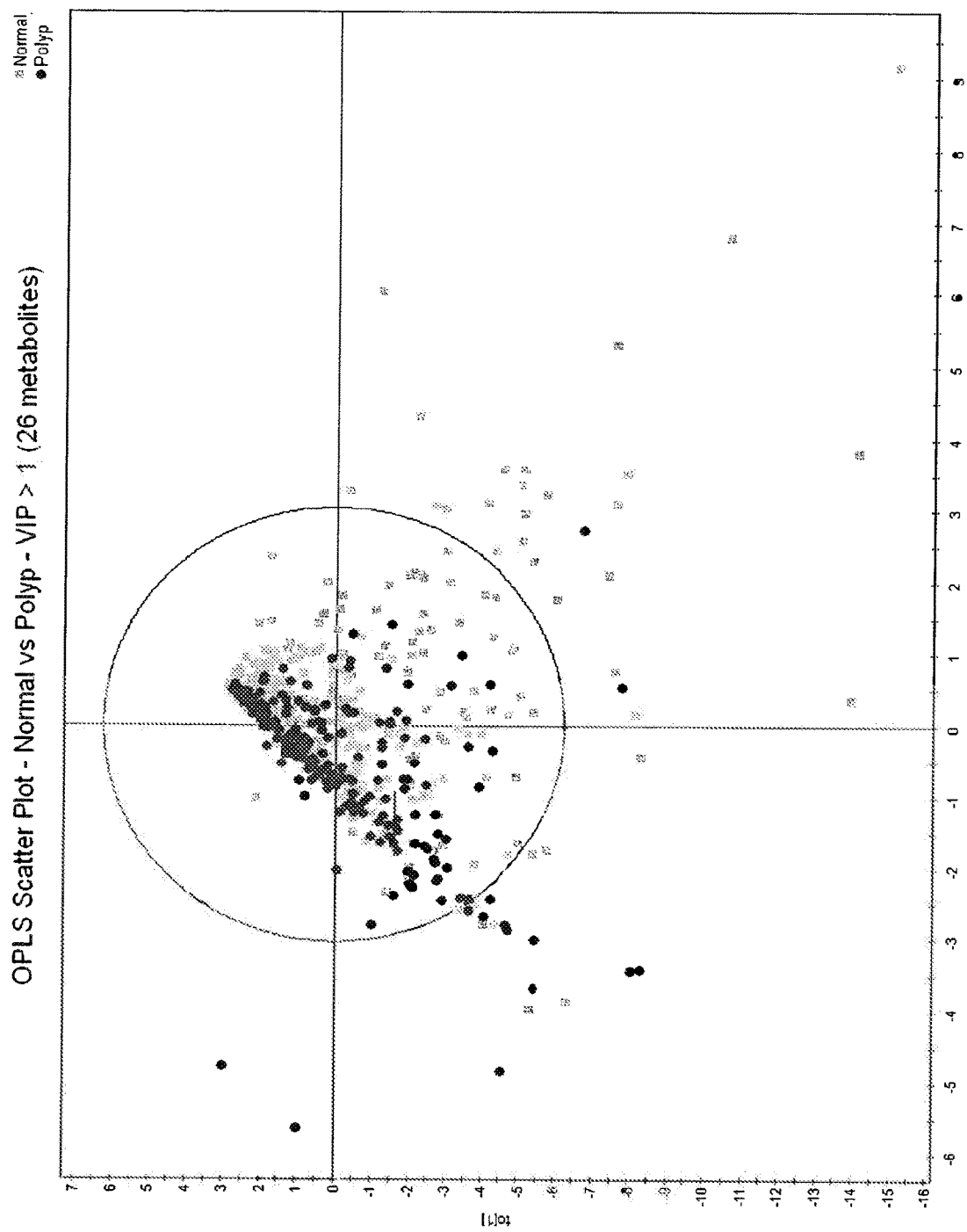
FIG. 14 is a 2-dimensional OPLS plot of the data from urine samples obtained from subject without CRC and/or colorectal polyps (grey squares) compared to that from subjects having colorectal polyps (black diamonds) constructed from 26 metabolites with a VIP value higher than 1.

In the OPLS scatter plot, the normal group was in grey squares and the polyp group was in black diamonds. FIGS. 13 and 14 showed, even though there was an overlap between the two groups, that the polyp group clustered together and the normal group also clustered together, and they appeared on the different (right and left) sides of each plot.

Figure 15:
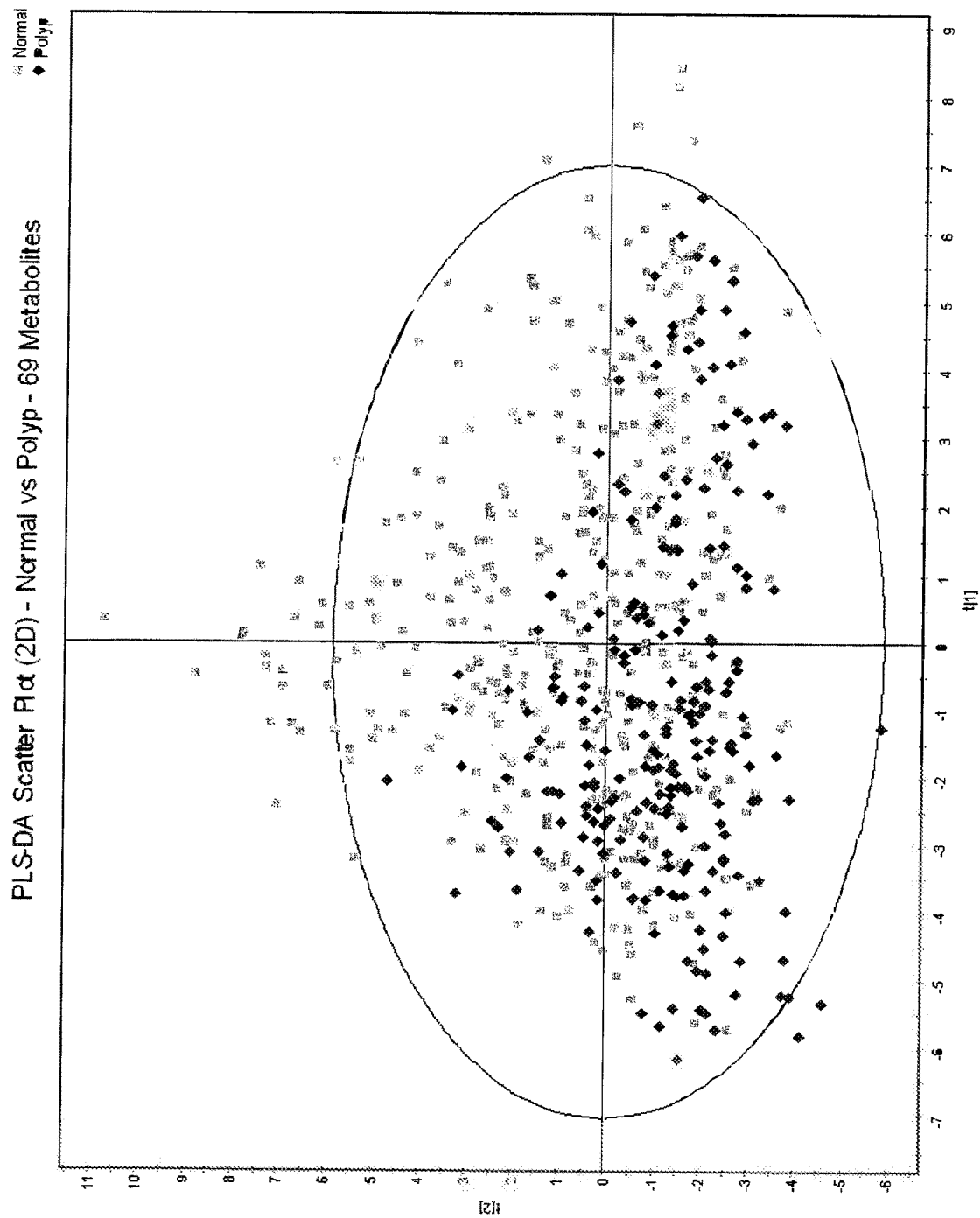
FIG. 15 is a 2-dimensional PLS-DA scatter plot of the data from urine samples obtained from subjects without CRC and/or colorectal polyps (grey squares) compared to that from subject having colorectal polyps (black diamonds) constructed from 69 metabolites.
Figure 16:
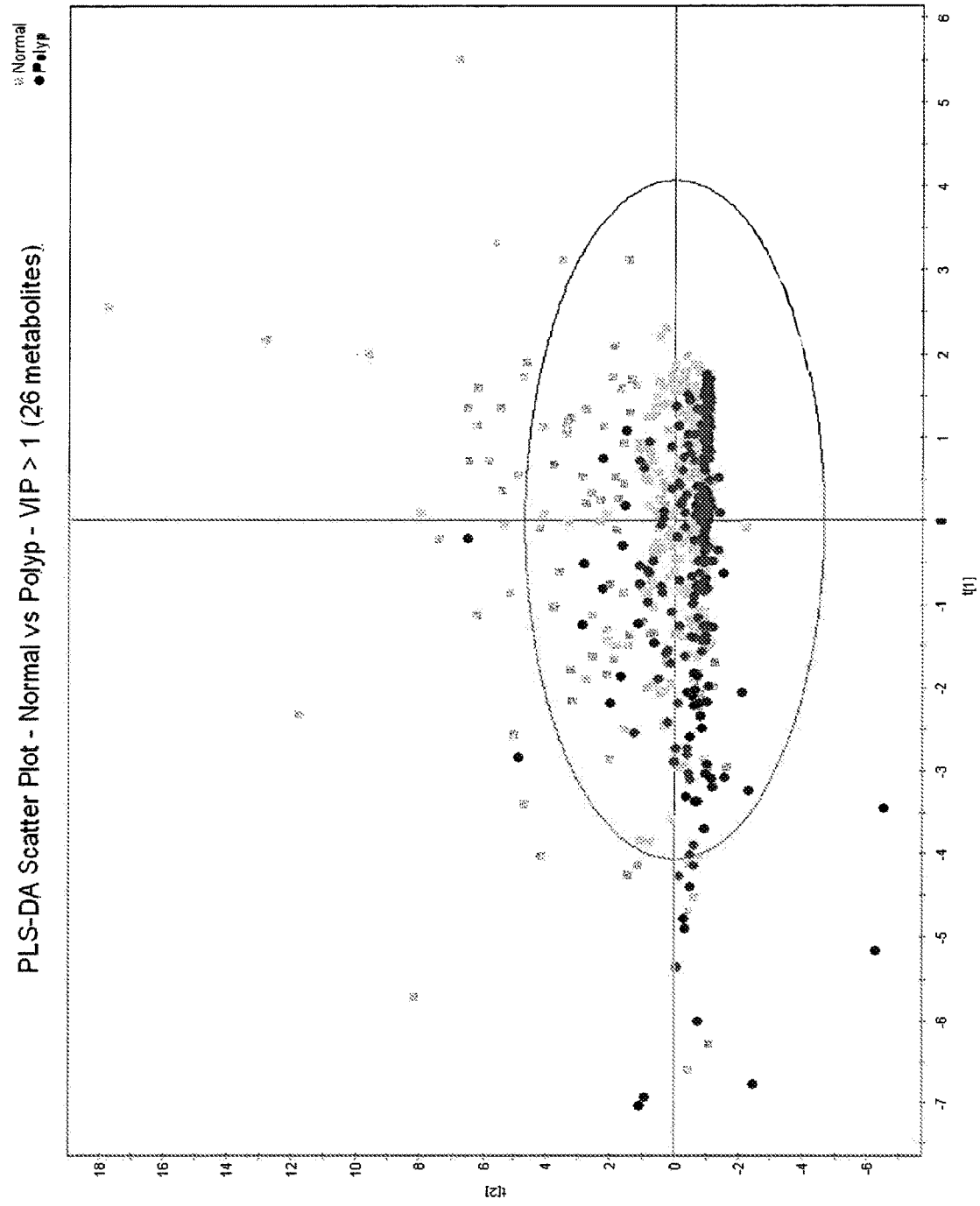
FIG. 16 is a 2-dimensional PLS-DA scatter plot the data from urine samples obtained from subjects without CRC and/or colorectal polyps (grey squares) compared to that from subject having colorectal polyps (black diamonds) constructed from 26 metabolites with a VIP value higher than 1.

In the PLS-DA scatter plot, the normal group was in grey squares and the polyp group was in black diamonds. FIGS. 15 and 16 showed, even though there was an overlap between the two groups, similarly to the OPLS scatter plot, the polyp group clustered together on the top of the plot and the normal group clustered together on the bottom.

From Table 4, a sensitivity range of 94-57% and specificity range of 40-78% would be achieved with a cut-off range of 0.25-0.45. In the setting of a screening test, a low FN rate is more important than a low FP rate, hence higher sensitivity could be achieved at the expense of a lower specificity. In this case, a cut-off of 0.3 could be used to achieve a sensitivity of 88% and a specificity of 51%. In contrast, preliminary analysis of fifty-two subjects of the normal and the polyp group samples that showed FOBT had a sensitivity of 9% and specificity of 100%.

Figure 19:
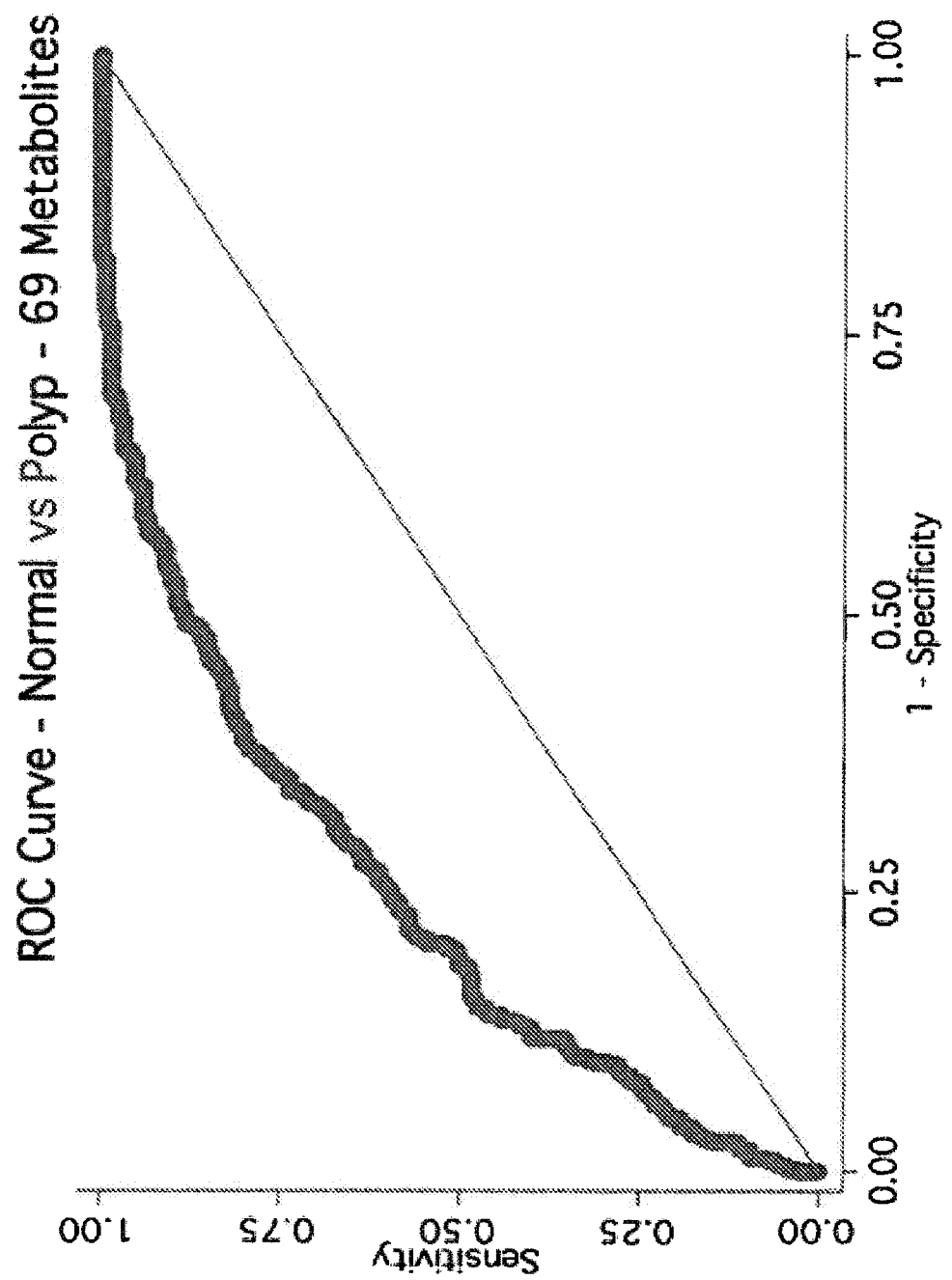
FIG. 19 is a ROC curve of the OPLS model of FIG. 13.
Figure 20:
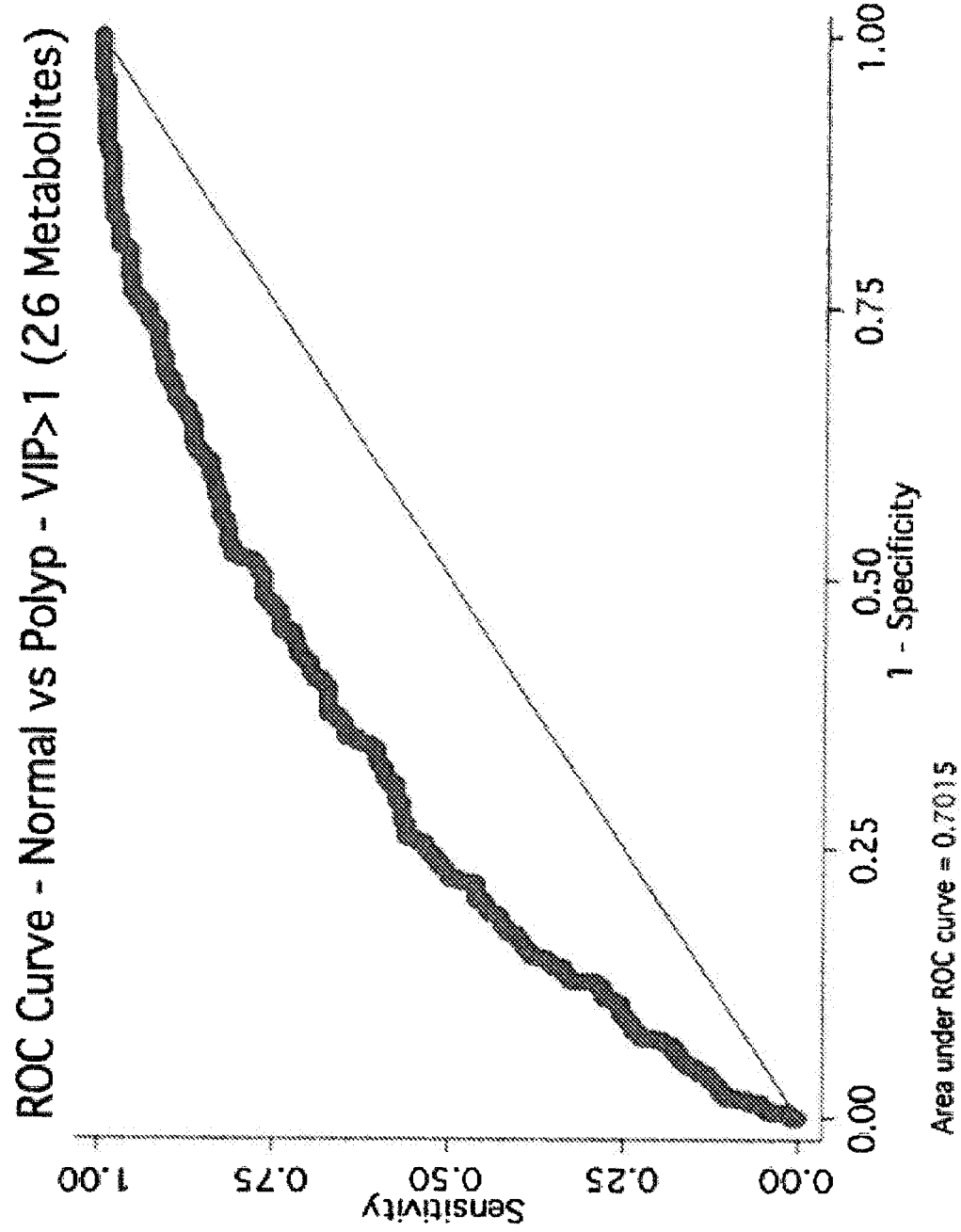
FIG. 20 is a ROC curve of the OPLS model of FIG. 14.

The ROC curves in FIGS. 19 and 20 had the AUC scores of 0.7673 and 0.7015, respectively. This result showed that the metabolite profile consisting of 26 metabolites out of 69, with higher VIP value than 1, can also be used to assess whether a subject has colorectal polyps, though the metabolite profile consisting of 69 metabolites might provide more accurate assessment. Table 4 also demonstrates that even five metabolites with highest VIP values could be used to assess whether a subject has or is predisposed to developing colorectal polyps.

Example 3. Assessment of Adenoma Polyp Group Versus Normal Group

Subjects for the normal group and the adenoma group were recruited from a population based study of 1,200 asymptomatic subjects who were supposed to be exposed to an average or high risk of CRC, based on family history of CRC or personal history of colorectal polyps.

Four hundred forty four healthy subjects without CRC and/or colorectal polyps were selected and classified as the normal group. The adenoma group consisted of one hundred sixty two subjects with adenomatous polyp. Clinical information was obtained from study questionnaires, and subjects completed a medical questionnaire, had a FOBT, FIT, and a colonoscopy for determination of classification.

The process as described previously in "Assessment of Cancer Group versus Normal Group" was followed for urine sample collection, treatment of the sample, NMR acquisition, and analysis of the data obtained.

Over 240 metabolites were considered, and 72 were found to be significant, that is, the spectral peaks of 72 metabolites in the compound library were identified in the spectra of the study samples: 1,6-Anhydro-β-D-glucose, 1-Methylnicotinamide, 2-Hydroxyisobutyrate, 2-Oxoglutarate, 3-Aminoisobutyrate, 3-Hydroxybutyrate, 3-Hydroxyisovalerate, 3-Hydroxymandelate, 3-Hydroxyphenylacetate, 3-Indoxyl sulfate, 4-Hydroxyphenylacetate, Acetate, Acetone, Adipate, Alanine, Ascorbate, Asparagine, Benzoate, Betaine, Butyrate, Carnitine, Citrate, Creatine, Creatinin, DSS (Chemical Shape Indicator), Dimethylamine, Ethanol, Formate, Galactose, Glucose, Glutamine, Glycerol, Glycine, Glycolate, Guanidoacetate, Hippurate, Histidine, Hypoxanthine, Ibuprofen, Isoleucine, Lactate, Leucine, Lysine, Mannitol, Methanol, Methylguanidine, N,N-Dimethylglycine, O-Acetylcarnitine, Pantothenate, Propylene glycol, Pyroglutamate, Pyruvate Salicylurate, Serine, Succinate, Sucrose, Tartrate, Taurine, Threonine, Trigonelline, Trimethylamine, Trimethylamine N-oxide, Tyrosine, Uracil, Urea, Valine, Xylose, cis-Aconitate, trans-Aconitate, β-Alanine, Π-Methylhistidine, T-Methylhistidine.

Metabolite concentrations were log transformed to normalize the concentrations. Those metabolites that were not products of normal human metabolism, i.e. xenobiotics, such as ibuprofen and salicylurate, were excluded. The internal standard DSS was also excluded in the analysis, and 69 metabolites were obtained as a reference metabolite profile.

The metabolites identified with a VIP score of greater than one are Butyrate, Serine, Asparagine, Π-Methylhistidine, 3-Hydroxybutyrate, Methanol, 3-Hydroxymandelate, Tyrosine, Trigonelline, β-Alanine, Histidine, Dimethylamine, Urea, 1-6-Anhydro-β-D-glucose, Glucose, Ethanol, Benzoate, Acetone, Threonine, 2-Hydroxyisobutyrate, Creatinine, 3-Hydroxyphenylacetate, 3-Indoxyl sulfate, hippurate, Ascorbate, 4-Hydroxyphenylacetate. The result was summarized in Table 5 together with the list of 69 metabolites.

The following analysis was performed with two different metabolite profiles, one with all the 69 important metabolites, and the other with 17 metabolites with a VIP value higher than 1.

Figure 21:
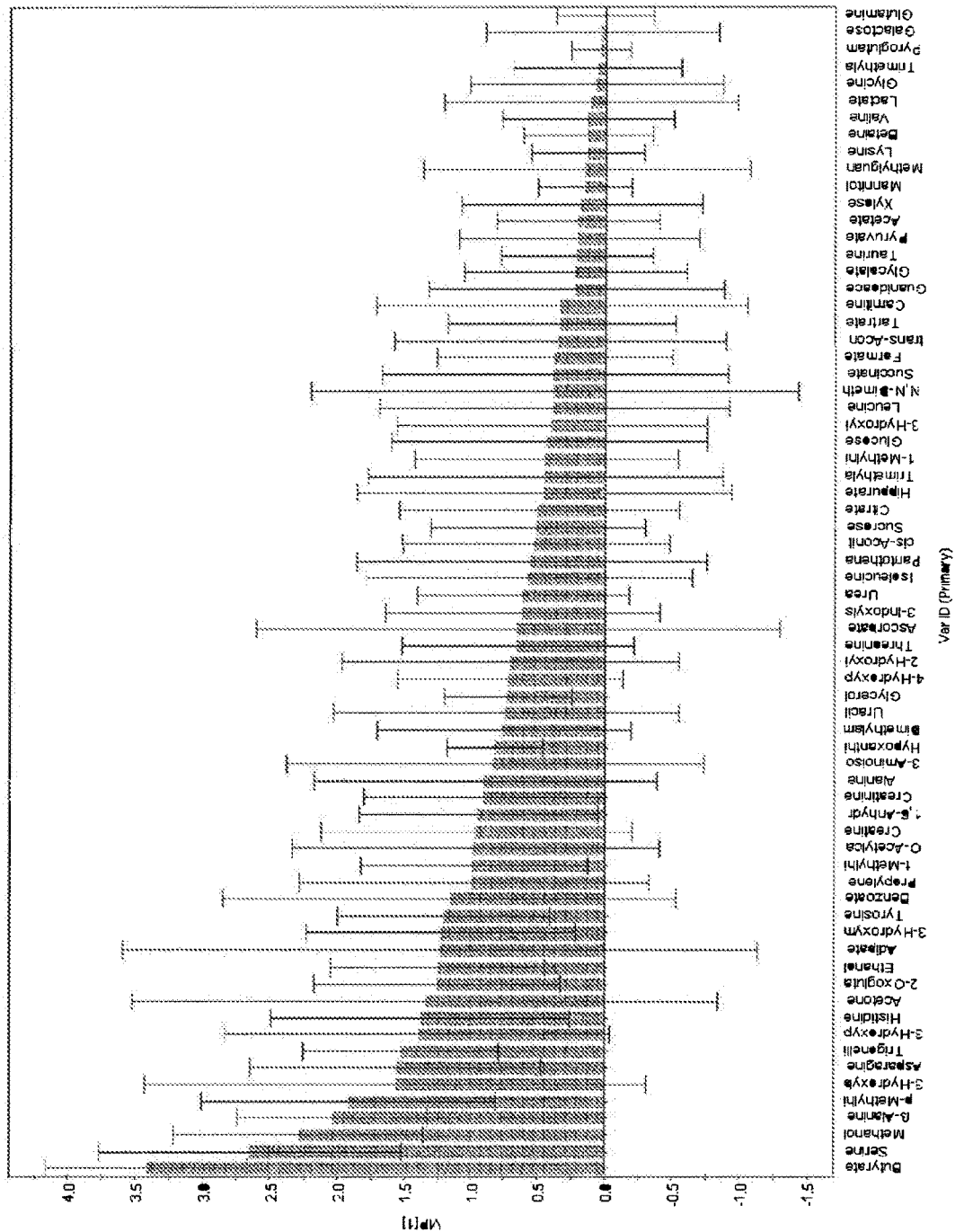
FIG. 21 is a VIP plot of analyzed metabolites in order of their contribution to the separation between the data from urine samples obtained from subjects without CRC and/or colorectal polyps and that from the group of subjects having adenomatous polyps for 69 metabolites.
Figure 22:
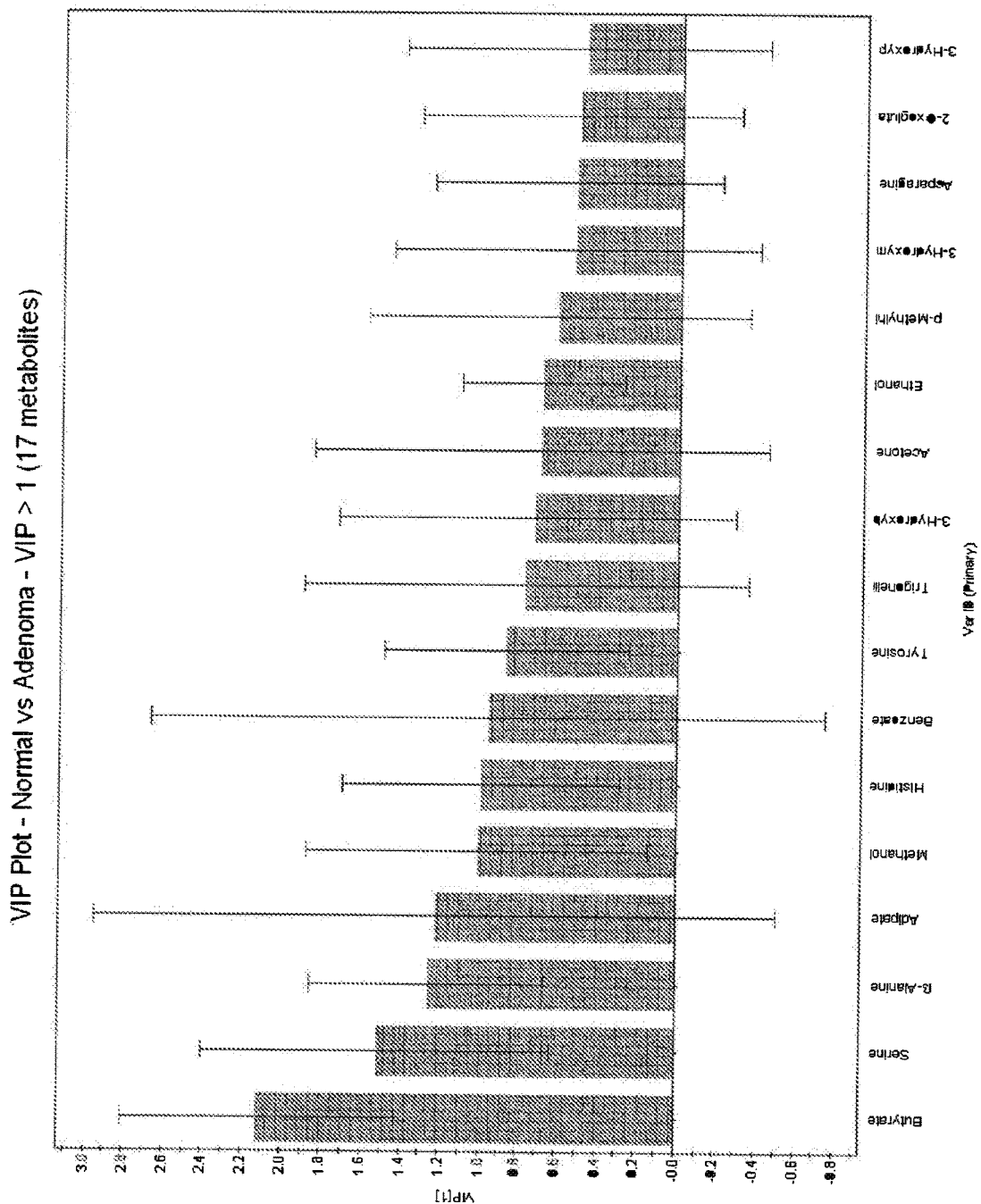
FIG. 22 is a VIP plot of analyzed metabolites in order of their contribution to the separation between the data from urine samples obtained from subjects without CRC and/or colorectal polyps and that from subjects having adenomatous polyps for 17 metabolites with a VIP value higher than 1.
Figure 24:
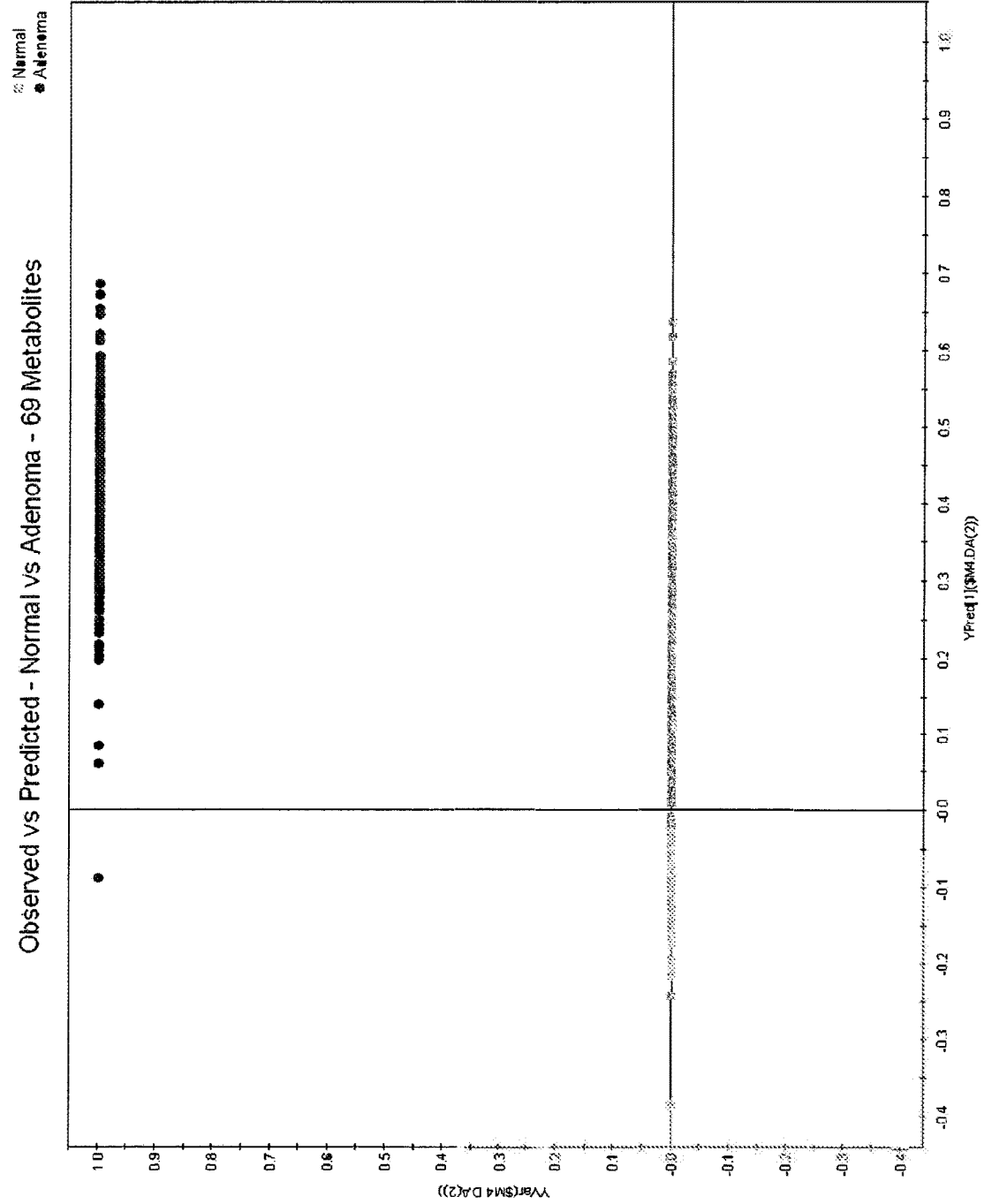
FIG. 24 is an observed versus predicted plot of the OPLS model of FIG. 23. Data from urine samples obtained from subjects without CRC and/or colorectal polyps are displayed as grey squares and that from subjects having adenomatous polyps are displayed as black diamonds.
Figure 25:
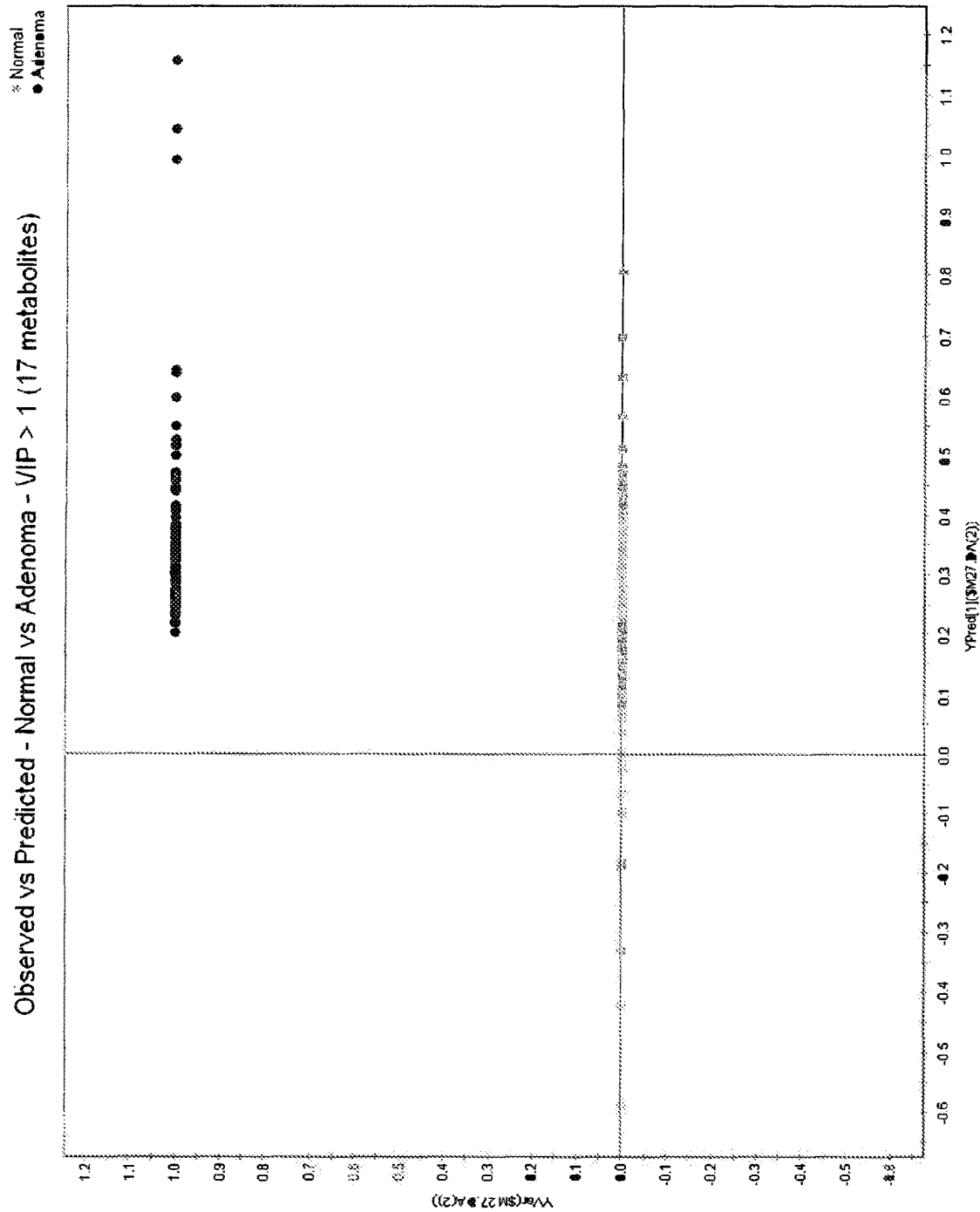
FIG. 25 is an observed versus predicted plot of the OPLS model of the 2-dimensional OPLS plot with 17 metabolites with a VIP value higher than 1. The 2-dimensional OPLS plot was prepared based on the data from urine samples obtained from subjects without CRC and/or colorectal polyps compared to that from subjects having adenomatous polyps. Data from urine samples obtained from subjects without CRC and/or colorectal polyps are displayed as grey squares and that from subjects having adenomatous polyps are displayed as black diamonds.

The VIP plots were generated to illustrate which metabolites contribute the most to the separation between the normal and adenoma groups (FIGS. 21 and 22). The resulting OPLS (FIG. 23), PLS scatter plots (not shown), observed vs. predicted plots (FIGS. 24 and 25), ROC curve (FIGS. 26 and 27), and sensitivity & specificity data (Table 6) were produced.

Figure 23:
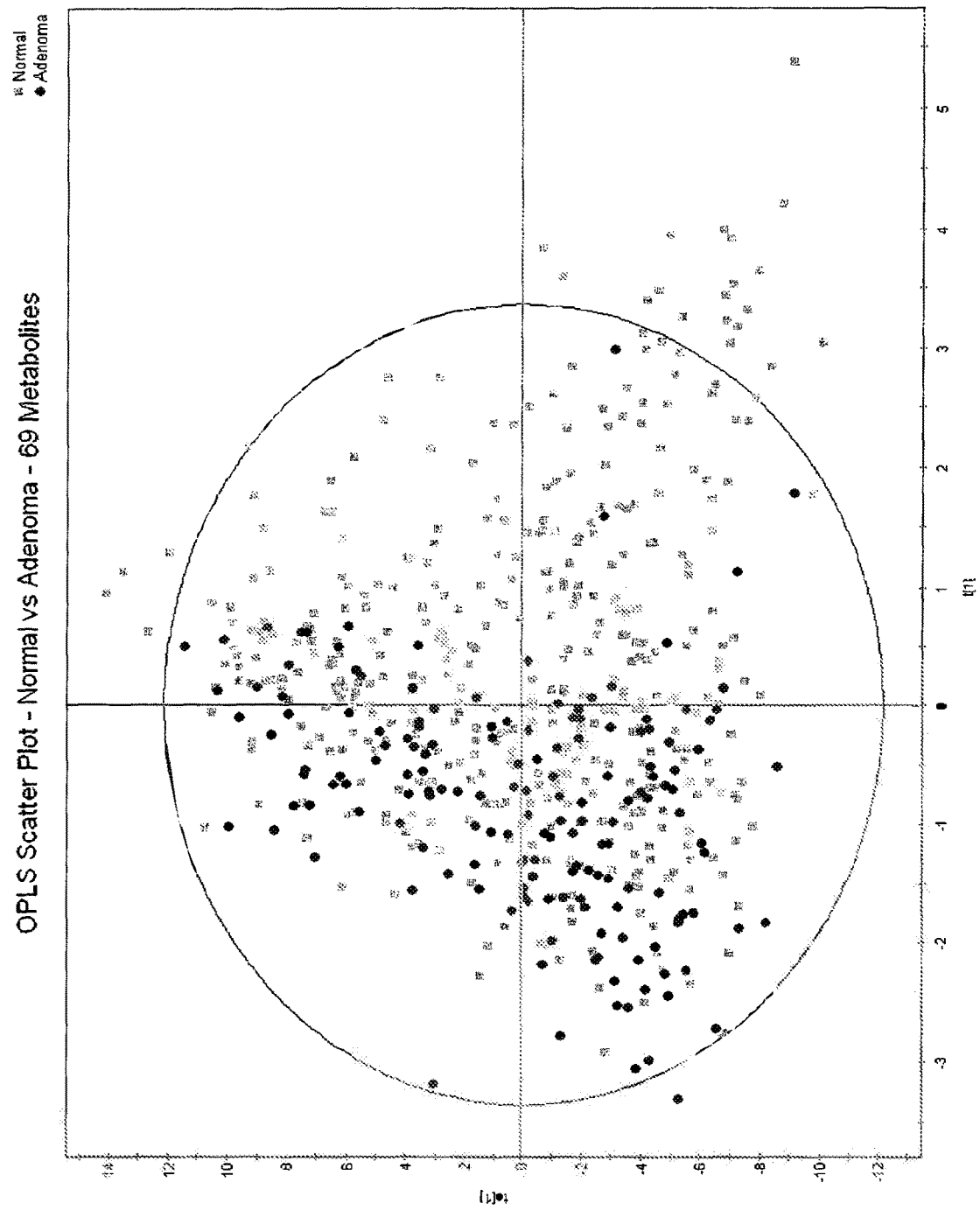
FIG. 23 is a 2-dimensional OPLS plot of the data from urine samples obtained from subjects without CRC and/or colorectal polyps (grey squares) compared to that from subjects having adenomatous polyps (black diamonds) constructed from 69 metabolites.

In the OPLS scatter plot, the normal group is in grey squares and the polyp group is in black diamonds. FIG. 23 shows, even though there is an overlap between the two groups, that the polyp group clusters together and the normal group also clusters together, and they appear on the different (right and left) sides of the plot. The OPLS scatter plot for 17 metabolites with a VIP value higher than 1 is not shown.

In the PLS-DA scatter plot, the normal group is in grey squares and the polyp group is in black diamonds. Even though there is an overlap between the two groups, similarly to the OPLS scatter plot, the polyp group clusters together on the top of the plot and the normal group clusters together on the bottom.

From Table 6, a sensitivity range of 65.55-5.88% and specificity range of 50.71-98.58% would be achieved with a cut-off range of 0.329791-0.577397 for the metabolites with a VIP score greater than 1. In the setting of a screening test, a low FN rate is more important than a low FP rate, hence higher sensitivity could be achieved at the expense of a lower specificity. In this case, a cut-off of 0.329791 could be used to achieve a sensitivity of 65.55% and a specificity of 50.71%. In contrast, preliminary analysis of fifty-two normal and colorectal polyps samples that showed FOBT had a sensitivity of 9% and specificity of 100%.

Figure 26:
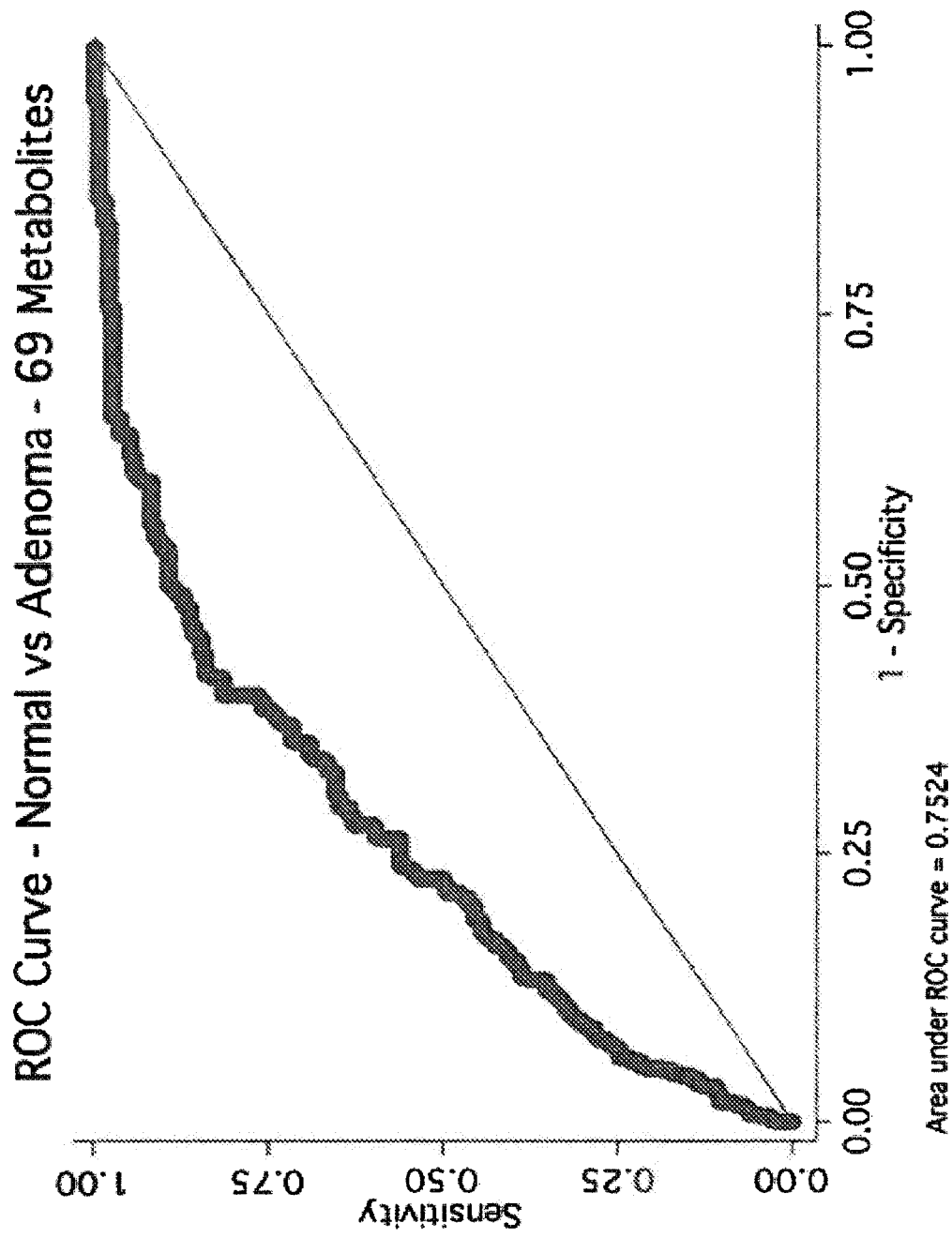
FIG. 26 is a ROC curve of the OPLS model of FIG. 23.
Figure 27:
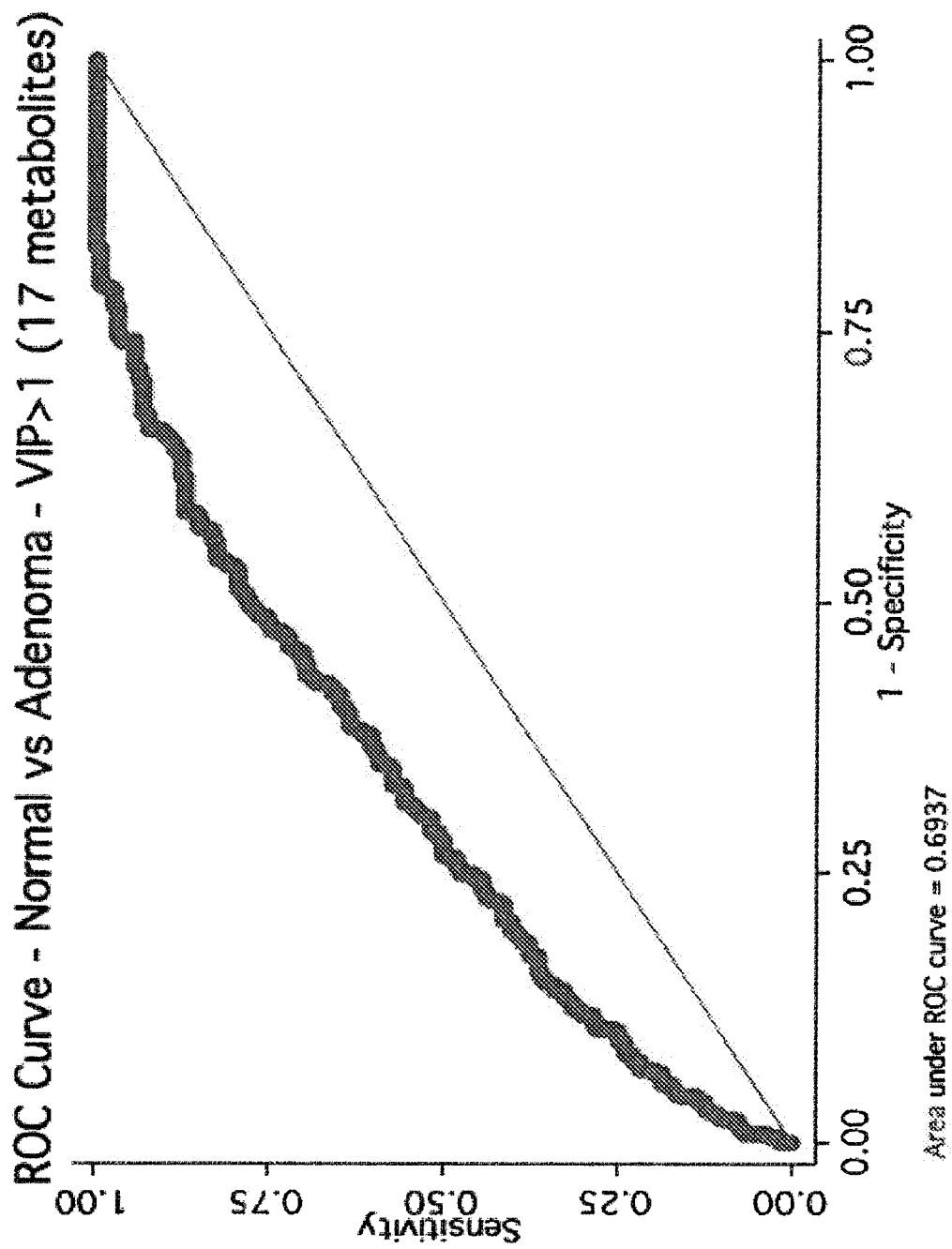
FIG. 27 is a ROC curve of the OPLS model of the 2-dimensional OPLS plot with 17 metabolites with a VIP value higher than 1. The 2-dimensional OPLS plot was prepared based on the data from urine samples obtained from subjects without CRC and/or colorectal polyps compared to that from subjects having adenomatous polyps.
Figure 28:
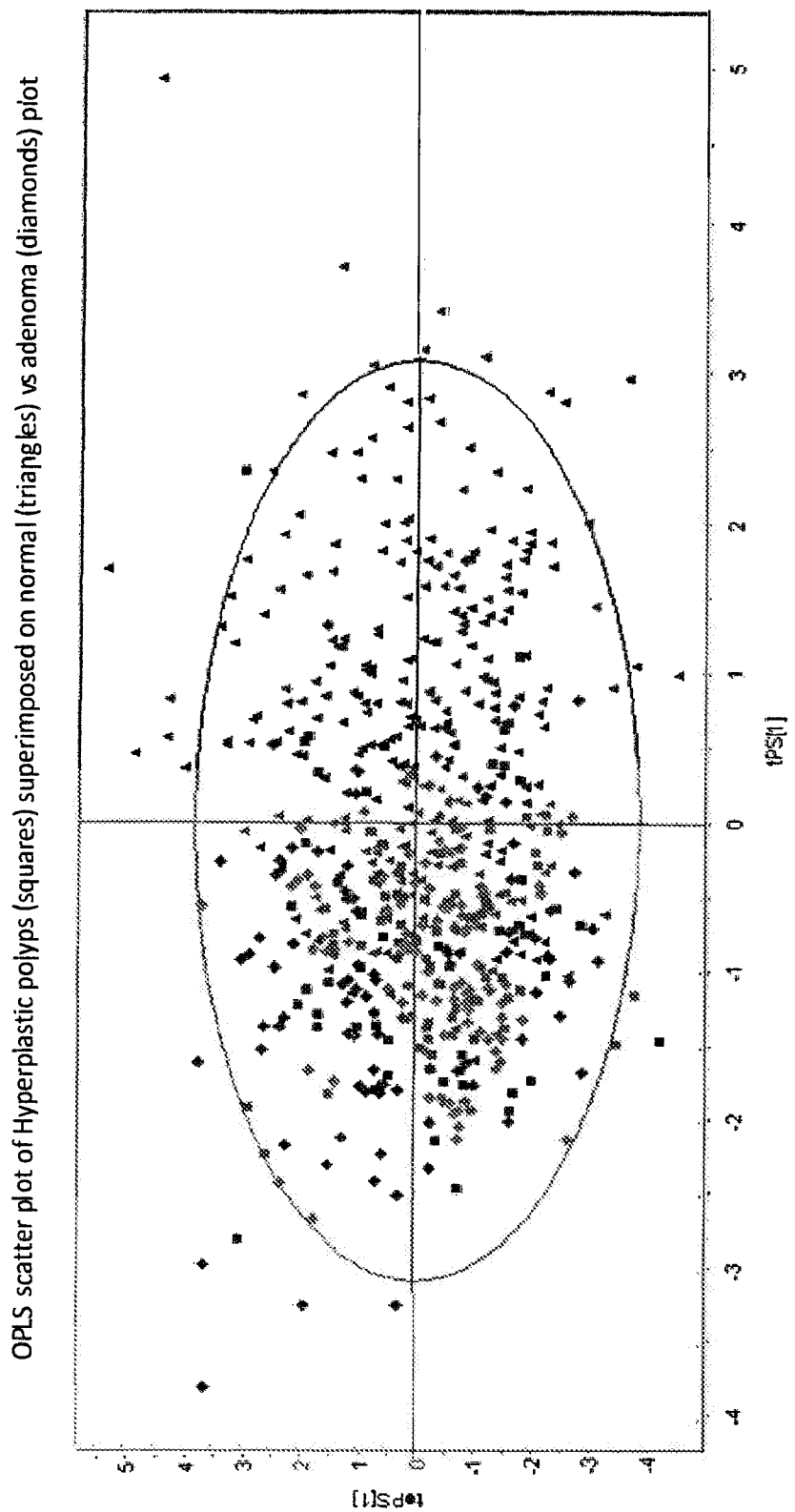
FIG. 28 is a 2-dimensional OPLS plot based on the data from urine samples obtained from subjects without CRC and/or colorectal polyps (triangles) compared to that from subjects having adenomatous polyps (diamonds), superimposed with that from subjects having hyperplastic polyps (squares), constructed from 69 metabolites.

The ROC curves in FIGS. 26 and 27 had the AUC scores of 0.7524 and 0.6937, respectively. This result showed that the metabolite profile consisting of 17 metabolites out of 69, with higher VIP value than 1, can also be used to assess whether a subject has adenomatous polyps, though the metabolite profile consisting of 69 metabolites might provide more accurate assessment. Table 6 also demonstrates that even five metabolites with highest VIP values could be used to assess whether a subject has or is predisposed to developing adenomatous polyps.

Example 4. Assessment of Adenoma Polyp Group Versus Hyperplastic Polyp Group

A total of 110 urine samples from subjects with hyperplastic polyps were introduced blindly to the Normal versus Adenoma model discussed in Example 3. The analysis result showed that the metabolite profile of hyperplastic polyps was more alike with the adenomatous group's than the normal group's (FIG. 29). This was further confirmed by an attempt to establish an OPLS model between hyperplastic polyps and adenomatous polyps. A meaningful model to separate the two groups could not be constructed ($R^2Y=0.126$, $Q^2=-0.0771$).

This result suggests that some of the hyperplastic polyps might be pre-cancerous like the adenomatous polyps and thus display a precancerous metabolomic fingerprint.

Example 5. Analytical Methods and their Application

Analytical Methods
PLS (Conventional):
Conventional PLS applies to the two-block (X/Y) regression problem. It uses X to construct a model of Y, where the objective is to predict the latter from the former for new samples in the prediction set. In that sense, PLS is unidirectional, i.e., X→Y, but not vice versa.

When X is composed of e.g. spectroscopic data, process readings or measurements from bioanalytical platforms, there is a risk that systematic variation may reside in X which is not linearly correlated with Y. Such variability in X is usually called Y-orthogonal variation. Although Y-orthogonal variation in X does not affect the predictive power of a PLS model, it may negatively affect model interpretation. The score-loading correspondence is perturbed by the presence of Y-orthogonal variation in X.

OPLS:
The OPLS method is a recent modification of the PLS method, which is designed to handle variation in X that is orthogonal to Y. It is an extension to the supervised PLS regression method with an integrated Orthogonal signal correction (OSC) filter, which removes the uncorrelated signals resulting in information of the within-class variation. OPLS separates the systematic variation in X into two parts, one that is linearly related (and therefore predictive) to Y and one that is orthogonal to Y. The predictive variation of Y in X is modeled by the predictive components. The variation in X which is orthogonal to Y is modeled by the orthogonal components. This partitioning of the X-data provides improved model transparency and interpretability, but does not change the predictive power. Similarly to PLS, OPLS is a unidirectional method, where the scope is the relation X→Y.

OPLS Scatter Plot:
The scatter plot is of the OPLS model.
O2PLS:
O2PLS is a generalization of OPLS. In contrast to PLS and OPLS, O2PLS is bidirectional, i.e. X←→Y, and therefore X can be used to predict Y, and Y can be used to predict X. Additionally, with O2PLS it is possible to partition the systematic variability in X and Y into three parts, (i) the X/Y joint predictive variation, (ii) the Y-orthogonal variation in X, and (iii) the X-unrelated variation in Y.

Figure 30:
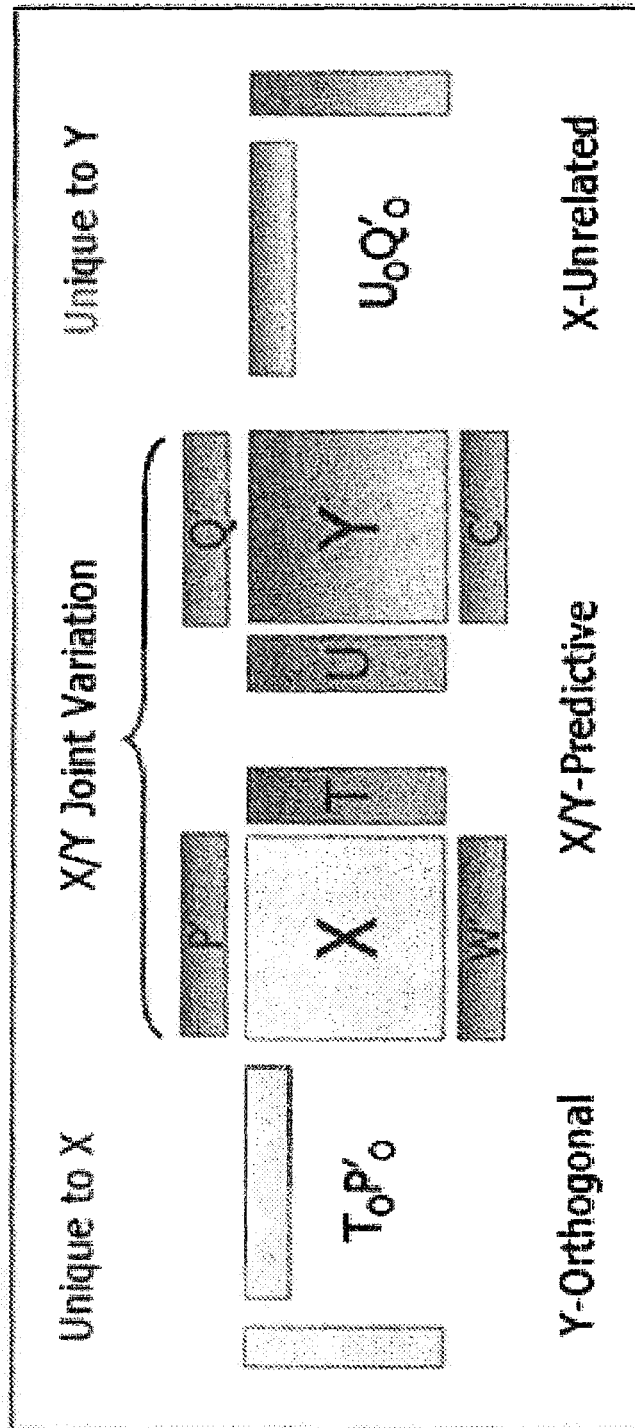
FIG. 30 is an overview of the O2PLS model relating two data tables to each other.

FIG. 30 is an overview of the O2PLS model relating two data tables to each other. The Y-orthogonal variation in X (left-hand side of the Figure) represents the variation of the observations in X that is varying orthogonally to the corresponding structure in Y. This variation is unique to X. The X/Y joint predictive variation (middle part of the Figure) describes the predictive variation between X and Y, the information overlap. The X-unrelated variation in Y (right-hand side of the Figure) corresponds to the variation of the observations in Y that is varying orthogonally to the corresponding structure in X. This variation is unique to Y.

The ability to interpret the X/Y joint predictive variation separated from the non-correlated variation implies that the model interpretation is refined and simplified. Furthermore, it should be noted that for the single-y case the OPLS and O2PLS methods are identical. For such a model there can only be one predictive component expressing the joint X/Y predictive variation.

PLS-DA Scatter Plot:
This scatter plot is of the partial least squares discriminant analysis (PLS-DA) model. Conventional PLS is used where a quantitative relationship exists between two data tables X & Y; it uses X to construct a model of Y, where the objective is to predict Y from the X for new samples in the prediction set. It is another statistical method used to compress multi-dimensional and complex data sets into a more manageable dataset.

Observed Vs. Predicted Plot:
The observed vs. predicted plot displays the observed values vs. the fitted or predicted values for the selected response. The observed vs. predicted plot is a scatter plot of the Y variables (which are normal vs. cancer, adenoma, or polyps) verses the predicted values. The observed vs. predicted plot provides with Y predicted values, as assigned by the model, for each sample along with their observed (normal or cancer/adenoma/polyp) value. Then, these values are taken to generate a ROC curve. The observed vs. predicted plot also allows to determine the true positives, false positives, true negatives, and false negatives, to calculate sensitivity and specificity with a range of cut-offs, and to view the overlap present between two groups.

Roc Curve:

The receiver operating characteristic (ROC) Curve is a graphical representation of the spectrum of sensitivities and specificities generated using the various cut-offs, using the sensitivity as the y-axis and 1-specificity as the x-axis. Area under the ROC curve (AUC) reflects the accuracy of the test and is displayed on the left lower corner of the plot. An AUC of 0.9 to 1 represents an excellent diagnostic test whereas an AUC of 0.8-0.9 represents a good test and an AUC of 0.7 to 0.8 represents a fair test.

VIP Plot:

Variable Importance in the Projection (VIP) plot allows to identify which metabolites have a greater impact on driving the separation between groups in models. Each metabolite used to construct models is assigned a VIP score; this score is assigned through a statistical formula that is used to calculate the influence of each model. The higher the VIP score, the greater the influence of the metabolite with the score on shaping the model. VIP also allows for the comparison of one metabolite to another. Terms with a large VIP (greater then 1) are said to be the most relevant for explaining 'Y'.

Analytical Methods Used

OPLS and PLS-DA Scatter Plot:

The orthogonal PLS named O2PLS has been implemented in SIMCA-P+ 12. O2PLS is bidirectional, i.e. X←→Y, and therefore X can be used to predict Y, and Y can be used to predict X. For the single-y case the OPLS and O2PLS methods are identical.

The O2PLS model can be written as:

$$X = T_P P'_P + T_O P'_O + E \text{(for model of } X\text{)} \qquad (1)$$

$$Y = U_P Q'_P + U_O Q'_O + F \text{(for model of } Y\text{)} \qquad (2)$$

where a linear relationship exists between $T_P$ and $U_P$. Here, the score vectors in $T_P$ and $T_O$ are mutually orthogonal. The number of components in the respective set of components is determined using cross validation.

For any part of the OPLS/O2PLS model, the percentages explained and predicted variances can be obtained from plots and lists in the software. The vectors listed in Table 7 are unique for OPLS/O2PLS. These vectors in addition to the ones listed for PLS are computed for each component.

ROC Curve (Receiver Operating Characteristic):

ROC curves were generated using STATA 10.0 (College Station, Tex.), along with the ROC curves a complete sensitivity and specificity report was also generated. The ROC curve is a fundamental tool for diagnostic test evaluation. In a ROC curve the true positive rate (Sensitivity) is plotted in function of the false positive rate (100-Specificity) for different cut-off points of a parameter. Each point on the ROC curve represents a sensitivity/specificity pair corresponding to a particular decision threshold. The area under the ROC curve is a measure of how well a parameter can distinguish between two diagnostic groups (diseased/normal).

The diagnostic performance of a test, or the accuracy of a test to discriminate diseased cases from normal cases is evaluated using Receiver Operating Characteristic (ROC) curve analysis. ROC curves can also be used to compare the diagnostic performance of two or more laboratory or diagnostic tests.

A test result comparing two populations, for example, one with a disease and the other without the disease, a perfect separation between the two groups is rarely observed. Indeed, the distribution of the test results will overlap, as shown in the following figure. Therefore, when a cut-off point or criterion value to discriminate between the two populations is selected and applied, there will be some cases with the disease correctly classified as positive (TP=True Positive fraction), but some cases with the disease will be classified negative (FN=False Negative fraction). On the other hand, some cases without the disease will be correctly classified as negative (TN=True Negative fraction), but some cases without the disease will be classified as positive (FP=False Positive fraction). In a Receiver Operating Characteristic (ROC) curve the true positive rate (Sensitivity) is plotted in function of the false positive rate (100−Specificity) for different cut-off points. Each point on the ROC curve represents a sensitivity/specificity pair corresponding to a particular decision threshold. A test with perfect discrimination (no overlap in the two distributions) has a ROC curve that passes through the upper left corner (100% sensitivity, 100% specificity). Therefore the closer the ROC curve is to the upper left corner, the higher the overall accuracy of the test.

VIP Plot:

SIMCA-P+ computes the influence on Y of every term ($x_k$) in the model, called VIP (variable importance in the projection). VIP is the sum over all model dimensions of the contributions VIN (variable influence). For a given PLS dimension, a, $(VIN)_{ak}^2$ is equal to the squared PLS weight $(w_{ak})^2$ of that term, multiplied by the explained SS of that PLS dimension. The accumulated (over all PLS dimensions) value is:

$$VIP_{ak}^2 = \Sigma (VIN)_k^2$$

where the summation is made over a=1 to A. This value is then divided by the total explained SS by the PLS model and multiplied by the number of terms in the model. The final VIP is the square root of that number. The formula can also be expressed as:

$$VIP_{Ak} = \sqrt{\sum_{a=1}^{A} (w_{ak}^2 * (SSY_{a-1} - SSY_a)) * \frac{K}{(SSY_a - SSY_A)}}$$

The Sum of squares of all VIP's is equal to the number of terms in the model hence the average VIP is equal to 1. One can compare the VIP of one term to the others. Terms with large VIP, larger than 1, are the most relevant for explaining Y. The VIP plot shows which are the most important variables over the model as a whole.

The VIP plot carries similar information to the coefficients plot and in practical terms the two plots often look very similar. The major difference is that the VIP plot describes which X variables characterize the X block well AND which variables correlate with Y. PLS is a dual technique which tries to finds directions in X which both characterize X well and are related to Y. In extreme cases, it is possible for an X variable to have a high VIP but not be related to Y at all.

The VIP values summarize the overall contribution of each X-variable to the PLS model, summed over all components and weighted according to the Y variation accounted for by each component, therefore you only ever get one VIP plot per model.

Support Vector Machines (SVM):

Classifiers were built using Support Vector Machines (SVM). SVMs separate the Polyp vs Normal data points in n-dimensional space (where n is the number of features) such that the margin of separation is maximized. We built a linear SVM, which means that a linear equation is created:

$$\mathrm{prediction}(x) = w_1 * x_1 + w_2 * x_2 + \ldots + w_a * x_a - b$$

The xi values are the individual values of the feature vector for a subject (as described in the "Classification" section). The wi values are the weight values that are found by the SVM algorithm, along with the b parameter that helps fit the equation to the data set.

TABLE 1

VIP scores (Normal group vs. CRC group) with concentration analysis (concentrations in μM)

| | VIP | Normals | | | | Cancer | | | | Higher in | Higher in |
|---|---|---|---|---|---|---|---|---|---|---|---|
| Var ID (Primary) | score | min | max | mean | median | min | max | mean | median | Normal | Cancer |
| Adipate | 3.93 | 0.0 | 103.9 | 1.3 | 0.0 | 0.0 | 8645.5 | 218.1 | 0.0 | | x |
| 3-Hydroxybutyrate | 2.25 | 0.0 | 498.4 | 11.7 | 0.0 | 0.0 | 3075.7 | 157.0 | 0.0 | | x |
| Creatine | 1.96 | 0.0 | 15102.4 | 2099.7 | 1563.5 | 0.0 | 13477.6 | 2280.7 | 1339.0 | | x |
| Guanidoacetate | 1.95 | 0.0 | 1781.0 | 204.0 | 143.0 | 0.0 | 2857.9 | 232.0 | 148.9 | | x |
| Dimethylamine | 1.82 | 193.0 | 24617.4 | 5643.3 | 4234.9 | 716.0 | 35527.5 | 8175.9 | 6212.0 | | x |
| Hypoxanthine | 1.66 | 0.0 | 2108.5 | 208.4 | 106.5 | 0.0 | 1240.1 | 188.4 | 144.1 | x | |
| Benzoate | 1.64 | 0.0 | 567.3 | 3.5 | 0.0 | 0.0 | 1130.9 | 35.0 | 0.0 | | x |
| O-Acetylcarnitine | 1.60 | 0.0 | 131.3 | 24.7 | 17.5 | 0.0 | 168.2 | 30.0 | 21.3 | | x |
| Pyruvate | 1.56 | 0.0 | 539.8 | 35.4 | 10.0 | 0.0 | 341.2 | 28.4 | 8.0 | x | |
| Methanol | 1.52 | 0.0 | 4738.5 | 224.5 | 0.0 | 0.0 | 2783.6 | 215.9 | 0.0 | x | |
| Lactate | 1.28 | 0.0 | 31.5 | 4.1 | 0.0 | 0.0 | 90.0 | 8.2 | 0.0 | | x |
| Creatinine | 1.26 | 0.0 | 10201.1 | 331.0 | 58.1 | 0.0 | 1245.5 | 109.8 | 0.0 | x | |
| Xylose | 1.22 | 7.1 | 8301.4 | 308.6 | 163.1 | 9.9 | 1554.7 | 364.0 | 237.0 | | x |
| 3-Indoxylsulfate | 1.19 | 0.0 | 1317.6 | 120.5 | 82.5 | 0.0 | 1207.0 | 209.1 | 135.5 | | x |
| Trigonelline | 1.13 | 0.0 | 474.7 | 78.5 | 48.7 | 0.0 | 450.6 | 99.6 | 60.2 | | x |
| Taurine | 1.06 | 0.0 | 536.6 | 39.0 | 22.5 | 0.0 | 416.3 | 43.3 | 18.7 | | x |
| Threonine | 1.04 | 0.0 | 888.3 | 45.5 | 13.4 | 0.0 | 715.5 | 79.1 | 35.0 | | x |
| p-Methylhistidine | 1.04 | 0.0 | 113.8 | 20.3 | 14.2 | 0.0 | 164.9 | 25.7 | 18.0 | | x |
| Glucose | 1.03 | 0.0 | 614.8 | 12.8 | 0.0 | 0.0 | 460.6 | 7.4 | 0.0 | x | |
| 4-Hydroxyphenylacetate | 1.01 | 0.0 | 1401.1 | 72.6 | 48.8 | 0.0 | 856.0 | 102.7 | 57.9 | | x |
| 1,6-Anhydro-I$^2$-D-glucose | 0.98 | 0.0 | 2763.6 | 35.7 | 13.8 | 0.0 | 140.4 | 27.8 | 18.1 | x | |
| Sucrose | 0.91 | 0.0 | 982.2 | 87.7 | 0.0 | 0.0 | 1419.5 | 96.3 | 0.0 | | x |
| 6-Alanine | 0.87 | 6976.6 | 441697.0 | 127007.5 | 111896.6 | 8573.4 | 324813.3 | 115212.8 | 99859.9 | x | |
| Formate | 0.86 | 0.0 | 27789.2 | 250.7 | 0.0 | 0.0 | 261.1 | 9.7 | 0.0 | x | |
| 3-Hydroxymandelate | 0.81 | 0.0 | 2539.3 | 60.0 | 0.0 | 0.0 | 750.9 | 37.4 | 0.0 | | |
| Trimethylamine N-oxide | 0.78 | 0.0 | 5028.3 | 283.2 | 132.2 | 0.0 | 2465.1 | 450.2 | 283.1 | | x |
| Carnitine | 0.76 | 0.0 | 907.1 | 47.8 | 22.7 | 0.0 | 972.1 | 85.5 | 36.4 | | x |
| Isoleucine | 0.76 | 0.0 | 1022.5 | 21.4 | 9.3 | 0.0 | 401.7 | 55.4 | 17.8 | | x |
| Valine | 0.72 | 0.0 | 66.4 | 9.5 | 6.5 | 0.0 | 217.1 | 12.8 | 5.4 | | x |
| Pantothenate | 0.69 | 0.0 | 321.3 | 20.3 | 11.6 | 0.0 | 752.2 | 57.6 | 19.5 | | x |
| Galactose | 0.66 | 5.1 | 772.6 | 121.1 | 96.0 | 13.8 | 3227.7 | 207.6 | 105.8 | | x |
| 3-Hydroxyphenylacetate | 0.66 | 0.0 | 188.6 | 11.9 | 0.0 | 0.0 | 249.2 | 10.7 | 0.0 | x | |
| Succinate | 0.62 | 0.0 | 282.0 | 17.9 | 10.7 | 0.0 | 481.1 | 34.8 | 19.4 | | x |
| Citrate | 0.58 | 0.0 | 864.8 | 140.3 | 79.4 | 0.0 | 1071.5 | 200.4 | 108.6 | | x |
| Leucine | 0.57 | 0.0 | 2897.0 | 97.8 | 52.0 | 3.8 | 2710.6 | 208.9 | 60.8 | | x |
| Trimethylamine | 0.54 | 0.0 | 4024.6 | 104.7 | 12.2 | 0.0 | 1883.9 | 119.2 | 5.7 | | x |
| 2-Oxoglutarate | 0.53 | 0.0 | 1256.7 | 56.2 | 27.0 | 0.0 | 409.9 | 53.9 | 12.8 | x | |
| N,N-Dimethylglycine | 0.52 | 0.0 | 415.5 | 29.4 | 17.3 | 0.0 | 188.3 | 27.7 | 18.0 | x | |
| Glycerol | 0.51 | 0.0 | 2004.7 | 149.7 | 81.6 | 0.0 | 1181.5 | 172.0 | 98.4 | | x |
| Lysine | 0.47 | 0.0 | 112.4 | 12.6 | 9.7 | 0.0 | 136.9 | 17.4 | 12.2 | | x |
| 1-Methylnicotinamide | 0.44 | 0.0 | 603.3 | 64.5 | 26.9 | 0.0 | 410.6 | 36.8 | 0.0 | x | |
| Ethanol | 0.42 | 8.2 | 1494.3 | 194.3 | 135.0 | 21.7 | 1317.2 | 329.7 | 247.2 | | x |
| Acetate | 0.41 | 0.0 | 12892.6 | 85.6 | 33.1 | 0.0 | 8769.3 | 268.5 | 45.9 | | x |
| Ascorbate | 0.39 | 0.0 | 12949.6 | 276.2 | 29.8 | 0.0 | 4539.5 | 237.3 | 0.0 | x | |
| Tyrosine | 0.39 | 0.0 | 976.3 | 71.2 | 48.9 | 0.0 | 298.4 | 64.4 | 36.4 | x | |
| t-Methylhistidine | 0.38 | 0.0 | 3078.9 | 77.0 | 0.0 | 0.0 | 2022.0 | 162.4 | 61.0 | | x |
| Urea | 0.37 | 0.0 | 4771.9 | 246.5 | 128.6 | 0.0 | 1125.0 | 173.9 | 90.5 | x | |
| Glycolate | 0.35 | 27.8 | 4976.9 | 699.3 | 506.0 | 0.0 | 2767.5 | 736.0 | 602.0 | | x |
| cis-Aconitate | 0.34 | 0.0 | 551.8 | 62.9 | 42.6 | 0.0 | 236.2 | 68.8 | 53.0 | | x |
| Propylene glycol | 0.30 | 0.0 | 3745.6 | 227.6 | 60.4 | 0.0 | 5091.3 | 190.0 | 0.0 | x | |
| Tartrate | 0.28 | 0.0 | 442.9 | 9.3 | 0.0 | 0.0 | 63.4 | 1.6 | 0.0 | x | |
| Pyroglutamate | 0.26 | 0.0 | 536.1 | 21.7 | 13.2 | 0.0 | 195.9 | 19.9 | 8.5 | x | |
| Alanine | 0.25 | 0.0 | 1431.5 | 169.3 | 110.5 | 0.0 | 786.7 | 179.6 | 138.8 | | x |
| Acetone | 0.25 | 0.0 | 115.1 | 10.0 | 6.8 | 0.0 | 1788.4 | 57.2 | 7.7 | | x |
| Hippurate | 0.23 | 0.0 | 1057.1 | 147.3 | 98.3 | 0.0 | 813.4 | 95.6 | 53.8 | x | |
| 2-Hydroxyisobutyrate | 0.22 | 0.0 | 643.1 | 30.9 | 21.6 | 0.0 | 148.5 | 33.4 | 24.8 | | x |
| Serine | 0.21 | 0.0 | 917.4 | 126.6 | 92.8 | 0.0 | 965.2 | 148.8 | 99.5 | | x |
| Histidine | 0.20 | 19.0 | 45262.7 | 1675.2 | 862.7 | 51.2 | 7274.5 | 1461.1 | 849.1 | x | |
| 3-Aminoisobutyrate | 0.20 | 0.0 | 1605.2 | 83.4 | 36.2 | 0.0 | 3350.0 | 160.5 | 57.5 | | x |
| Betaine | 0.18 | 0.0 | 2675.7 | 90.9 | 51.9 | 0.0 | 457.9 | 81.5 | 51.5 | x | |
| Glycine | 0.18 | 0.0 | 1337.0 | 7.3 | 0.0 | 0.0 | 0.0 | 0.0 | 0.0 | x | |
| Butyrate | 0.14 | 0.0 | 96.4 | 3.0 | 0.0 | 0.0 | 57.4 | 3.9 | 0.0 | | x |

TABLE 1-continued

| | VIP scores (Normal group vs. CRC group) with concentration analysis (concentrations in μM) | | | | | | | | | |
|---|---|---|---|---|---|---|---|---|---|---|
| | VIP | Normals | | | | Cancer | | | | Higher in | Higher in |
| Var ID (Primary) | score | min | max | mean | median | min | max | mean | median | Normal | Cancer |
| trans-Aconitate | 0.07 | 0.0 | 530.1 | 12.3 | 0.0 | 0.0 | 351.2 | 17.1 | 0.0 | | x |
| 3-Hydroxyisovalerate | 0.07 | 0.0 | 243.3 | 31.3 | 21.9 | 0.0 | 140.1 | 33.3 | 20.6 | | x |
| Methylguanidine | 0.07 | 0.0 | 1054.6 | 57.3 | 21.7 | 0.0 | 490.8 | 33.5 | 17.0 | x | |
| Uracil | 0.06 | 0.0 | 456.2 | 29.1 | 18.4 | 0.0 | 238.1 | 28.3 | 19.3 | x | |
| Mannitol | 0.06 | 0.0 | 1877.4 | 43.5 | 0.0 | 0.0 | 1533.8 | 65.1 | 0.0 | | x |
| Asparagine | 0.02 | 0.0 | 670.6 | 40.2 | 0.0 | 0.0 | 292.0 | 41.1 | 0.0 | | x |
| Glutamine | 0.00 | 0.0 | 13433.0 | 293.2 | 114.4 | 0.0 | 174.8 | 293.3 | 162.8 | | x |

TABLE 2

| | Sensitivity and specificity data (Normal group vs. CRC group) | | | | | | |
|---|---|---|---|---|---|---|---|
| | | Training Set | | | | Testing Set | |
| Model | Cutoff | Sensitivity | Specificity | ROC Curve | R2Y | Q2 | Sensitivity | Specificity |
| Main Model | 0.0885604 | 97.40% | 50.00% | 0.9178 | 0.408 | 0.333 | 94.87% | 56.40% |
| | 0.170391 | 90.91% | 73.22% | | | | 76.92% | 74.41% |
| | 0.226651 | 83.12% | 82.94% | | | | 64.10% | 85.78% |
| | 0.412168 | 50.65% | 97.16% | | | | 20.51% | 98.10% |
| Top 15 | 0.120717 | 88.31% | 57.35% | 0.8281 | 0.231 | 0.195 | 79.49% | 34.12% |
| | 0.136656 | 79.22% | 66.59% | | | | 74.36% | 82.94% |
| | 0.148472 | 71.43% | 71.33% | | | | 66.67% | 91.47% |
| | 0.326168 | 37.66% | 97.16% | | | | 20.51% | 99.53% |
| Top 14 | 0.126112 | 88.31% | 59.48% | 0.8218 | 0.226 | 0.186 | 84.62% | 63.51% |
| | 0.133453 | 81.82% | 64.22% | | | | 82.05% | 68.72% |
| | 0.153027 | 74.03% | 72.75% | | | | 69.23% | 79.15% |
| | 0.306811 | 44.16% | 97.16% | | | | 20.15% | 98.58% |
| Top 13 | 0.129639 | 85.71% | 59.48% | 0.8117 | 0.213 | 0.174 | 84.62% | 63.98% |
| | 0.14178 | 79.22% | 66.82% | | | | 71.79% | 71.56% |
| | 0.150067 | 71.43% | 71.33% | | | | 69.23% | 75.36% |
| | 0.305146 | 38.96% | 97.16% | | | | 17.95% | 99.05% |
| Top 12 | 0.129682 | 85.71% | 58.77% | 0.8069 | 0.209 | 0.17 | 84.62% | 64.93% |
| | 0.142588 | 79.22% | 66.82% | | | | 71.79% | 72.99% |
| | 0.153333 | 72.73% | 72.04% | | | | 69.23% | 78.20% |
| | 0.304388 | 37.66% | 97.16% | | | | 17.95% | 99.53% |
| Top 11 | 0.132533 | 85.71% | 60.19% | 0.8129 | 0.212 | 0.173 | 82.05% | 65.88% |
| | 0.144688 | 79.22% | 68.01% | | | | 71.79% | 75.36% |
| | 0.153709 | 72.73% | 72.51% | | | | 69.23% | 78.20% |
| | 0.302045 | 37.66% | 97.16% | | | | 17.95% | 99.53% |
| Top 10 | 0.133508 | 85.71% | 60.43% | 0.8143 | 0.212 | 0.181 | 84.62% | 67.30% |
| | 0.147835 | 79.22% | 69.91% | | | | 71.79% | 74.88% |
| | 0.155504 | 72.73% | 72.51% | | | | 69.23% | 77.73% |
| | 0.298765 | 36.36% | 97.16% | | | | 20.51% | 98.58% |
| Top 9 | 0.131493 | 85.71% | 60.19% | 0.805 | 0.199 | 0.166 | 79.49% | 65.40% |
| | 0.138175 | 77.92% | 64.93% | | | | 76.92% | 70.14% |
| | 0.148832 | 72.73% | 72.27% | | | | 64.10% | 76.30% |
| | 0.282037 | 36.36% | 97.16% | | | | 17.95% | 97.63% |
| Top 8 | 0.131493 | 85.71% | 60.43% | 0.805 | 0.196 | 0.162 | 84.62% | 63.03% |
| | 0.144356 | 77.92% | 69.43% | | | | 71.79% | 73.93% |
| | 0.149313 | 71.43% | 72.27% | | | | 64.10% | 75.83% |
| | 0.282037 | 36.36% | 97.16% | | | | 17.95% | 98.10% |
| Top 7 | 0.127899 | 85.71% | 54.74% | 0.8033 | 0.196 | 0.169 | 82.05% | 61.14% |
| | 0.141203 | 77.92% | 68.01% | | | | 76.92% | 74.41% |
| | 0.147994 | 71.43% | 71.33% | | | | 69.23% | 76.78% |
| | 0.282972 | 36.36% | 97.16% | | | | 17.95% | 98.58% |
| Top 6 | 0.108354 | 84.42% | 50.00% | 0.7653 | 0.167 | 0.152 | 84.62% | 56.40% |
| | 0.118968 | 75.32% | 57.11% | | | | 82.05% | 63.98% |
| | 0.138547 | 67.53% | 67.30% | | | | 71.79% | 72.99% |
| | 0.312037 | 32.47% | 97.16% | | | | 23.08% | 98.10% |
| Top 5 | 0.117829 | 84.42% | 51.18% | 0.7794 | 0.17 | 0.164 | 89.74% | 56.87% |
| | 0.134735 | 76.62% | 63.74% | | | | 74.36% | 70.14% |
| | 0.145389 | 68.83% | 68.72% | | | | 69.23% | 73.93% |
| | 0.302779 | 28.57% | 97.16% | | | | 20.51% | 98.58% |
| VIP > 1 | 0.114184 | 92.21% | 50.47% | 0.8465 | 0.25 | 0.211 | 87.18% | 54.03% |
| | 0.132386 | 83.12% | 64.22% | | | | 76.92% | 70.14% |
| | 0.152742 | 75.32% | 75.12% | | | | 69.23% | 78.20% |
| | 0.302331 | 48.05% | 97.16% | | | | 25.64% | 98.10% |

** Model named VIP > 1 contains 20 metabolites

TABLE 3

VIP scores (Normal group vs. Polyp group) with concentration analysis (concentrations in μM)

| Var ID (Primary) | VIP score | Normals | | | | Polyps | | | | Higher in Normal | Higher in Polyp |
|---|---|---|---|---|---|---|---|---|---|---|---|
| | | min | max | mean | median | min | max | mean | median | | |
| Butyrate | 2.85 | 0.0 | 95.4 | 3.0 | 0.0 | 0.0 | 15.3 | 0.1 | 0.0 | x | |
| Serine | 2.70 | 0.0 | 982.2 | 87.7 | 0.0 | 0.0 | 651.5 | 45.7 | 0.0 | x | |
| Asparagine | 1.73 | 0.0 | 670.6 | 40.2 | 0.0 | 0.0 | 402.0 | 47.5 | 34.5 | | x |
| p-Methylhistidine | 1.65 | 0.0 | 3745.6 | 227.6 | 60.4 | 0.0 | 2919.3 | 275.5 | 118.9 | | x |
| 3-Hydroxybutyrate | 1.65 | 0.0 | 498.4 | 11.7 | 0.0 | 0.0 | 3392.5 | 19.1 | 0.0 | | x |
| Methanol | 1.59 | 0.0 | 1054.6 | 57.3 | 21.7 | 0.0 | 1019.6 | 39.7 | 17.4 | x | |
| 3-Hydroxymandelate | 1.57 | 0.0 | 2539.3 | 60.0 | 0.0 | 0.0 | 947.6 | 82.2 | 0.7 | | x |
| Tyrosine | 1.52 | 0.0 | 551.8 | 62.9 | 42.6 | 0.0 | 1196.3 | 80.6 | 61.2 | | x |
| Trigonelline | 1.51 | 0.0 | 4771.9 | 246.5 | 128.6 | 0.0 | 1789.8 | 287.8 | 204.6 | | x |
| 6-Alanine | 1.45 | 0.0 | 442.9 | 9.3 | 0.0 | 0.0 | 189.5 | 3.1 | 0.0 | x | |
| Histidine | 1.38 | 0.0 | 2108.5 | 208.4 | 106.5 | 0.0 | 3400.1 | 267.0 | 153.6 | | x |
| Dimethylamine | 1.36 | 8.2 | 1494.3 | 194.3 | 135.0 | 17.3 | 1146.5 | 225.3 | 177.2 | | x |
| Urea | 1.28 | 6976.6 | 441697.0 | 127007.5 | 111896.6 | 16667.4 | 376686.7 | 141754.5 | 129086.3 | | x |
| 1,6-Anhydro-I$^2$-D-glucose | 1.25 | 0.0 | 603.3 | 64.5 | 26.9 | 0.0 | 1012.1 | 80.3 | 40.1 | | x |
| Glucose | 1.22 | 0.0 | 13433.0 | 293.2 | 114.4 | 0.0 | 63614.4 | 863.9 | 130.8 | | x |
| Ethanol | 1.14 | 0.0 | 27789.2 | 250.7 | 0.0 | 0.0 | 6405.3 | 88.9 | 0.0 | x | |
| Benzoate | 1.13 | 0.0 | 567.3 | 3.5 | 0.0 | 0.0 | 6282.2 | 33.9 | 0.0 | | x |
| Acetone | 1.09 | 0.0 | 115.1 | 10.0 | 6.8 | 0.0 | 778.8 | 11.7 | 6.6 | | x |
| Threonine | 1.06 | 0.0 | 976.3 | 71.2 | 48.9 | 0.0 | 441.7 | 79.3 | 60.2 | | x |
| 2-Hydroxyisobutyrate | 1.05 | 0.0 | 643.1 | 30.9 | 21.6 | 0.0 | 162.4 | 33.9 | 27.3 | | x |
| Creatinine | 1.04 | 193.0 | 24617.4 | 5643.3 | 4234.9 | 0.0 | 31595.9 | 6528.6 | 5403.3 | | x |
| 3-Hydroxyphenylacetate | 1.04 | 0.0 | 188.6 | 11.9 | 0.0 | 0.0 | 152.3 | 15.1 | 0.0 | | x |
| 3-Indoxylsulfate | 1.02 | 0.0 | 1317.6 | 120.5 | 82.5 | 0.0 | 585.8 | 130.3 | 100.2 | | x |
| Hippurate | 1.02 | 19.0 | 45262.7 | 1675.2 | 862.7 | 0.0 | 21449.0 | 1947.0 | 1078.2 | | x |
| Ascorbate | 1.01 | 0.0 | 12949.8 | 276.2 | 29.8 | 0.0 | 10663.2 | 236.8 | 0.0 | x | |
| 4-Hydroxyphenylacetate | 1.01 | 0.0 | 1401.1 | 72.6 | 48.8 | 0.0 | 1354.3 | 84.8 | 57.8 | | x |
| N,N-Dimethylglycine | 0.95 | 0.0 | 131.3 | 24.7 | 17.5 | 0.0 | 387.6 | 29.2 | 19.8 | | x |
| Adipate | 0.95 | 0.0 | 103.9 | 1.3 | 0.0 | 0.0 | 837.7 | 6.8 | 0.0 | | x |
| Alanine | 0.95 | 0.0 | 1431.3 | 169.3 | 110.5 | 0.0 | 1621.6 | 185.5 | 137.9 | | x |
| Hypoxanthine | 0.95 | 0.0 | 1022.5 | 21.4 | 9.3 | 0.0 | 555.6 | 23.7 | 14.3 | | x |
| 3-Aminoisobutyrate | 0.85 | 0.0 | 1605.2 | 83.4 | 36.2 | 0.0 | 2222.4 | 89.8 | 34.5 | | x |
| cis-Aconitate | 0.83 | 0.0 | 864.8 | 140.3 | 79.4 | 0.0 | 1289.9 | 169.7 | 105.1 | | x |
| Trimethylamine N-oxide | 0.80 | 7.1 | 8301.4 | 308.6 | 163.1 | 0.0 | 5752.9 | 324.9 | 215.7 | | x |
| 3-Hydroxyisovalerate | 0.79 | 0.0 | 243.3 | 31.3 | 21.9 | 0.0 | 141.5 | 32.8 | 26.9 | | x |
| Mannitol | 0.79 | 0.0 | 4738.5 | 224.5 | 0.0 | 0.0 | 6932.3 | 321.5 | 0.0 | | x |
| trans-Aconitate | 0.75 | 0.0 | 456.2 | 29.1 | 18.4 | 0.0 | 515.1 | 33.1 | 20.8 | | x |
| Valine | 0.72 | 0.0 | 113.8 | 20.3 | 14.2 | 0.0 | 151.2 | 22.8 | 18.4 | | x |
| Trimethylamine | 0.62 | 0.0 | 66.4 | 9.5 | 6.5 | 0.0 | 270.7 | 11.3 | 7.5 | | x |
| t-Methylhistidine | 0.61 | 0.0 | 474.7 | 78.5 | 48.7 | 0.0 | 706.5 | 92.6 | 75.8 | | x |
| Glycine | 0.61 | 27.8 | 4976.9 | 699.3 | 506.0 | 0.0 | 8600.5 | 815.7 | 504.6 | | x |
| Lactate | 0.58 | 0.0 | 2897.0 | 97.8 | 52.0 | 0.0 | 3269.3 | 109.3 | 52.7 | | x |
| Tartrate | 0.55 | 0.0 | 4024.6 | 104.7 | 12.2 | 0.0 | 2263.2 | 104.9 | 16.3 | | x |
| O-Acetylcarnitine | 0.55 | 0.0 | 321.3 | 20.3 | 11.6 | 0.0 | 349.9 | 19.1 | 12.2 | x | |
| Propylene glycol | 0.53 | 0.0 | 539.8 | 35.4 | 10.0 | 0.0 | 594.3 | 38.5 | 4.9 | | x |
| Citrate | 0.52 | 0.0 | 15102.4 | 2099.7 | 1563.5 | 0.0 | 8519.8 | 2126.3 | 1566.6 | | x |
| Pyruvate | 0.51 | 0.0 | 282.0 | 17.9 | 10.7 | 0.0 | 109.7 | 19.7 | 13.0 | | x |
| Betaine | 0.47 | 0.0 | 2675.7 | 90.9 | 51.9 | 0.0 | 740.3 | 84.9 | 59.7 | x | |
| Taurine | 0.47 | 0.0 | 5028.3 | 283.2 | 132.2 | 0.0 | 2142.7 | 302.2 | 182.8 | | x |
| Pyroglutamate | 0.43 | 0.0 | 917.4 | 126.9 | 92.8 | 0.0 | 587.5 | 134.4 | 111.9 | | x |
| Creatine | 0.38 | 0.0 | 10201.1 | 331.0 | 59.1 | 0.0 | 4663.5 | 273.1 | 61.7 | x | |
| Carnitine | 0.34 | 0.0 | 907.1 | 47.8 | 22.7 | 0.0 | 359.8 | 48.1 | 30.6 | | x |
| Methylguanidine | 0.34 | 0.0 | 415.5 | 29.4 | 17.3 | 0.0 | 250.0 | 28.7 | 20.8 | x | |
| Isoleucine | 0.32 | 0.0 | 31.5 | 4.1 | 0.0 | 0.0 | 69.6 | 4.6 | 0.0 | | x |
| Galactose | 0.29 | 0.0 | 614.6 | 12.8 | 0.0 | 0.0 | 248.0 | 6.6 | 0.0 | x | |
| Formate | 0.29 | 5.1 | 772.6 | 121.1 | 96.0 | 0.0 | 1424.0 | 128.3 | 101.4 | | x |
| Uracil | 0.28 | 0.0 | 530.1 | 12.3 | 0.0 | 0.0 | 107.0 | 10.5 | 0.0 | - x | |
| Glycerol | 0.28 | 0.0 | 1337.0 | 7.3 | 0.0 | 0.0 | 2004.9 | 11.3 | 0.0 | | x |
| Lysine | 0.26 | 0.0 | 1877.4 | 43.5 | 0.0 | 0.0 | 604.4 | 42.6 | 0.0 | x | |
| Leucine | 0.24 | 0.0 | 112.4 | 12.6 | 9.7 | 0.0 | 81.7 | 13.9 | 11.5 | | x |
| Sucrose | 0.22 | 0.0 | 888.3 | 45.5 | 13.4 | 0.0 | 5926.7 | 68.3 | 14.6 | | x |
| Xylose | 0.22 | 0.0 | 3078.9 | 77.0 | 0.0 | 0.0 | 1870.0 | 84.2 | 0.0 | | x |
| Acetate | 0.21 | 0.0 | 12892.5 | 85.6 | 33.1 | 0.0 | 6645.0 | 84.8 | 36.8 | x | |
| Guanidoacetate | 0.20 | 0.0 | 1057.1 | 147.3 | 98.3 | 0.0 | 1145.0 | 162.8 | 118.6 | | x |
| Glycolate | 0.20 | 0.0 | 1781.0 | 204.0 | 143.0 | 0.0 | 2980.5 | 228.6 | 162.6 | | x |
| Pantothenate | 0.19 | 0.0 | 535.1 | 21.7 | 13.2 | 0.0 | 177.5 | 17.9 | 11.6 | x | |
| Succinate | 0.16 | 0.0 | 535.6 | 39.0 | 22.5 | 0.0 | 269.3 | 33.7 | 24.2 | x | |
| Glutamine | 0.13 | 0.0 | 2004.7 | 149.7 | 81.6 | 0.0 | 1121.2 | 176.9 | 125.8 | | x |
| 1-Methylnicotinamide | 0.08 | 0.0 | 2763.6 | 35.7 | 13.8 | 0.0 | 381.5 | 21.7 | 14.3 | x | |
| 2-Oxoglutarate | 0.00 | 0.0 | 1255.7 | 56.2 | 27.0 | 0.0 | 488.8 | 56.2 | 30.0 | | x |

TABLE 4

Sensitivity and specificity data (Normal group vs. Polyp group)

| Model | Cutoff | Training Set Sensitivity | Specificity | ROC Curve | R2Y | Q2 | Testing Set Sensitivity | Specificity |
|---|---|---|---|---|---|---|---|---|
| main model | 0.297766 | 88.56% | 50.24% | 0.7673 | 0.194 | 0.115 | 74.79% | 51.66% |
|  | 0.358217 | 78.39% | 62.32% |  |  |  | 67.23% | 59.24% |
|  | 0.398023 | 68.22% | 68.01% |  |  |  | 57.98% | 68.25% |
|  | 0.639182 | 15.68% | 97.16% |  |  |  | 6.72% | 96.21% |
| top 15 | 0.301863 | 74.58% | 50.00% | 0.6763 | 0.0749 | 0.0564 | 64.71% | 42.18% |
|  | 0.319843 | 68.64% | 55.45% |  |  |  | 57.98% | 52.61% |
|  | 0.339898 | 63.14% | 62.80% |  |  |  | 51.26% | 62.09% |
|  | 0.621478 | 8.47% | 97.16% |  |  |  | 3.36% | 98.10% |
| top 14 | 0.304827 | 74.58% | 50.47% | 0.675 | 0.0716 | 0.0541 | 63.87% | 43.13% |
|  | 0.320823 | 68.22% | 55.45% |  |  |  | 58.82% | 52.61% |
|  | 0.340114 | 62.71% | 62.56% |  |  |  | 51.26% | 62.09% |
|  | 0.621743 | 7.63% | 97.16% |  |  |  | 3.36% | 98.58% |
| top 13 | 0.305219 | 75.85% | 50.47% | 0.6802 | 0.0735 | 0.0564 | 67.23% | 44.55% |
|  | 0.323129 | 68.22% | 56.64% |  |  |  | 58.82% | 54.50% |
|  | 0.342031 | 61.86% | 61.85% |  |  |  | 51.26% | 63.51% |
|  | 0.59798 | 8.90% | 97.16% |  |  |  | 5.04% | 98.10% |
| top 12 | 0.316487 | 75.85% | 51.66% | 0.6894 | 0.0783 | 0.0595 | 68.91% | 48.82% |
|  | 0.32912 | 69.92% | 59.48% |  |  |  | 62.18% | 56.40% |
|  | 0.34476 | 63.14% | 62.80% |  |  |  | 52.94% | 66.35% |
|  | 0.589455 | 9.32% | 97.16% |  |  |  | 4.20% | 98.58% |
| top 11 | 0.326944 | 77.97% | 50.71% | 0.6995 | 0.0813 | 0.0589 | 78.15% | 48.82% |
|  | 0.34317 | 70.34% | 60.66% |  |  |  | 63.87% | 59.24% |
|  | 0.352496 | 64.83% | 64.45% |  |  |  | 55.46% | 65.88% |
|  | 0.564702 | 8.90% | 97.16% |  |  |  | 5.88% | 97.16% |
| top 10 | 0.341829 | 79.66% | 50.24% | 0.7036 | 0.0798 | 0.0537 | 82.35% | 47.39% |
|  | 0.351485 | 73.31% | 59.24% |  |  |  | 69.75% | 58.29% |
|  | 0.36358 | 66.10% | 65.88% |  |  |  | 55.46% | 65.40% |
|  | 0.521618 | 10.17% | 97.16% |  |  |  | 4.20% | 95.73% |
| top 9 | 0.333275 | 80.08% | 50.00% | 0.7037 | 0.0803 | 0.0538 | 78.99% | 45.02% |
|  | 0.348153 | 72.03% | 59.72% |  |  |  | 62.18% | 58.29% |
|  | 0.358523 | 64.83% | 64.45% |  |  |  | 55.46% | 64.93% |
|  | 0.544911 | 9.75% | 97.16% |  |  |  | 4.20% | 97.63% |
| top 8 | 0.347543 | 78.81% | 52.84% | 0.7071 | 0.0799 | 0.0552 | 71.43% | 50.24% |
|  | 0.358489 | 72.03% | 62.56% |  |  |  | 59.66% | 59.72% |
|  | 0.364861 | 66.53% | 66.35% |  |  |  | 55.46% | 64.45% |
|  | 0.537677 | 7.20% | 97.16% |  |  |  | 5.04% | 97.63% |
| top 7 | 0.378897 | 78.81% | 51.66% | 0.6997 | 0.0641 | 0.0442 | 73.95% | 50.71% |
|  | 0.382814 | 71.19% | 59.95% |  |  |  | 66.39% | 58.29% |
|  | 0.384873 | 65.68% | 65.40% |  |  |  | 59.66% | 63.51% |
|  | 0.471671 | 11.02% | 97.16% |  |  |  | 3.36% | 97.63% |
| top 6 | 0.385209 | 77.97% | 50.95% | 0.6958 | 0.0574 | 0.0413 | 74.79% | 50.71% |
|  | 0.391155 | 71.19% | 61.14% |  |  |  | 60.50% | 58.77% |
|  | 0.392868 | 66.95% | 66.35% |  |  |  | 55.46% | 64.45% |
|  | 0.460474 | 6.36% | 97.16% |  |  |  | 4.20% | 98.10% |
| top 5 | 0.379823 | 71.61% | 62.80% | 0.6895 | 0.0552 | 0.039 | 53.78% | 59.24% |
|  | 0.381874 | 69.07% | 65.17% |  |  |  | 51.26% | 62.09% |
|  | 0.383028 | 66.95% | 66.82% |  |  |  | 50.42% | 63.98% |
|  | 0.472361 | 5.93% | 97.16% |  |  |  | 1.68% | 96.68% |
| VIP > 1 | 0.329791 | 76.69% | 51.90% | 0.7015 | 0.0976 | 0.0507 | 65.55% | 50.71% |
|  | 0.339597 | 70.36% | 57.82% |  |  |  | 58.82% | 56.40% |
|  | 0.352619 | 64.83% | 64.69% |  |  |  | 56.30% | 64.45% |
|  | 0.577397 | 11.44% | 97.16% |  |  |  | 5.88% | 98.58% |

** Model named VIP > 1 contains 26 metabolites

TABLE 5

VIP scores (Normal group vs. Adenoma group) with concentration analysis (concentrations in μM)

| Var ID (Primary) | VIP score | Normals min | max | mean | median | Adenoma min | max | mean | median | Higher in Normal | Higher in Adenoma |
|---|---|---|---|---|---|---|---|---|---|---|---|
| Butyrate | 3.41 | 0.0 | 96.4 | 3.0 | 0.0 | 0.0 | 10.1 | 0.1 | 0.0 | x |  |
| Serine | 2.65 | 0.0 | 982.2 | 87.7 | 0.0 | 0.0 | 664.1 | 50.5 | 0.0 | x |  |
| Methanol | 2.29 | 0.0 | 1054.6 | 57.3 | 21.7 | 0.0 | 1019.6 | 39.8 | 17.7 | x |  |
| 6-Alanine | 2.03 | 0.0 | 442.9 | 9.3 | 0.0 | 0.0 | 142.7 | 2.0 | 0.0 | x |  |
| p-Methylhistidine | 1.91 | 0.0 | 3745.6 | 227.6 | 60.4 | 0.0 | 3262.4 | 271.9 | 124.6 |  | x |
| 3-Hydroxybutyrate | 1.56 | 0.0 | 498.4 | 11.7 | 0.0 | 0.0 | 3392.5 | 29.4 | 0.0 |  | x |
| Asparagine | 1.56 | 0.0 | 670.6 | 40.2 | 0.0 | 0.0 | 402.0 | 45.9 | 26.9 |  | x |
| Trigonelline | 1.52 | 0.0 | 4771.9 | 246.5 | 128.6 | 0.0 | 2427.3 | 295.1 | 169.6 |  | x |
| 3-Hydroxyphenylacetate | 1.39 | 0.0 | 188.6 | 11.9 | 0.0 | 0.0 | 152.3 | 14.1 | 0.0 |  | x |

TABLE 5-continued

VIP scores (Normal group vs. Adenoma group) with concentration analysis (concentrations in μM)

| Var ID (Primary) | VIP score | Normals min | Normals max | Normals mean | Normals median | Adenoma min | Adenoma max | Adenoma mean | Adenoma median | Higher in Normal | Higher in Adenoma |
|---|---|---|---|---|---|---|---|---|---|---|---|
| Histidine | 1.37 | 0.0 | 2108.5 | 208.4 | 106.5 | 0.0 | 3400.1 | 261.0 | 155.5 | | x |
| Acetone | 1.34 | 0.0 | 115.1 | 10.0 | 6.8 | 0.0 | 778.8 | 14.1 | 6.0 | | x |
| 2-Oxoglutarate | 1.25 | 0.0 | 1256.7 | 56.2 | 27.0 | 0.0 | 553.6 | 48.1 | 12.0 | x | |
| Ethanol | 1.24 | 0.0 | 27789.2 | 250.7 | 0.0 | 0.0 | 4594.5 | 53.7 | 0.0 | x | |
| Adipate | 1.23 | 0.0 | 103.9 | 1.3 | 0.0 | 0.0 | 837.7 | 9.0 | 0.0 | | x |
| 3-Hydroxymandelate | 1.22 | 0.0 | 2539.3 | 60.0 | 0.0 | 0.0 | 1065.4 | 75.7 | 0.0 | | x |
| Tyrosine | 1.20 | 0.0 | 551.8 | 62.9 | 42.6 | 0.0 | 606.8 | 73.4 | 53.4 | | x |
| Benzoate | 1.16 | 0.0 | 567.3 | 3.5 | 0.0 | 0.0 | 6282.2 | 46.0 | 0.0 | | x |
| Propylene glycol | 0.98 | 0.0 | 539.8 | 35.4 | 10.0 | 0.0 | 451.1 | 33.5 | 0.0 | x | |
| t-Methylhistidine | 0.98 | 0.0 | 474.7 | 78.5 | 48.7 | 0.0 | 706.5 | 95.2 | 65.5 | | x |
| O-Acetylcarnitine | 0.97 | 0.0 | 321.3 | 20.3 | 11.6 | 0.0 | 349.9 | 18.2 | 10.5 | x | |
| Creatine | 0.96 | 0.0 | 10201.1 | 331.0 | 58.1 | 0.0 | 5572.1 | 319.9 | 72.5 | x | |
| 1,6-Anhydro-I$^2$-D-glucose | 0.94 | 0.0 | 603.3 | 64.5 | 26.9 | 0.0 | 1764.1 | 87.5 | 35.9 | | x |
| Creatinine | 0.90 | 193.0 | 24617.4 | 5643.3 | 4234.9 | 465.5 | 31595.9 | 6397.5 | 4691.9 | | x |
| Alanine | 0.89 | 0.0 | 1431.3 | 169.3 | 110.5 | 6.2 | 1995.2 | 182.5 | 125.7 | | x |
| 3-Aminoisobutyrate | 0.82 | 0.0 | 1605.2 | 83.4 | 36.2 | 0.0 | 2222.4 | 93.3 | 33.5 | | x |
| Hypoxanthine | 0.82 | 0.0 | 1022.5 | 21.4 | 9.3 | 0.0 | 199.9 | 21.4 | 12.7 | x | |
| Dimethylamine | 0.76 | 8.2 | 1494.3 | 194.3 | 135.0 | 17.9 | 1146.5 | 211.5 | 156.1 | | x |
| Uracil | 0.74 | 0.0 | 530.1 | 12.3 | 0.0 | 0.0 | 107.0 | 9.1 | 0.0 | x | |
| Glycerol | 0.72 | 0.0 | 1337.0 | 7.3 | 0.0 | 0.0 | 635.5 | 3.9 | 0.0 | x | |
| 4-Hydroxyphenylacetate | 0.71 | 0.0 | 1401.1 | 72.6 | 48.8 | 0.0 | 1354.3 | 83.4 | 55.4 | | x |
| 2-Hydroxyisobutyrate | 0.71 | 0.0 | 643.1 | 30.9 | 21.6 | 2.2 | 154.8 | 31.2 | 24.0 | | x |
| Threonine | 0.66 | 0.0 | 976.3 | 71.2 | 48.9 | 0.0 | 430.8 | 70.3 | 53.6 | x | |
| Ascorbate | 0.65 | 0.0 | 12949.8 | 276.2 | 29.8 | 0.0 | 10663.2 | 284.3 | 0.0 | | x |
| 3-Indoxylsulfate | 0.62 | 0.0 | 1317.6 | 120.5 | 82.5 | 0.0 | 845.6 | 121.0 | 89.9 | | x |
| Urea | 0.62 | 6976.6 | 441697.0 | 127007.5 | 111896.6 | 19467.8 | 410148.3 | 130597.5 | 123744.3 | | x |
| Isoleucine | 0.58 | 0.0 | 31.5 | 4.1 | 0.0 | 0.0 | 69.6 | 4.0 | 0.0 | x | |
| Pantothenate | 0.55 | 0.0 | 536.1 | 21.7 | 13.2 | 0.0 | 468.1 | 21.6 | 10.8 | x | |
| cis-Aconitate | 0.52 | 0.0 | 864.8 | 140.3 | 79.4 | 0.0 | 1275.6 | 170.8 | 103.9 | | x |
| Sucrose | 0.51 | 0.0 | 888.3 | 45.5 | 13.4 | 0.0 | 1091.4 | 48.3 | 0.0 | | x |
| Citrate | 0.50 | 0.0 | 15102.4 | 2099.7 | 1563.5 | 0.0 | 8519.8 | 1928.5 | 1180.5 | x | |
| Hippurate | 0.46 | 19.0 | 45262.7 | 1675.2 | 862.7 | 0.0 | 10889.6 | 1802.3 | 935.4 | | x |
| Trimethylamine | 0.45 | 0.0 | 66.4 | 9.5 | 6.5 | 0.0 | 270.7 | 10.9 | 6.9 | | x |
| 1-Methylnicotinamide | 0.45 | 0.0 | 2763.6 | 35.7 | 13.8 | 0.0 | 942.8 | 26.5 | 13.7 | x | |
| Glucose | 0.43 | 0.0 | 13433.0 | 293.2 | 114.4 | 0.0 | 39542.0 | 711.4 | 119.3 | | x |
| 3-Hydroxyisovalerate | 0.40 | 0.0 | 243.3 | 31.3 | 21.9 | 0.0 | 141.5 | 30.9 | 24.7 | x | |
| Leucine | 0.39 | 0.0 | 112.4 | 12.6 | 9.7 | 0.0 | 81.7 | 13.3 | 9.8 | | x |
| N,N-Dimethylglycine | 0.39 | 0.0 | 131.3 | 24.7 | 17.5 | 0.0 | 387.6 | 28.2 | 17.0 | | x |
| Succinate | 0.38 | 0.0 | 536.6 | 39.0 | 22.5 | 0.0 | 291.3 | 34.3 | 20.5 | x | |
| Formate | 0.38 | 5.1 | 772.6 | 121.1 | 96.0 | 0.0 | 1424.1 | 131.4 | 101.0 | | x |
| trans-Aconitate | 0.35 | 0.0 | 456.2 | 29.1 | 18.4 | 0.0 | 449.7 | 33.6 | 18.3 | | x |
| Tartrate | 0.33 | 0.0 | 4024.6 | 104.7 | 12.2 | 0.0 | 2263.2 | 116.3 | 11.2 | | x |
| Carnitine | 0.33 | 0.0 | 907.1 | 47.8 | 22.7 | 0.0 | 347.3 | 46.1 | 29.7 | x | |
| Guanidoacetate | 0.23 | 0.0 | 1057.1 | 147.3 | 98.3 | 0.0 | 1145.0 | 142.3 | 95.8 | x | |
| Gycolate | 0.22 | 0.0 | 1781.0 | 204.0 | 143.0 | 0.0 | 1017.4 | 208.6 | 153.6 | | x |
| Taurine | 0.21 | 0.0 | 5028.3 | 283.2 | 132.2 | 0.0 | 1715.0 | 285.6 | 159.2 | | x |
| Pyruvate | 0.20 | 0.0 | 282.0 | 17.9 | 10.7 | 0.0 | 390.5 | 20.8 | 11.4 | | x |
| Acetate | 0.20 | 0.0 | 12892.6 | 85.6 | 33.1 | 0.0 | 6645.0 | 103.4 | 36.3 | | x |
| Xylose | 0.18 | 0.0 | 3078.9 | 77.0 | 0.0 | 0.0 | 1914.6 | 82.5 | 0.0 | | x |
| Mannitol | 0.15 | 0.0 | 4738.5 | 224.5 | 0.0 | 0.0 | 4200.6 | 221.9 | 0.0 | x | |
| Methylguanidine | 0.15 | 0.0 | 415.5 | 29.4 | 17.3 | 0.0 | 250.0 | 28.5 | 20.6 | x | |
| Lysine | 0.14 | 0.0 | 1877.4 | 43.5 | 0.0 | 0.0 | 604.4 | 40.7 | 0.0 | x | |
| Betaine | 0.13 | 0.0 | 2675.7 | 90.9 | 51.9 | 0.0 | 969.5 | 82.8 | 52.2 | x | |
| Valine | 0.13 | 0.0 | 113.8 | 20.3 | 14.2 | 0.0 | 151.2 | 22.0 | 16.4 | | x |
| Lactate | 0.12 | 0.0 | 2897.0 | 97.8 | 52.0 | 0.0 | 5581.3 | 144.2 | 50.9 | | x |
| Glycine | 0.07 | 27.8 | 4976.9 | 699.3 | 506.0 | 42.9 | 8600.5 | 768.0 | 480.4 | | x |
| Trimethylamine N-oxide | 0.06 | 7.1 | 8301.4 | 308.6 | 163.1 | 0.0 | 1478.1 | 265.2 | 194.8 | x | |
| Pyroglutamate | 0.04 | 0.0 | 917.4 | 126.6 | 92.8 | 0.0 | 587.5 | 133.2 | 100.8 | | x |
| Galactose | 0.03 | 0.0 | 614.8 | 12.8 | 0.0 | 0.0 | 487.3 | 9.7 | 0.0 | x | |
| Glutamine | 0.00 | 0.0 | 2004.7 | 149.7 | 81.6 | 0.0 | 1121.2 | 169.8 | 116.0 | | x |

TABLE 6

Sensitivity and specificity data (Normal group vs. Adenoma group)

| Model | Cutoff | Training Set Sensitivity | Training Set Specificity | ROC Curve | R2Y | Q2 | Validation Set Sensitivity | Validation Set Specificity |
|---|---|---|---|---|---|---|---|---|
| Main Model | 0.25947 | 88.89% | 50.24% | 0.7524 | 0.142 | 0.0463 | 82.72% | 51.18% |
| | 0.294233 | 77.78% | 60.19% | | | | 75.31% | 59.24% |

TABLE 6-continued

Sensitivity and specificity data (Normal group vs. Adenoma group)

| Model | Cutoff | Training Set | | | | | Validation Set | |
|---|---|---|---|---|---|---|---|---|
| | | Sensitivity | Specificity | ROC Curve | R2Y | Q2 | Sensitivity | Specificity |
| | 0.322602 | 66.67% | 66.59% | | | | 67.90% | 67.77% |
| | 0.527314 | 11.11% | 97.16% | | | | 2.47% | 97.16% |
| Top 15 | 0.274543 | 77.78% | 50.95% | 0.6966 | 0.0737 | 0.0398 | 76.54% | 49.76% |
| | 0.28085 | 70.37% | 57.82% | | | | 69.14% | 59.72% |
| | 0.285875 | 62.35% | 62.32% | | | | 59.26% | 64.45% |
| | 0.405516 | 12.35% | 97.16% | | | | 2.47% | 96.68% |
| Top 14 | 0.278997 | 77.78% | 52.37% | 0.6977 | 0.0738 | 0.0426 | 75.31% | 49.29% |
| | 0.284213 | 70.37% | 57.82% | | | | 69.14% | 56.87% |
| | 0.288594 | 62.35% | 61.85% | | | | 59.26% | 63.03% |
| | 0.411351 | 9.88% | 96.92% | | | | 1.23% | 97.63% |
| Top 13 | 0.281655 | 77.78% | 50.95% | 0.6966 | 0.0676 | 0.039 | 74.07% | 48.82% |
| | 0.287454 | 70.37% | 57.82% | | | | 67.90% | 56.87% |
| | 0.29164 | 62.35% | 62.32% | | | | 59.26% | 62.56% |
| | 0.419266 | 7.41% | 97.16% | | | | 1.23% | 97.63% |
| Top 12 | 0.279368 | 78.40% | 50.71% | 0.6978 | 0.0679 | 0.0366 | 77.78% | 48.82% |
| | 0.285647 | 70.37% | 58.53% | | | | 71.60% | 56.87% |
| | 0.29013 | 62.35% | 62.32% | | | | 61.73% | 63.03% |
| | 0.422674 | 7.41% | 97.16% | | | | 1.23% | 97.63% |
| Top 11 | 0.273899 | 79.01% | 50.24% | 0.6909 | 0.0657 | 0.0377 | 81.48% | 51.18% |
| | 0.27869 | 71.60% | 56.64% | | | | 76.54% | 54.98% |
| | 0.286068 | 63.58% | 63.03% | | | | 59.26% | 63.51% |
| | 0.419749 | 7.41% | 97.16% | | | | 1.23% | 97.63% |
| Top 10 | 0.277371 | 78.40% | 50.47% | 0.6929 | 0.0655 | 0.0386 | 79.01% | 51.66% |
| | 0.28425 | 70.99% | 60.43% | | | | 71.60% | 57.82% |
| | 0.289461 | 63.58% | 63.27% | | | | 61.73% | 62.56% |
| | 0.431667 | 7.41% | 97.16% | | | | 1.23% | 98.10% |
| Top 9 | 0.292693 | 75.31% | 50.95% | 0.681 | 0.056 | 0.0311 | 74.07% | 49.29% |
| | 0.295476 | 68.52% | 56.64% | | | | 66.67% | 53.55% |
| | 0.298941 | 63.58% | 62.80% | | | | 61.73% | 61.61% |
| | 0.387558 | 7.41% | 97.16% | | | | 1.23% | 97.63% |
| Top 8 | 0.296909 | 73.46% | 50.24% | 0.6757 | 0.0534 | 0.0317 | 74.07% | 53.55% |
| | 0.300521 | 66.05% | 58.06% | | | | 67.90% | 58.77% |
| | 0.302474 | 62.96% | 62.80% | | | | 59.26% | 61.14% |
| | 0.37303 | 9.26% | 97.16% | | | | 0.00% | 97.63% |
| Top 7 | 0.304543 | 74.69% | 50.24% | 0.6747 | 0.0465 | 0.0313 | 71.60% | 51.66% |
| | 0.308861 | 68.52% | 58.77% | | | | 65.43% | 57.35% |
| | 0.310255 | 63.58% | 63.51% | | | | 60.49% | 60.19% |
| | 0.353752 | 6.79% | 97.16% | | | | 1.23% | 97.63% |
| Top 6 | 0.30621 | 73.46% | 50.47% | 0.6614 | 0.0404 | 0.027 | 71.60% | 52.13% |
| | 0.310248 | 67.28% | 54.27% | | | | 67.90% | 55.45% |
| | 0.312955 | 60.49% | 60.43% | | | | 60.49% | 61.14% |
| | 0.342299 | 4.94% | 97.16% | | | | 2.47% | 96.21% |
| Top 5 | 0.304164 | 73.46% | 50.00% | 0.6581 | 0.0362 | 0.029 | 72.84% | 51.66% |
| | 0.309997 | 66.67% | 54.50% | | | | 69.14% | 55.45% |
| | 0.312623 | 61.11% | 60.90% | | | | 60.49% | 60.19% |
| | 0.33285 | 7.41% | 97.16% | | | | 2.47% | 96.68% |
| VIP > 1 | 0.258307 | 77.78% | 50.47% | 0.6937 | 0.0801 | 0.0408 | 82.72% | 49.76% |
| | 0.26743 | 69.14% | 56.87% | | | | 72.84% | 59.24% |
| | 0.274993 | 61.73% | 61.61% | | | | 61.73% | 64.93% |
| | 0.444394 | 11.73% | 97.16% | | | | 3.70% | 97.16% |

** Model named VIP > 1 contains 17 metabolites

TABLE 7

Vectors Unique for OPLS/O2PLS

| Vector | Description |
|---|---|
| To | Matrix of scores that summarizes the X variation orthogonal to Y. |
| Tocv | Matrix of cross validated orthogonal scores To |
| ToPS | Matrix of scores that summarizes the X variation orthogonal to Y for the predictionset. |
| ToPScv | Matrix of cross validated predicted scores ToPS for the predictionset. |
| Uo | Matrix of scores that summarizes the Y variation orthogonal to X. |
| Po | Orthogonal loadings of the X-part of the model. Po expresses the importance of the variables in approximating X variation orthogonal to Y, in the selected component. |
| Po(corr) | Orthogonal loadings Po, scaled as the correlation coefficient between X and To, in the selected component. |
| Pocv | Orthogonal loadings Po from the X-part of the model, for a selected model dimension, computed from the selected cross validation round. |
| Wo | Weights that combine the X variables (first dimension) or the X residuals (subsequent |

TABLE 7-continued

Vectors Unique for OPLS/O2PLS

| Vector | Description |
| --- | --- |
|  | dimensions) to form the scores To.<br>These weights are selected so as to minimize the correlation between To and U, thereby indirectly between To and Y. |
| Wocv | Orthogonal weights Wo from the X-part of the model, for a selected model dimension, computed from the selected cross validation round. |
| Qo | Orthogonal loadings of the Y-part of the model.<br>Qo expresses the importance of the variables in approximating Y variation orthogonal to X, in the selected component. |
| Qocv | Orthogonal loadings Qo from the Y-part of the model, for a selected model dimension, computed from the selected cross validation round. |
| Co | Weights that combine the Y variables (first dimension) or the Y residuals (subsequent dimensions) to form the scores Uo.<br>These weights are selected so as to minimize the correlation between Uo and T, thereby indirectly between Uo and X. |
| Cocv | Orthogonal weights Co from the Y-part of the model, for a selected model dimension, computed from the selected cross validation round. |
| Q | Loadings of the Y-part of the model.<br>Q expresses the importance of the variables in approximating Y variation correlated to X, in the selected component. Y variables with large Q (positive or negative) are highly correlated with T (and X). |
| Qcv | Loadings Q from the Y-part of the model, for a selected model dimension, computed from the selected cross validation round. |
| R | R is the projection of Uo on X.<br>R contains non-zero entries when the score matrix Uo is not completely orthogonal to X. The norm of this matrix is usually very small but is used to enhance the predictions of X. |
| S | S is the projection of To on Y.<br>S contains non-zero entries when the score matrix To is not completely orthogonal to Y. The norm of this matrix is usually very small but is used to enhance the predictions of Y. |
| Y-Related Profiles | Display the estimated pure profiles of the underlying constituents in X under the assumption of additive Y-variables.<br>Estimation includes a linear transformation of the Coefficient matrix, $Bp(Bp^TBp)^{-1}$, where Bp is the Coefficient matrix using only the predictive components to compute the Coefficient matrix (i.e., the components orthogonal to Y are not included in the computation of Bp). |

The citation of any publication herein is for its disclosure prior to the filing date and should not be construed as an admission that the present invention is not entitled to antedate such publication by virtue of prior invention.

Unless defined otherwise, all technical and scientific terms used herein have the same meaning as commonly understood to one of ordinary skill in the art to which this invention belongs. As used in this specification and the appended claims, the singular forms "a," "an," and "the" include plural reference unless the context clearly dictates otherwise.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

The invention claimed is:

1. A method for determining the presence of colorectal cancer in a subject, said method comprising:
   a. obtaining a first metabolite profile from a first urine sample collected from the subject, wherein said first metabolite profile is obtained by measuring the concentration of any three or more metabolites selected from 1,6-anhydro-β-d-glucose, 1-methylnicotinamide, 2-hydroxyisobutyrate, 2-oxoglutarate, 3-aminoisobutyrate, 3-hydroxybutyrate, 3-hydroxyisovalerate, 3-hydroxymandelate, 3-hydroxyphenyl acetate, 3-indoxylsulfate, 4-hydroxyphenylacetate, acetate, acetone, adipate, alanine, ascorbate, asparagine, benzoate, betaine, butyrate, carnitine, citrate, creatine, creatinine, dimethylamine, ethanol, formate, galactose, glucose, glutamine, glycerol, glycine, glycolate, guanidoacetate, hippurate, histidine, hypoxanthine, isoleucine, lactate, leucine, lysine, mannitol, methanol, methylguanidine, n,n-dimethylglycine, o-acetylcarnitine, pantothenate, propylene glycol, pyroglutamate, pyruvate, serine, succinate, sucrose, tartrate, taurine, threonine, trigonelline, trimethylamine, trimethylamine n-oxide, tyrosine, uracil, urea, valine, xylose, cis-aconitate, β-alanine, p-methylhistidine, t-methylhistidine, and trans-aconitate,
   b. comparing said first metabolite profile with a reference metabolite profile;
   c. determining the presence of colorectal cancer in the subject based on the comparison in step (b); and
   d. performing a surgical removal of the colorectal cancer in the subject determined to have colorectal cancer.

2. The method of claim 1, wherein the subject does not have symptoms of colorectal cancer.

3. The method of claim 1, wherein step (a) comprises measuring the concentration in said first urine sample of any 3, 4, 5, 6, 7, 8, 9, 10, 11, 12, 13, 14, 15, 16, 17, 18, 19, 20, 21, 22, 23, 24, 25, or 26 metabolites selected from the group consisting of butyrate, serine, asparagine, p-methylhistidine, 3-hydroxybutyrate, methanol, 3-hydroxymandelate, tyrosine, trigonelline, ß-alanine, histidine, dimethylamine, urea, 1,6-anhydro-ß-D-glucose, glucose, ethanol, benzoate, acetone, threonine, 2-hydroxyisobutyrate, creatinine, 3-hydroxyphenylacetate, 3-indoxylsulfate, hippurate, ascorbate, and 4-hydroxyphenylacetate.

4. The method according to claim 1, wherein in step (b), said reference metabolite profile is determined from the concentration of metabolites in urine of individuals in a reference population corresponding to those metabolites measured in step (a).

5. The method according to claim 1, wherein either or both of said first metabolite profile and said reference metabolite profile are obtained using one or more methods selected from the group consisting of nuclear magnetic resonance (NMR) spectroscopy, high performance liquid chromatography (HPLC), gas chromatography, thin layer chromatography, electrochemical analysis, mass spectroscopy, refractive index spectroscopy, ultra-violet spectroscopy, fluorescent analysis, radiochemical analysis, near-infrared spectroscopy, gas chromatography, and light scattering analysis.

6. The method of claim 1, wherein the concentrations of the metabolites are measured using nuclear magnetic resonance (NMR) spectroscopy.

7. The method according to claim 1, wherein multivariate statistical analysis and/or a mathematical method is used in step (c).

8. The method according to claim 7, wherein said multivariate statistical analysis or mathematical method comprises use of one or more of PCA, PLS-DA, OPLS, SVM, discriminant analysis, kernel methods, nonparametric methods, tree-based methods, generalized linear models, generalized additive modes, fuzzy logic based methods, neural networks, or genetic algorithm-based methods.

* * * * *